US008703151B2

(12) United States Patent
Aagaard et al.

(10) Patent No.: US 8,703,151 B2
(45) Date of Patent: Apr. 22, 2014

(54) TUBERCULOSIS VACCINES COMPRISING ANTIGENS EXPRESSED DURING THE LATENT INFECTION PHASE

(71) Applicant: Statens Serum Institut, Copenhagen S (DK)

(72) Inventors: Claus Aagaard, Copenhagen (DK); Carina Vingsbo-Lundberg, Hollviken (SE); Peter Anderson, Bronshoj (DK)

(73) Assignee: Statens Serum Institut, Copenhagen S (DK)

( * ) Notice: Subject to any disclaimer, the term of this patent is extended or adjusted under 35 U.S.C. 154(b) by 0 days.

(21) Appl. No.: 13/623,733

(22) Filed: Sep. 20, 2012

(65) Prior Publication Data

US 2013/0095132 A1 Apr. 18, 2013

Related U.S. Application Data

(60) Division of application No. 13/335,133, filed on Dec. 22, 2011, now Pat. No. 8,293,250, which is a continuation of application No. 13/101,980, filed on May 5, 2011, now Pat. No. 8,101,193, which is a continuation of application No. 11/993,199, filed as application No. PCT/DK2006/000356 on Jun. 20, 2006, now Pat. No. 7,968,105.

(30) Foreign Application Priority Data

Jun. 23, 2005 (DK) .......................... PA 2005 00924
Oct. 5, 2005 (DK) .......................... PA 2005 01393

(51) Int. Cl.
*A61K 39/04* (2006.01)
*A61K 39/02* (2006.01)
*C07H 21/04* (2006.01)

(52) U.S. Cl.
USPC ....... 424/248.1; 424/9.1; 424/9.2; 424/184.1; 424/185.1; 424/234.1; 536/23.1; 536/23.7

(58) Field of Classification Search
USPC ................. 424/9.1, 9.2, 184.1, 185.1, 234.1, 424/248.1; 536/23.1, 23.7
See application file for complete search history.

(56) References Cited

U.S. PATENT DOCUMENTS 6,485,914 B1 11/2002 Izutsu et al.
6,641,814 B1 11/2003 Andersen et al.
2003/0119013 A1* 6/2003 Jiang et al. ........................ 435/6
2003/0180953 A1* 9/2003 Roemer et al. ................ 435/483

FOREIGN PATENT DOCUMENTS

WO WO 01/23388 A2 4/2001
WO WO 01/79274 A2 10/2001
WO WO 03/004520 A2 1/2003
WO WO 2004/006952 A2 1/2004
WO WO 2004/083448 A2 9/2004

OTHER PUBLICATIONS

Agger E. M. et al., "Protective immunity to tuberculosis with Ag85B-ESAT-6 in a synthetic cationic adjuvant system IC31" Vaccine, Butterworth Scientific. Guildford, GB, vol. 24, No. 26, Jun. 29, 2006, pp. 5452-5460.

Andersen, P. et al., "Simultaneous electroelution of whole SDS-polyacrylamide gels for the direct cellular analysis of complex protein mixtures" 1993, J. Immunol. Methods 161, pp. 29-39.

Andersen, P. et al., "Proteins Released from *Mycobacterium tuberculosis* during Growth" 1991, Infect. Immun. 59, pp. 1905-1910.

Betts, J. et al., "Evaluation of a nutrient starvation model of *Mycobacterium tuberculosis* persistence by gene and protein expression profiling" 2002, Molecular Microbiology, 43, pp. 717-731.

Brandt, L. et al., "ESAT-6 Subunit Vaccination against *Mycobacterium tuberculosis*" 2000 Infect. Immun. 68:2, pp. 791-795.

Brooks, J.V., et al., "Boosting Vaccine for Tuberculosis" Infect. Immun 2001, 69(4), pp. 2714-2717.

Colditz, G.A., et al., "Efficacy of BCG Vaccine in the Prevention of Tuberculosis" JAMA 1994, 271, pp. 698-702.

Cole, S.T. et al., "Deciphering the biology of *Mycobacterium tuberculosis* from the complete genome sequence" 1998 Nature 393, pp. 537-544.

Cote-Sierra J. et al., "A new membrane-bound Oprl lipoprotein expression vector High production of heterologous fusion proteins in Gram (-) bacteria and the implications for oral vaccination" 1998, Gene Oct. 9, 221(1), pp. 25-34.

Dietrich J. et al., "Exchanging ESAT6 with TB10.4 in an Ag85B Fusion Molecule-Based Tuberculosis Subunit Vaccine: Efficient Protection and ESAT6-Based Sensitive Monitoring of Vaccine Efficacy" Journal of immunology, vol. 174, No. 10, May 2005, pp. 6332-6339.

Gosselin, E. et al., "Enhanced Antigen Presentation using Human Fcy Receptor (Monocyte/Macrophage)-Specific Immunogens" 1992, J. Immunol. 149, pp. 3477-3481.

Harboe, M. et al., "B-Cell Epitopes and Quantification of the ESAT-6 Protein of *Mycobacterium tuberculosis*" 1998, Infect. Immun. 66:2, pp. 717-723.

Kilgus J. et al., "Analysis of the Permissive Association of a Malaria T Cell Epitope with DR Molecules" J. Immunol., Jan. 1, 1991, 146(1), pp. 307-15.

(Continued)

*Primary Examiner* — Rodney P. Swartz

(74) *Attorney, Agent, or Firm* — Knobbe Martens Olson & Bear LLP

(57) ABSTRACT

The invention is related to an immunogenic composition, vaccine or pharmaceutical composition for preventing, boosting or treating infection caused by a species of the tuberculosis complex (*M. tuberculosis, M. Bovis, M. africanum, M. microti*). The immunogenic composition, vaccine or pharmaceutical composition comprise a fusion polypeptide, which comprises one or more starvation antigens from *M. tuberculosis*, the units of the fusion polypeptide being *M. tuberculosis* antigens. Further, the invention is related to the use of a vaccine comprising a fusion polypeptide sequence or nucleic acid sequence of the invention given at the same time as BCG, either mixed with BCG or administered separately at different sites or routes for preparing said immunogenic composition, vaccine, or pharmaceutical composition.

17 Claims, 8 Drawing Sheets

(56) References Cited

OTHER PUBLICATIONS

Figure 1:
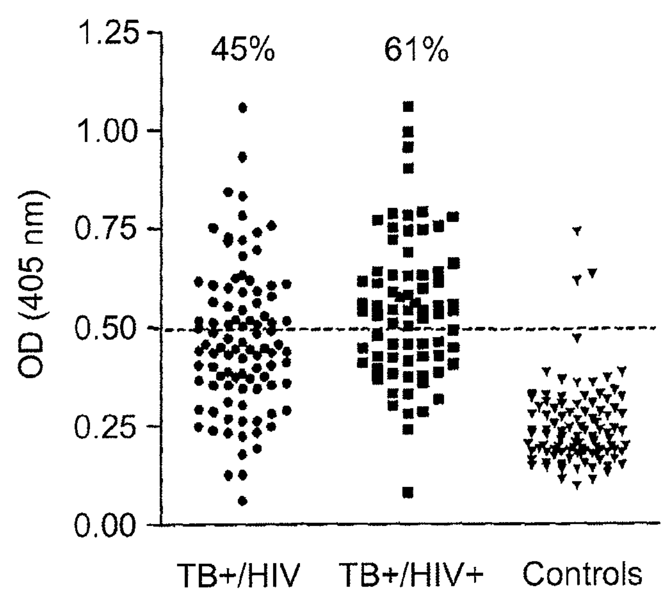

Köhler G. et al., "Continuous cultures of fused cells secreting antibody of predefined specificity" Nature, 1975, 256, pp. 495-497.
Leyten E. et al., "Human T-cell responses to 25 novel antigens encoded by genes of the dormancy regulon of *Mycobacterium tuberculosis*" Microbes and Infection, Elsevier, Paris, FR, vol. 8, No. 8, Jul. 2006, pp. 2052-2060.
Lowrie, D.B. et al., "Therapy of tuberculosis in mice by DNA vaccination" 1999, Nature, 400, pp. 269-271.
Lustig J.V. et al., "Humoral and Cellular Responses to Native Antigen following Oral and Parenteral Immunization with Lipid-Conjugated Bovine Serum Albumin" 1976, Cell Immunol. 24(1), pp. 164-72.
Lyashchenko, K.P. et al., "A multi-antigen print immunoassay for the development of serological diagnosis of infectious diseases" 2000, J. Immunological Methods 242, pp. 91-100.
McCafferty J. et al., "Phage antibodies: filamentous phage displaying antibody variable domains" 1990, Nature, 348, pp. 552-554.
Merrifield, R.B., "Solid Phase Peptide Synthesis. I. The Synthesis of a Tetrapeptide" 1963, J. Am. Chem. Soc. 85 (14), pp. 2149-2154.
Merrifield, R.B. "Peptide Synthesis on a Solid Polymer" Fed. Proc. Am. Soc. Ex. Biol., 1962, p. 412, vol. 21.
Mowat, A.M. et al., "Immune-stimulating complexes containing Quil A and protein antigen prime class I MHC-restricted T lymphocytes in vivo and are immunogenic by the oral route" 1991, Immunology 72(3), pp. 317-322.
Nagai, S. et al., "Isolation and Partial Characterization of Major Protein Antigens in the Culture Fluid of *Mycobacterium tuberculosis*" 1991, Infect. Immun. 59:1, pp. 372-382.
Olsen A. W. et al., "Efficient protection against *Mycobacterium tuberculosis* by vaccination with a single subdominant epitope from the ESAT-6 antigen" Eur. J. Immunol. Jun. 2000, 30(6), pp. 1724-32.
Olsen A. W. et al., "Protection of Mice with a Tuberculosis Subunit Vaccine Based on a Fusion Protein of Antigen 85B and ESAT-6" Infection and Immunity, American Society for Microbiology, vol. 69, No. 5, May 2001, pp. 2773-2778.
Pearson W.R. et al., "Improved tools for biological sequence comparison" 1988, PNAS USA 85, pp. 2444-2448.
Pollock, J. et al., "Assessment of defined antigens for the diagnosis of bovine tuberculosis in skin test-reactor cattle" 2000, The Veterinary record, 146, pp. 659-665.
Ravn, P. et al., "Human T Cell Responses to the ESAT-6 Antigen from *Mycobacterium tuberculosis*" 1999, J. Infect. Dis. 179, pp. 637-645.
Rolph, M.S. et al., "Recombinant viruses as vaccines and immunological tools" 1997, Curr. Opin. Immunol. 9, pp. 517-24.
Rosenkrands, I. et al., "Identification and Characterization of a 29-Kilodalton Protein from *Mycobacterium tuberculosis* Culture Filtrate Recognized by Mouse Memory Effector Cells" 1998, Infect. Immun. 66:6, pp. 2728-2735.
Sherman, D.R. et al., Regulation of the *Mycobacterium tuberculosis* hypoxic response gene encoding alpha-crystallin 2001 Proc Natl Acad Sci USA 98, pp. 7534-7539.
Sinigaglia, F. et al., "A malaria T-cell epitope recognized in association with most mouse and human MHC class II molecules" Nature, Dec. 22-29, 1988, 336(6201), pp. 778-80.
Skjot, R.L.V. et al., "Comparative Evaluation of Low-Molecular-Mass Proteins from *Mycobacterium tuberculosis* Identifies Members of the ESAT-6 Family as Immunodominant T-Cell Antigens" 2000, Infect. Immun. 68:1, pp. 214-220.
Stryhn, A. et al., "Peptide binding specificity of major histocompatibility complex class I resolved into an array of apparently independent subspecificities: quantitation by peptide libraries and improved prediction of binding" 1996 Eur. J. Immunol. 26, pp. 1911-1918.
Thompson J. et al., "Clustal W: Improving the sensitivity of progressive multiple sequence alignment through sequence weighting, position-specific gap penalties and weight matrix choice" Nucleic Acids Res. 1994, 22, pp. 4673-4680.
Theisen, M., et al., "Antigenicity and Immunogenicity of Recombinant Glutamate-Rich Protein of *Plasmodium falciparum* Expressed in *Escherichia coli*" 1995, Clin. Diagn. Lab. Immunol. 2(1), pp. 30-4.
Turner, Joanne et al., "Effective Preexposure Tuberculosis Vaccines Fail to Protect When They Are Given in an Immunotherapeutic Mode" Infection and Immunity, Mar. 2000, p. 1706-1709, vol. 68, No. 3.
Ulmer, Jeffrey B. et al., "Toward the development of DNA vaccines" Current Opinion in Biotechnology, 1996, pp. 653-658, vol. 7.
Ulmer, Jeffrey B. et al., "DNA vaccines" Current Opinion in Biotechnology, 1996, pp. 531-536, vol. 8.
Database UniProt, "Subname:Full=Putative uncharacterized protein" Feb. 1, 1997, XP002563173.
Database UniProt, "Subname:Full=Putative uncharacterized protein Mb2678c;" Oct. 1, 2003, XP002563174.

* cited by examiner

SEQUENCE LISTING

```
<160> NUMBER OF SEQ ID NOS: 97

<210> SEQ ID NO 1
<211> LENGTH: 960
<212> TYPE: DNA
<213> ORGANISM: Mycobacterium tuberculosis
```

<400> SEQUENCE: 1

```
atggctgaca tcccctacgg ccgtgactat cccgacccga tctggtgtga cgaggacggc     60

cagccgatgc cgccggtcgg cgccgaattg ctcgacgaca ttagggcatt cttgcggcgg    120

ttcgtagtct atccaagcga ccatgaactg atcgcgcaca ccctctggat tgcgcattgc    180

tggtttatgg aggcgtggga ctcaacgccc cgaatcgctt ttttgtcacc ggaacccggc    240

tctggcaaga gccgcgcact cgaagtcacg gaaccgctag tgccccggcc ggtgcatgcc    300

atcaactgca caccggccta cctgttccgt cgggtggccg atccggtcgg gcggccgacc    360

gtcctgtacg acgagtgtga caccctgttt ggcccgaaag ctaaagaaca cgaggaaatt    420

cgcggcgtga tcaacgccgg ccaccgcaag ggagccgtcg cgggccgctg cgtcatccgc    480

ggcaagatcg ttgagaccga ggaactgcca gcgtactgtg cggtcgcctt ggccggcctc    540

gacgacctgc ccgacaccat catgtctcgg tcgatcgtgg tgaggatgcg caggagggca    600

ccaaccgaac ccgtggagcc gtggcgcccc cgcgtcaacg gccccgaggc cgagaagctg    660

cacgaccggt tggcgaactg ggcggccgcc attaacccgc tggaaagcgg ttggccggcg    720

atgccggacg gggtgaccga ccggcgcgcc gacgtctggg agtccctggt tgcggttgct    780

gacaccgcgg gcgggcactg gcccaaaacc gcccgtgcaa ccgcagaaac ggatgcaacc    840

gcaaatcgag gagccaagcc cagcataggc gtgctgctgc tgcgggatat ccgtcgagtc    900

ttcagcgacc gggaccggat gcgcaccagc gacatcctga ccggactgaa ccggatggag    960
```

<210> SEQ ID NO 2
<211> LENGTH: 475
<212> TYPE: PRT
<213> ORGANISM: Mycobacterium tuberculosis

<400> SEQUENCE: 2

```
Met Ala Asp Ile Pro Tyr Gly Arg Asp Tyr Pro Asp Pro Ile Trp Cys
1               5                   10                  15

Asp Glu Asp Gly Gln Pro Met Pro Pro Val Gly Ala Glu Leu Leu Asp
            20                  25                  30

Asp Ile Arg Ala Phe Leu Arg Arg Phe Val Val Tyr Pro Ser Asp His
        35                  40                  45

Glu Leu Ile Ala His Thr Leu Trp Ile Ala His Cys Trp Phe Met Glu
    50                  55                  60

Ala Trp Asp Ser Thr Pro Arg Ile Ala Phe Leu Ser Pro Glu Pro Gly
65                  70                  75                  80

Ser Gly Lys Ser Arg Ala Leu Glu Val Thr Glu Pro Leu Val Pro Arg
                85                  90                  95

Pro Val His Ala Ile Asn Cys Thr Pro Ala Tyr Leu Phe Arg Arg Val
            100                 105                 110

Ala Asp Pro Val Gly Arg Pro Thr Val Leu Tyr Asp Glu Cys Asp Thr
        115                 120                 125

Leu Phe Gly Pro Lys Ala Lys Glu His Glu Glu Ile Arg Gly Val Ile
    130                 135                 140

Asn Ala Gly His Arg Lys Gly Ala Val Ala Gly Arg Cys Val Ile Arg
145                 150                 155                 160

Gly Lys Ile Val Glu Thr Glu Glu Leu Pro Ala Tyr Cys Ala Val Ala
                165                 170                 175

Leu Ala Gly Leu Asp Asp Leu Pro Asp Thr Ile Met Ser Arg Ser Ile
            180                 185                 190

Val Val Arg Met Arg Arg Arg Ala Pro Thr Glu Pro Val Glu Pro Trp
        195                 200                 205
```

```
Arg Pro Arg Val Asn Gly Pro Glu Ala Glu Lys Leu His Asp Arg Leu
    210                 215                 220

Ala Asn Trp Ala Ala Ala Ile Asn Pro Leu Glu Ser Gly Trp Pro Ala
225                 230                 235                 240

Met Pro Asp Gly Val Thr Asp Arg Arg Ala Asp Val Trp Glu Ser Leu
                245                 250                 255

Val Ala Val Ala Asp Thr Ala Gly Gly His Trp Pro Lys Thr Ala Arg
            260                 265                 270

Ala Thr Ala Glu Thr Asp Ala Thr Ala Asn Arg Gly Ala Lys Pro Ser
        275                 280                 285

Ile Gly Val Leu Leu Leu Arg Asp Ile Arg Arg Val Phe Ser Asp Arg
    290                 295                 300

Asp Arg Met Arg Thr Ser Asp Ile Leu Thr Gly Leu Asn Arg Met Glu
305                 310                 315                 320

Glu Gly Pro Trp Gly Ser Ile Arg Arg Gly Asp Pro Leu Asp Ala Arg
                325                 330                 335

Gly Leu Ala Thr Arg Leu Gly Arg Tyr Gly Ile Gly Pro Lys Phe Gln
            340                 345                 350

His Ser Gly Gly Glu Pro Pro Tyr Lys Gly Tyr Ser Arg Thr Gln Phe
        355                 360                 365

Glu Asp Ala Trp Ser Arg Tyr Leu Ser Ala Asp Asp Glu Thr Pro Glu
    370                 375                 380

Glu Arg Asp Leu Ser Val Ser Ala Val Ser Ala Val Ser Pro Pro Val
385                 390                 395                 400

Gly Asp Pro Gly Asp Ala Thr Gly Ala Thr Asp Ala Thr Asp Leu Pro
                405                 410                 415

Glu Ala Gly Asp Leu Pro Tyr Glu Pro Pro Ala Pro Asn Gly His Pro
            420                 425                 430

Asn Gly Asp Ala Pro Leu Cys Ser Gly Pro Gly Cys Pro Asn Lys Leu
        435                 440                 445

Leu Ser Thr Glu Ala Lys Ala Ala Gly Lys Cys Arg Pro Cys Arg Gly
    450                 455                 460

Arg Ala Ala Ala Ser Ala Arg Asp Gly Ala Arg
465                 470                 475
```

```
<210> SEQ ID NO 3
<211> LENGTH: 393
<212> TYPE: DNA
<213> ORGANISM: Mycobacterium tuberculosis

<400> SEQUENCE: 3

atgaccgccg tcggcgggtc gccgccgacg cgacgatgcc cggccacaga ggaccgggca     60

cccgcgacag tcgccacacc gtctagcacc gatcctaccg cgtcccgcgc cgtgtcgtgg    120

tggtcggtgc acgagtatgt cgcaccgacc ctggccgccg ccgtggaatg gccgatggcc    180

ggcaccccgg cgtggtgcga cctcgacgac accgacccgg tcaaatgggc cgcgatctgc    240

gacgctgctc ggcattgggc actccgggtg gagacgtgcc aggccgcgtc ggccgaggca    300

tcacgtgacg tatccgccgc cgccgactgg ccggcggtct ctcgggagat ccagcgtcgg    360

cgtgacgcct acattcggcg ggtggtggtc tga                                 393

<210> SEQ ID NO 4
<211> LENGTH: 130
<212> TYPE: PRT
<213> ORGANISM: Mycobacterium tuberculosis
```

<400> SEQUENCE: 4

```
Met Thr Ala Val Gly Gly Ser Pro Pro Thr Arg Arg Cys Pro Ala Thr
1               5                   10                  15

Glu Asp Arg Ala Pro Ala Thr Val Ala Thr Pro Ser Ser Thr Asp Pro
            20                  25                  30

Thr Ala Ser Arg Ala Val Ser Trp Trp Ser Val His Glu Tyr Val Ala
        35                  40                  45

Pro Thr Leu Ala Ala Ala Val Glu Trp Pro Met Ala Gly Thr Pro Ala
    50                  55                  60

Trp Cys Asp Leu Asp Asp Thr Asp Pro Val Lys Trp Ala Ala Ile Cys
65                  70                  75                  80

Asp Ala Ala Arg His Trp Ala Leu Arg Val Glu Thr Cys Gln Ala Ala
                85                  90                  95

Ser Ala Glu Ala Ser Arg Asp Val Ser Ala Ala Ala Asp Trp Pro Ala
            100                 105                 110

Val Ser Arg Glu Ile Gln Arg Arg Arg Asp Ala Tyr Ile Arg Arg Val
        115                 120                 125

Val Val
    130
```

<210> SEQ ID NO 5
<211> LENGTH: 261
<212> TYPE: DNA
<213> ORGANISM: Mycobacterium tuberculosis

<400> SEQUENCE: 5

```
atgtgcgcgt tcccgtcgcc gagtctcggg tggacggtct ctcacgagac cgaaaggccc     60

ggcatggcag acgctccccc gttgtcacgg cggtacatca cgatcagtga ggccgccgaa    120

tatctagcgg tcaccgaccg cacggtccgc cagatgatcg ccgacggccg cctacgcgga    180

taccgctccg gcacccgcct cgtccgtctg cgccgcgatg aggtcgacgg cgccatgcac    240

ccgttcggtg gtgccgcatg a                                              261
```

<210> SEQ ID NO 6
<211> LENGTH: 86
<212> TYPE: PRT
<213> ORGANISM: Mycobacterium tuberculosis

<400> SEQUENCE: 6

```
Met Cys Ala Phe Pro Ser Pro Ser Leu Gly Trp Thr Val Ser His Glu
1               5                   10                  15

Thr Glu Arg Pro Gly Met Ala Asp Ala Pro Pro Leu Ser Arg Arg Tyr
            20                  25                  30

Ile Thr Ile Ser Glu Ala Ala Glu Tyr Leu Ala Val Thr Asp Arg Thr
        35                  40                  45

Val Arg Gln Met Ile Ala Asp Gly Arg Leu Arg Gly Tyr Arg Ser Gly
    50                  55                  60

Thr Arg Leu Val Arg Leu Arg Arg Asp Glu Val Asp Gly Ala Met His
65                  70                  75                  80

Pro Phe Gly Gly Ala Ala
                85
```

<210> SEQ ID NO 7
<211> LENGTH: 363
<212> TYPE: DNA
<213> ORGANISM: Mycobacterium tuberculosis

<400> SEQUENCE: 7

```
atggccgatg cggttaagta cgtagttatg tgcaactgcg acgacgaacc gggagcgctc     60

atcatcgcct ggatcgacga cgaacgaccc gccggcgggc acatacagat gcggtcgaac    120

acccgcttca ccgaaacaca gtggggccgc catatcgagt ggaaactcga atgccgggca    180

tgccgaaagt atgcgccgat atccgagatg accgccgcgg cgatcctcga cggtttcggg    240

gcgaagcttc acgagctgag aacgtcgacc atccccgacg ctgacgatcc atcaatagca    300

gaggcgcgac acgtaattcc gttcagcgca ttatgcttgc gcttgagcca gctaggcggg    360

taa                                                                  363
```

```
<210> SEQ ID NO 8
<211> LENGTH: 120
<212> TYPE: PRT
<213> ORGANISM: Mycobacterium tuberculosis

<400> SEQUENCE: 8

Met Ala Asp Ala Val Lys Tyr Val Val Met Cys Asn Cys Asp Asp Glu
1               5                   10                  15

Pro Gly Ala Leu Ile Ile Ala Trp Ile Asp Asp Glu Arg Pro Ala Gly
            20                  25                  30

Gly His Ile Gln Met Arg Ser Asn Thr Arg Phe Thr Glu Thr Gln Trp
        35                  40                  45

Gly Arg His Ile Glu Trp Lys Leu Glu Cys Arg Ala Cys Arg Lys Tyr
    50                  55                  60

Ala Pro Ile Ser Glu Met Thr Ala Ala Ala Ile Leu Asp Gly Phe Gly
65                  70                  75                  80

Ala Lys Leu His Glu Leu Arg Thr Ser Thr Ile Pro Asp Ala Asp Asp
                85                  90                  95

Pro Ser Ile Ala Glu Ala Arg His Val Ile Pro Phe Ser Ala Leu Cys
            100                 105                 110

Leu Arg Leu Ser Gln Leu Gly Gly
        115                 120
```

```
<210> SEQ ID NO 9
<211> LENGTH: 1128
<212> TYPE: DNA
<213> ORGANISM: Mycobacterium tuberculosis

<400> SEQUENCE: 9

gtgacgcaaa ccggcaagcg tcagagacgc aaattcggtc gcatccgaca gttcaactcc     60

ggccgctggc aagccagcta caccggcccc gacggccgcg tgtacatcgc ccccaaaacc    120

ttcaacgcca agatcgacgc cgaagcatgg ctcaccgacc gccgccgcga aatcgaccga    180

caactatggt ccccggcatc gggtcaggaa gaccgccccg gagccccatt cggtgagtac    240

gccgaaggat ggctgaagca gcgtggaatc aaggaccgca cccgcgccca ctatcgcaaa    300

ctgctggaca accacatcct ggccaccttc gctgacaccg acctacgcga catcaccccg    360

gccgccgtgc gccgctggta cgccaccacc gccgtgggca caccgaccat gcgggcacac    420

tcctacagct tgctgcgcgc aatcatgcag accgccttgg ccgacgacct gatcgactcc    480

aacccctgcc gcatctcagg cgcgtccacc gcccgccgcg tccacaagat caggcccgcc    540

accctcgacg agctggaaac catcaccaaa gccatgcccg acccctacca ggcgttcgtg    600

ctgatggcgg catggctggc catgcgctac ggcgagctga ccgaattacg ccgcaaagac    660

atcgacctgc acggcgaggt tgcgcgggtg cggcgggctg tcgttcgggt gggcgaaggc    720

ttcaaggtga cgacaccgaa aagcgatgcg ggagtgcgcg acataagtat cccgccacat    780
```

```
ctgatacccg ccatcgaaga ccaccttcac aaacacgtca accccggccg ggagtccctg    840

ctgttcccat cggtcaacga ccccaaccgt cacctagcac cctcggcgct gtaccgcatg    900

ttctacaagg cccgaaaagc cgccggccga ccagacttac gggtgcacga ccttcgacac    960

tccggcgccg tgttggctgc atccaccggc gccacactgg ccgaactgat gcagcggcta   1020

ggacacagca cagccggcgc cgcactccgc taccagcacg ccgccaaggg ccgggaccgc   1080

gaaatcgccg cactgttaag caaactggcc gagaaccagg agatgtga                1128
```

<210> SEQ ID NO 10
<211> LENGTH: 375
<212> TYPE: PRT
<213> ORGANISM: Mycobacterium tuberculosis

<400> SEQUENCE: 10

```
Val Thr Gln Thr Gly Lys Arg Gln Arg Arg Lys Phe Gly Arg Ile Arg
1               5                   10                  15

Gln Phe Asn Ser Gly Arg Trp Gln Ala Ser Tyr Thr Gly Pro Asp Gly
            20                  25                  30

Arg Val Tyr Ile Ala Pro Lys Thr Phe Asn Ala Lys Ile Asp Ala Glu
        35                  40                  45

Ala Trp Leu Thr Asp Arg Arg Arg Glu Ile Asp Arg Gln Leu Trp Ser
    50                  55                  60

Pro Ala Ser Gly Gln Glu Asp Arg Pro Gly Ala Pro Phe Gly Glu Tyr
65                  70                  75                  80

Ala Glu Gly Trp Leu Lys Gln Arg Gly Ile Lys Asp Arg Thr Arg Ala
                85                  90                  95

His Tyr Arg Lys Leu Leu Asp Asn His Ile Leu Ala Thr Phe Ala Asp
            100                 105                 110

Thr Asp Leu Arg Asp Ile Thr Pro Ala Ala Val Arg Arg Trp Tyr Ala
        115                 120                 125

Thr Thr Ala Val Gly Thr Pro Thr Met Arg Ala His Ser Tyr Ser Leu
    130                 135                 140

Leu Arg Ala Ile Met Gln Thr Ala Leu Ala Asp Asp Leu Ile Asp Ser
145                 150                 155                 160

Asn Pro Cys Arg Ile Ser Gly Ala Ser Thr Ala Arg Arg Val His Lys
                165                 170                 175

Ile Arg Pro Ala Thr Leu Asp Glu Leu Glu Thr Ile Thr Lys Ala Met
            180                 185                 190

Pro Asp Pro Tyr Gln Ala Phe Val Leu Met Ala Ala Trp Leu Ala Met
        195                 200                 205

Arg Tyr Gly Glu Leu Thr Glu Leu Arg Arg Lys Asp Ile Asp Leu His
    210                 215                 220

Gly Glu Val Ala Arg Val Arg Arg Ala Val Val Arg Val Gly Glu Gly
225                 230                 235                 240

Phe Lys Val Thr Thr Pro Lys Ser Asp Ala Gly Val Arg Asp Ile Ser
                245                 250                 255

Ile Pro Pro His Leu Ile Pro Ala Ile Glu Asp His Leu His Lys His
            260                 265                 270

Val Asn Pro Gly Arg Glu Ser Leu Leu Phe Pro Ser Val Asn Asp Pro
        275                 280                 285

Asn Arg His Leu Ala Pro Ser Ala Leu Tyr Arg Met Phe Tyr Lys Ala
    290                 295                 300

Arg Lys Ala Ala Gly Arg Pro Asp Leu Arg Val His Asp Leu Arg His
305                 310                 315                 320
```

```
Ser Gly Ala Val Leu Ala Ala Ser Thr Gly Ala Thr Leu Ala Glu Leu
                325                 330                 335

Met Gln Arg Leu Gly His Ser Thr Ala Gly Ala Ala Leu Arg Tyr Gln
            340                 345                 350

His Ala Ala Lys Gly Arg Asp Arg Glu Ile Ala Ala Leu Leu Ser Lys
        355                 360                 365

Leu Ala Glu Asn Gln Glu Met
    370                 375


<210> SEQ ID NO 11
<211> LENGTH: 228
<212> TYPE: DNA
<213> ORGANISM: Mycobacterium tuberculosis

<400> SEQUENCE: 11

gtgatagcgg gcgtcgacca ggcgcttgca gcaacaggcc aggctagcca gcgggcggca      60

ggcgcatctg gtggggtcac cgtcggtgtc ggcgtgggca cggaacagag gaacctttcg     120

gtggttgcac cgagtcagtt cacatttagt tcacgcagcc cagattttgt ggatgaaacc     180

gcaggtcaat cgtggtgcgc gatactggga ttgaaccagt ttcactag                  228


<210> SEQ ID NO 12
<211> LENGTH: 75
<212> TYPE: PRT
<213> ORGANISM: Mycobacterium tuberculosis

<400> SEQUENCE: 12

Val Ile Ala Gly Val Asp Gln Ala Leu Ala Ala Thr Gly Gln Ala Ser
1               5                   10                  15

Gln Arg Ala Ala Gly Ala Ser Gly Gly Val Thr Val Gly Val Gly Val
            20                  25                  30

Gly Thr Glu Gln Arg Asn Leu Ser Val Val Ala Pro Ser Gln Phe Thr
        35                  40                  45

Phe Ser Ser Arg Ser Pro Asp Phe Val Asp Glu Thr Ala Gly Gln Ser
    50                  55                  60

Trp Cys Ala Ile Leu Gly Leu Asn Gln Phe His
65                  70                  75


<210> SEQ ID NO 13
<211> LENGTH: 390
<212> TYPE: DNA
<213> ORGANISM: Mycobacterium tuberculosis

<400> SEQUENCE: 13

atgagggctc gcagcgatgc tggaggccag tctgtgaagt cccgcacgtc gaatcggtcc      60

agaagctcgc gccggagccg cgtcaggtca tccatcagtg ccctcgttga taatccgcag     120

gctcggccgc gcgagctccc tgttctgtgc gggtggcccg tagtgcgcgt cgagccggtc     180

tgcgagttcg tgccggagcc ggtttgtgga caggccgagg tgctcggcga gccagccgcc     240

gctcatcggg tcacctcagc ccgccggtca ccctcaacga ccgtttgcag ccgttcgcag     300

aaggcgagcg cggtggtgat cagctccgtc agctcggttg cgcgggtgcg gcgtgcctcg     360

gtgagttcgg tggacgcgac aacagcgtga                                      390


<210> SEQ ID NO 14
<211> LENGTH: 129
<212> TYPE: PRT
<213> ORGANISM: Mycobacterium tuberculosis
```

<400> SEQUENCE: 14

```
Met Arg Ala Arg Ser Asp Ala Gly Gly Gln Ser Val Lys Ser Arg Thr
1               5                   10                  15

Ser Asn Arg Ser Arg Ser Ser Arg Arg Ser Arg Val Arg Ser Ser Ile
            20                  25                  30

Ser Ala Leu Val Asp Asn Pro Gln Ala Arg Pro Arg Glu Leu Pro Val
        35                  40                  45

Leu Cys Gly Trp Pro Val Val Arg Val Glu Pro Val Cys Glu Phe Val
    50                  55                  60

Pro Glu Pro Val Cys Gly Gln Ala Glu Val Leu Gly Glu Pro Ala Ala
65                  70                  75                  80

Ala His Arg Val Thr Ser Ala Arg Arg Ser Pro Ser Thr Thr Val Cys
                85                  90                  95

Ser Arg Ser Gln Lys Ala Ser Ala Val Val Ile Ser Ser Val Ser Ser
            100                 105                 110

Val Ala Arg Val Arg Arg Ala Ser Val Ser Ser Val Asp Ala Thr Thr
        115                 120                 125

Ala
```

<210> SEQ ID NO 15
<211> LENGTH: 273
<212> TYPE: DNA
<213> ORGANISM: Mycobacterium tuberculosis

<400> SEQUENCE: 15

```
atggatgacc tgacgcggct ccggcgcgag cttctggacc gattcgacgt gcgggacttc     60

acagactggc ctccagcatc gctgcgagcc ctcatcgcga cctacgaccc ctggatcgac    120

atgacggcca gcccgccaca gcctgtatcg cccggagggc ctcgactccg actcgtgcga    180

ttaaccacca acccatccgc gagagcagcc cctatcggaa acggtgggga ctcttctgtt    240

tgcgctggtg agaaacagtg ccgcccaccg tag                                 273
```

<210> SEQ ID NO 16
<211> LENGTH: 90
<212> TYPE: PRT
<213> ORGANISM: Mycobacterium tuberculosis

<400> SEQUENCE: 16

```
Met Asp Asp Leu Thr Arg Leu Arg Arg Glu Leu Leu Asp Arg Phe Asp
1               5                   10                  15

Val Arg Asp Phe Thr Asp Trp Pro Pro Ala Ser Leu Arg Ala Leu Ile
            20                  25                  30

Ala Thr Tyr Asp Pro Trp Ile Asp Met Thr Ala Ser Pro Pro Gln Pro
        35                  40                  45

Val Ser Pro Gly Gly Pro Arg Leu Arg Leu Val Arg Leu Thr Thr Asn
    50                  55                  60

Pro Ser Ala Arg Ala Ala Pro Ile Gly Asn Gly Gly Asp Ser Ser Val
65                  70                  75                  80

Cys Ala Gly Glu Lys Gln Cys Arg Pro Pro
                85                  90
```

<210> SEQ ID NO 17
<211> LENGTH: 234
<212> TYPE: DNA
<213> ORGANISM: Mycobacterium tuberculosis

<400> SEQUENCE: 17

```
gtggaggtga gggctagcgc ccgcaagcac ggcatcaacg acgacgccat gctccacgca     60

taccgcaacg cgctgcgcta cgtcgaactg gaataccacg gcgaagttca actgctggtg    120

atcggccccg accaaaccgg gcgcctttta gagctggtca tcccagcaga cgaaccaccc    180

cggattatcc acgccaacgt actacgcccg aagttctacg actacctgag gtga          234


<210> SEQ ID NO 18
<211> LENGTH: 77
<212> TYPE: PRT
<213> ORGANISM: Mycobacterium tuberculosis

<400> SEQUENCE: 18

Val Glu Val Arg Ala Ser Ala Arg Lys His Gly Ile Asn Asp Asp Ala
1               5                   10                  15

Met Leu His Ala Tyr Arg Asn Ala Leu Arg Tyr Val Glu Leu Glu Tyr
            20                  25                  30

His Gly Glu Val Gln Leu Leu Val Ile Gly Pro Asp Gln Thr Gly Arg
        35                  40                  45

Leu Leu Glu Leu Val Ile Pro Ala Asp Glu Pro Pro Arg Ile Ile His
    50                  55                  60

Ala Asn Val Leu Arg Pro Lys Phe Tyr Asp Tyr Leu Arg
65                  70                  75


<210> SEQ ID NO 19
<211> LENGTH: 432
<212> TYPE: DNA
<213> ORGANISM: Mycobacterium tuberculosis

<400> SEQUENCE: 19

atgagtacag tccattcatc aattgatcaa caccctgatt tgttggctct gcgtgccagc     60

ttcgaccgcg ccgccgagtc gacgatcgcg catttcacat tcggtctggc cctgctggcg    120

ggcctgtatg tggctgcatc gccgtggatc gtcggcttca gcgccaccag agggctgcca    180

acgtgtgacc ttatcgtggg gatcgcggtc gcgtacttgg cgtatgggtt cgcgtcggcc    240

ctggatcgca cacacggcat gacctggacg ctacccgtgc tcggtgtgtg ggtcattttc    300

tcgccgtggg tgctaccagg ggtcgcggtg acggctggca tgatgtggtc gcacatcatc    360

gcaggtgcgg tggtagccgt cctgggcttc tacttcggga tgcgcacgcg ggccgcggct    420

aaccaaggat ag                                                        432


<210> SEQ ID NO 20
<211> LENGTH: 143
<212> TYPE: PRT
<213> ORGANISM: Mycobacterium tuberculosis

<400> SEQUENCE: 20

Met Ser Thr Val His Ser Ser Ile Asp Gln His Pro Asp Leu Leu Ala
1               5                   10                  15

Leu Arg Ala Ser Phe Asp Arg Ala Ala Glu Ser Thr Ile Ala His Phe
            20                  25                  30

Thr Phe Gly Leu Ala Leu Leu Ala Gly Leu Tyr Val Ala Ala Ser Pro
        35                  40                  45

Trp Ile Val Gly Phe Ser Ala Thr Arg Gly Leu Pro Thr Cys Asp Leu
    50                  55                  60

Ile Val Gly Ile Ala Val Ala Tyr Leu Ala Tyr Gly Phe Ala Ser Ala
65                  70                  75                  80

Leu Asp Arg Thr His Gly Met Thr Trp Thr Leu Pro Val Leu Gly Val
                85                  90                  95
```

```
Trp Val Ile Phe Ser Pro Trp Val Leu Pro Gly Val Ala Val Thr Ala
            100                 105                 110

Gly Met Met Trp Ser His Ile Ile Ala Gly Ala Val Val Ala Val Leu
        115                 120                 125

Gly Phe Tyr Phe Gly Met Arg Thr Arg Ala Ala Ala Asn Gln Gly
    130                 135                 140


<210> SEQ ID NO 21
<211> LENGTH: 1350
<212> TYPE: DNA
<213> ORGANISM: Mycobacterium tuberculosis

<400> SEQUENCE: 21

atggccgccg tcgtgaagtc cgtcgctctt gccggtagac caacaacacc agaccgggtt      60

catgaggtgc tagggcgcag catgctggtc gacggtctgg acatagtgct cgatctgacc     120

cgttcgggcg gttcatatct ggtcgacgct ataacgggtc ggcgctacct ggacatgttc     180

acattcgttg cctcctcggc actgggtatg aatcccccgg cgctggtgga cgaccgggag     240

ttccatgccg aactcatgca ggccgcgctg aacaagccca gcaattccga cgtgtactcg     300

gtggcgatgg cccgcttcgt cgagaccttc gcccgtgtct tgggcgaccc ggcgctgccg     360

catctgttct tcgtcgaagg gggcgccctg gcggtggaga acgcgctcaa agccgcgttc     420

gactggaaga gtcggcacaa ccaagcccat gggatcgacc cggcgctggg cactcaagtg     480

ctccacctgc gcggggcatt tcacggccgc agcggctata ccctgtcgct gaccaacacc     540

aagccgacca ttaccgcccg gttcccgaaa ttcgactggc cacgcatcga tgcgccgtac     600

atgcggcccg gcctggatga gcccgctatg gccgcgctag aggccgaggc gctacgccag     660

gcccgcgcgg cattcgagac ccgcccgcac gacatcgcgt gttttgtggc cgaacccatc     720

cagggcgagg gtggcgaccg ccatttccgc ccggagtttt tcgctgcgat gcgcgagctg     780

tgcgacgagt ttgatgcact gctgatcttc gacgaagtac agaccggctg cgggttgacc     840

ggaaccgcct gggcatacca gcagttggat gtcgcacccg acatcgtggc gttcggcaag     900

aagacgcagg tatgcggagt gatggccggt cggcgggtgg acgaggtcgc cgacaatgtg     960

ttcgcggtcc catcacggct caactcgaca tggggtggca atcttaccga catggtgcgc    1020

gcccgccgca tcttggaggt catcgaagcc gagggcctgt tcgagcgggc ggtgcagcac    1080

ggtaagtatc tgcgcgcccg gcttgacgaa ctcgccgcgg acttcccggc agtggttctc    1140

gatccgcgcg gccgcgggct gatgtgtgcg tttagcctgc cgaccaccgc cgaccgtgac    1200

gagttgatcc gccagctgtg gcaacgtgcg gtgattgtgt tgccggccgg tgcagacacc    1260

gtgcgattcc gtccaccgct gacggtttca accgccgaga tcgacgccgc gatagccgcg    1320

gtgcgcagcg cgttaccggt ggtgacgtaa                                     1350


<210> SEQ ID NO 22
<211> LENGTH: 449
<212> TYPE: PRT
<213> ORGANISM: Mycobacterium tuberculosis

<400> SEQUENCE: 22

Met Ala Ala Val Val Lys Ser Val Ala Leu Ala Gly Arg Pro Thr Thr
1               5                   10                  15

Pro Asp Arg Val His Glu Val Leu Gly Arg Ser Met Leu Val Asp Gly
            20                  25                  30

Leu Asp Ile Val Leu Asp Leu Thr Arg Ser Gly Gly Ser Tyr Leu Val
        35                  40                  45
```

```
Asp Ala Ile Thr Gly Arg Arg Tyr Leu Asp Met Phe Thr Phe Val Ala
    50                  55                  60

Ser Ser Ala Leu Gly Met Asn Pro Pro Ala Leu Val Asp Asp Arg Glu
65                  70                  75                  80

Phe His Ala Glu Leu Met Gln Ala Ala Leu Asn Lys Pro Ser Asn Ser
                85                  90                  95

Asp Val Tyr Ser Val Ala Met Ala Arg Phe Val Glu Thr Phe Ala Arg
            100                 105                 110

Val Leu Gly Asp Pro Ala Leu Pro His Leu Phe Phe Val Glu Gly Gly
        115                 120                 125

Ala Leu Ala Val Glu Asn Ala Leu Lys Ala Ala Phe Asp Trp Lys Ser
    130                 135                 140

Arg His Asn Gln Ala His Gly Ile Asp Pro Ala Leu Gly Thr Gln Val
145                 150                 155                 160

Leu His Leu Arg Gly Ala Phe His Gly Arg Ser Gly Tyr Thr Leu Ser
                165                 170                 175

Leu Thr Asn Thr Lys Pro Thr Ile Thr Ala Arg Phe Pro Lys Phe Asp
            180                 185                 190

Trp Pro Arg Ile Asp Ala Pro Tyr Met Arg Pro Gly Leu Asp Glu Pro
        195                 200                 205

Ala Met Ala Ala Leu Glu Ala Glu Ala Leu Arg Gln Ala Arg Ala Ala
    210                 215                 220

Phe Glu Thr Arg Pro His Asp Ile Ala Cys Phe Val Ala Glu Pro Ile
225                 230                 235                 240

Gln Gly Glu Gly Gly Asp Arg His Phe Arg Pro Glu Phe Phe Ala Ala
                245                 250                 255

Met Arg Glu Leu Cys Asp Glu Phe Asp Ala Leu Leu Ile Phe Asp Glu
            260                 265                 270

Val Gln Thr Gly Cys Gly Leu Thr Gly Thr Ala Trp Ala Tyr Gln Gln
        275                 280                 285

Leu Asp Val Ala Pro Asp Ile Val Ala Phe Gly Lys Lys Thr Gln Val
    290                 295                 300

Cys Gly Val Met Ala Gly Arg Arg Val Asp Glu Val Ala Asp Asn Val
305                 310                 315                 320

Phe Ala Val Pro Ser Arg Leu Asn Ser Thr Trp Gly Gly Asn Leu Thr
                325                 330                 335

Asp Met Val Arg Ala Arg Arg Ile Leu Glu Val Ile Glu Ala Glu Gly
            340                 345                 350

Leu Phe Glu Arg Ala Val Gln His Gly Lys Tyr Leu Arg Ala Arg Leu
        355                 360                 365

Asp Glu Leu Ala Ala Asp Phe Pro Ala Val Val Leu Asp Pro Arg Gly
    370                 375                 380

Arg Gly Leu Met Cys Ala Phe Ser Leu Pro Thr Thr Ala Asp Arg Asp
385                 390                 395                 400

Glu Leu Ile Arg Gln Leu Trp Gln Arg Ala Val Ile Val Leu Pro Ala
                405                 410                 415

Gly Ala Asp Thr Val Arg Phe Arg Pro Pro Leu Thr Val Ser Thr Ala
            420                 425                 430

Glu Ile Asp Ala Ala Ile Ala Ala Val Arg Ser Ala Leu Pro Val Val
        435                 440                 445

Thr
```

<210> SEQ ID NO 23

<211> LENGTH: 378
<212> TYPE: DNA
<213> ORGANISM: Mycobacterium tuberculosis

<400> SEQUENCE: 23

```
atgcacgaag taggtgggcc gtcacgcggc gatcggctag gccgggatga cagcgaggtg     60

cactcggcga ttcggtttgc tgttgtggcc gctgtcgtcg ggtcggttt cctcattatg    120

ggagcgttgt tggtcagcac gtgcagcggc gtcgacaccg cggcctgcgg cccgccccag    180

cggatcctgc tggcgctggg gggcccgctg atcctgtgtg cggccgggct gtgggcgttt    240

ctgcgcacct accgggtatg gcgtgcggaa ggtacctggt ggggatggca cggcgccggc    300

tggtttttgt tgacgctgat ggtgctgacg ctctgcatag gcgtcccacc gatcgccggc    360

ccggtcatgg cgccgtga                                                   378
```

<210> SEQ ID NO 24
<211> LENGTH: 125
<212> TYPE: PRT
<213> ORGANISM: Mycobacterium tuberculosis

<400> SEQUENCE: 24

```
Met His Glu Val Gly Gly Pro Ser Arg Gly Asp Arg Leu Gly Arg Asp
1               5                   10                  15

Asp Ser Glu Val His Ser Ala Ile Arg Phe Ala Val Val Ala Ala Val
            20                  25                  30

Val Gly Val Gly Phe Leu Ile Met Gly Ala Leu Leu Val Ser Thr Cys
        35                  40                  45

Ser Gly Val Asp Thr Ala Ala Cys Gly Pro Pro Gln Arg Ile Leu Leu
    50                  55                  60

Ala Leu Gly Gly Pro Leu Ile Leu Cys Ala Ala Gly Leu Trp Ala Phe
65                  70                  75                  80

Leu Arg Thr Tyr Arg Val Trp Arg Ala Glu Gly Thr Trp Trp Gly Trp
                85                  90                  95

His Gly Ala Gly Trp Phe Leu Leu Thr Leu Met Val Leu Thr Leu Cys
            100                 105                 110

Ile Gly Val Pro Pro Ile Ala Gly Pro Val Met Ala Pro
        115                 120                 125
```

<210> SEQ ID NO 25
<211> LENGTH: 324
<212> TYPE: DNA
<213> ORGANISM: Mycobacterium tuberculosis

<400> SEQUENCE: 25

```
gtgtccactt acagatcacc ggatcgcgct tggcaggcgc tggcggacgg cactcgccgg     60

gccatcgtgg agcggctggc gcacggcccg ctggccgtcg gcgagttggc ccgcgacctg    120

cccgtcagcc gacccgcggt gtcacagcac ctcaaagtgc tcaagaccgc caggctggtg    180

tgcgaccgcc ccgcgggaac acgccgcgtc taccagctcg acccgacagg ccttgcggca    240

ttgcgcaccg acctcgaccg gttctggaca cgcgccctga ctggctacgc gcagctcatc    300

gactccgaag gagacgacac atga                                            324
```

<210> SEQ ID NO 26
<211> LENGTH: 107
<212> TYPE: PRT
<213> ORGANISM: Mycobacterium tuberculosis

<400> SEQUENCE: 26

```
Val Ser Thr Tyr Arg Ser Pro Asp Arg Ala Trp Gln Ala Leu Ala Asp
1               5                   10                  15

Gly Thr Arg Arg Ala Ile Val Glu Arg Leu Ala His Gly Pro Leu Ala
            20                  25                  30

Val Gly Glu Leu Ala Arg Asp Leu Pro Val Ser Arg Pro Ala Val Ser
        35                  40                  45

Gln His Leu Lys Val Leu Lys Thr Ala Arg Leu Val Cys Asp Arg Pro
    50                  55                  60

Ala Gly Thr Arg Arg Val Tyr Gln Leu Asp Pro Thr Gly Leu Ala Ala
65                  70                  75                  80

Leu Arg Thr Asp Leu Asp Arg Phe Trp Thr Arg Ala Leu Thr Gly Tyr
                85                  90                  95

Ala Gln Leu Ile Asp Ser Glu Gly Asp Asp Thr
            100                 105
```

<210> SEQ ID NO 27
<211> LENGTH: 405
<212> TYPE: DNA
<213> ORGANISM: Mycobacterium tuberculosis

<400> SEQUENCE: 27

```
atgccactct ccgatcatga gcagcggatg cttgaccaga tcgagagcgc tctctacgcc     60

gaagatccca agttcgcatc gagtgtccgt ggcgggggct tccgcgcacc gaccgcgcgg    120

cggcgcctgc agggcgcggc gttgttcatc atcggtctgg ggatgttggt ttccggcgtg    180

gcgttcaaag agaccatgat cggaagtttc ccgatactca gcgttttcgg ttttgtcgtg    240

atgttcggtg gtgtggtgta tgccatcacc ggtcctcggt tgtccggcag gatggatcgt    300

ggcggatcgg ctgctggggc ttcgcgccag cgtcgtacca agggggccgg gggctcattc    360

accagccgta tggaagatcg gttccggcgc cgcttcgacg agtaa                    405
```

<210> SEQ ID NO 28
<211> LENGTH: 134
<212> TYPE: PRT
<213> ORGANISM: Mycobacterium tuberculosis

<400> SEQUENCE: 28

```
Met Pro Leu Ser Asp His Glu Gln Arg Met Leu Asp Gln Ile Glu Ser
1               5                   10                  15

Ala Leu Tyr Ala Glu Asp Pro Lys Phe Ala Ser Ser Val Arg Gly Gly
            20                  25                  30

Gly Phe Arg Ala Pro Thr Ala Arg Arg Arg Leu Gln Gly Ala Ala Leu
        35                  40                  45

Phe Ile Ile Gly Leu Gly Met Leu Val Ser Gly Val Ala Phe Lys Glu
    50                  55                  60

Thr Met Ile Gly Ser Phe Pro Ile Leu Ser Val Phe Gly Phe Val Val
65                  70                  75                  80

Met Phe Gly Gly Val Val Tyr Ala Ile Thr Gly Pro Arg Leu Ser Gly
                85                  90                  95

Arg Met Asp Arg Gly Gly Ser Ala Ala Gly Ala Ser Arg Gln Arg Arg
            100                 105                 110

Thr Lys Gly Ala Gly Gly Ser Phe Thr Ser Arg Met Glu Asp Arg Phe
        115                 120                 125

Arg Arg Arg Phe Asp Glu
    130
```

<210> SEQ ID NO 29

<211> LENGTH: 420
<212> TYPE: DNA
<213> ORGANISM: Mycobacterium tuberculosis

<400> SEQUENCE: 29

```
atgcgtcgag tggttcgtta tctatccgtt gtggtcgcga tcacgctgat gctcaccgcg     60

gaatcagtca gcatagcgac cgccgcggtc ccgccactcc aaccgatccc aggcgttgcg    120

tcggtgtcgc cggctaatgg tgccgtggtg ggggtggcgc acccggtggt ggtgacattc    180

accacgcccg tgaccgatcg ccgcgccgtc gagcggtcca tccgcatcag cacaccgcac    240

aacacgaccg gacacttcga gtgggtcgct agcaatgtcg tgcggtgggt gccccaccgg    300

tattggccac ctcacacccg tgtctcggtg ggtgtgcagg aactgaccga aggattcgag    360

accggtgacg cactgatcgg ggttgccagc atctcggcac ataccttcac ggtcagcaga    420
```

<210> SEQ ID NO 30
<211> LENGTH: 251
<212> TYPE: PRT
<213> ORGANISM: Mycobacterium tuberculosis

<400> SEQUENCE: 30

```
Met Arg Arg Val Val Arg Tyr Leu Ser Val Val Val Ala Ile Thr Leu
1               5                   10                  15

Met Leu Thr Ala Glu Ser Val Ser Ile Ala Thr Ala Ala Val Pro Pro
            20                  25                  30

Leu Gln Pro Ile Pro Gly Val Ala Ser Val Ser Pro Ala Asn Gly Ala
        35                  40                  45

Val Val Gly Val Ala His Pro Val Val Val Thr Phe Thr Thr Pro Val
    50                  55                  60

Thr Asp Arg Arg Ala Val Glu Arg Ser Ile Arg Ile Ser Thr Pro His
65                  70                  75                  80

Asn Thr Thr Gly His Phe Glu Trp Val Ala Ser Asn Val Val Arg Trp
                85                  90                  95

Val Pro His Arg Tyr Trp Pro Pro His Thr Arg Val Ser Val Gly Val
            100                 105                 110

Gln Glu Leu Thr Glu Gly Phe Glu Thr Gly Asp Ala Leu Ile Gly Val
        115                 120                 125

Ala Ser Ile Ser Ala His Thr Phe Thr Val Ser Arg Asn Gly Glu Val
    130                 135                 140

Leu Arg Thr Met Pro Ala Ser Leu Gly Lys Pro Ser Arg Pro Thr Pro
145                 150                 155                 160

Ile Gly Ser Phe His Ala Met Ser Lys Glu Arg Thr Val Val Met Asp
                165                 170                 175

Ser Arg Thr Ile Gly Ile Pro Leu Asn Ser Ser Asp Gly Tyr Leu Leu
            180                 185                 190

Thr Ala His Tyr Ala Val Arg Val Thr Trp Ser Gly Val Tyr Val His
        195                 200                 205

Ser Ala Pro Trp Ser Val Asn Ser Gln Gly Tyr Ala Asn Val Ser His
    210                 215                 220

Gly Cys Ile Asn Leu Ser Pro Asp Asn Ala Ala Trp Tyr Phe Asp Ala
225                 230                 235                 240

Val Thr Val Gly Asp Pro Ile Glu Val Val Gly
                245                 250
```

<210> SEQ ID NO 31
<211> LENGTH: 711
<212> TYPE: DNA

<213> ORGANISM: Mycobacterium tuberculosis

<400> SEQUENCE: 31

```
ttgccaggct cagccggttg gaggaaggta tttggtggga ccggtggcgc caccggggcg     60

ctgccccgac acgggagggg gtcgatcgtg tacgcacgct caaccaccat tgaggcgcaa    120

cctctgtcgg tcgacattgg aatcgcgcat gttcgtgacg tcgtcatgcc cgctttgcag    180

gagatcgacg ggtgtgtcgg ggtgtcgctg ttggtcgacc ggcaatccgg ccggtgcatc    240

gccaccagcg cctgggagac cttggaggcg atgcgcgcca gcgtcgagcg ggtggcaccc    300

atccgcgacc gcgccgcgct gatgttcgcc ggtagtgccc gggtcgagga atgggacatc    360

gccctgttgc accgcgacca cccgtcgcat gagggggcat gcgtgcgcgc cacctggctc    420

aaagtggtgc cagaccagct cggtcggtcc ctggagttct accgcacgtc cgtacttccc    480

gagctggaga gtctggacgg gttctgcagc gccagcctga tggtcgacca ccccgcttgc    540

cggcgtgcgg tgtcgtgctc gacgttcgac agcatggacg cgatggcccg caaccgcgac    600

cgggcgagcg agctgcgcag caggcgcgtc cgggaattgg gagccgaggt cctcgacgtc    660

gccgaattcg aactggcgat cgcacatcta cgggtacccg agctggtctg a             711
```

<210> SEQ ID NO 32
<211> LENGTH: 236
<212> TYPE: PRT
<213> ORGANISM: Mycobacterium tuberculosis

<400> SEQUENCE: 32

```
Leu Pro Gly Ser Ala Gly Trp Arg Lys Val Phe Gly Gly Thr Gly Gly
1               5                   10                  15

Ala Thr Gly Ala Leu Pro Arg His Gly Arg Gly Ser Ile Val Tyr Ala
            20                  25                  30

Arg Ser Thr Thr Ile Glu Ala Gln Pro Leu Ser Val Asp Ile Gly Ile
        35                  40                  45

Ala His Val Arg Asp Val Val Met Pro Ala Leu Gln Glu Ile Asp Gly
    50                  55                  60

Cys Val Gly Val Ser Leu Leu Val Asp Arg Gln Ser Gly Arg Cys Ile
65                  70                  75                  80

Ala Thr Ser Ala Trp Glu Thr Leu Glu Ala Met Arg Ala Ser Val Glu
                85                  90                  95

Arg Val Ala Pro Ile Arg Asp Arg Ala Ala Leu Met Phe Ala Gly Ser
            100                 105                 110

Ala Arg Val Glu Glu Trp Asp Ile Ala Leu Leu His Arg Asp His Pro
        115                 120                 125

Ser His Glu Gly Ala Cys Val Arg Ala Thr Trp Leu Lys Val Val Pro
    130                 135                 140

Asp Gln Leu Gly Arg Ser Leu Glu Phe Tyr Arg Thr Ser Val Leu Pro
145                 150                 155                 160

Glu Leu Glu Ser Leu Asp Gly Phe Cys Ser Ala Ser Leu Met Val Asp
                165                 170                 175

His Pro Ala Cys Arg Arg Ala Val Ser Cys Ser Thr Phe Asp Ser Met
            180                 185                 190

Asp Ala Met Ala Arg Asn Arg Asp Arg Ala Ser Glu Leu Arg Ser Arg
        195                 200                 205

Arg Val Arg Glu Leu Gly Ala Glu Val Leu Asp Val Ala Glu Phe Glu
    210                 215                 220

Leu Ala Ile Ala His Leu Arg Val Pro Glu Leu Val
225                 230                 235
```

<210> SEQ ID NO 33
<211> LENGTH: 366
<212> TYPE: DNA
<213> ORGANISM: Mycobacterium tuberculosis

<400> SEQUENCE: 33

```
gtggagctgc gggattggtt acgggtcgac gtgaaggcgg gaaagccgtt gttcgaccag     60

ctcagaaccc aggtgatcga cggagtccgc gccggcgcat tgccgcccgg cacccggctc    120

ccgacggtgc gtgacttggc cgggcagctg ggcgtggcgg ccaataccgt ggcccgcgcc    180

taccgcgagt tggaatcggc ggcgatcgtc gaaacgcggg gacgcttcgg cactttcatt    240

tcccgcttcg atccgaccga cgccgcgatg gctgccgcgg ccaaggaata tgtcggcgtg    300

gcgcgagcgc tggggctgac gaagtccgat gcgatgcgct atctcaccca cgtgccggac    360

gactga                                                                366
```

<210> SEQ ID NO 34
<211> LENGTH: 121
<212> TYPE: PRT
<213> ORGANISM: Mycobacterium tuberculosis

<400> SEQUENCE: 34

```
Val Glu Leu Arg Asp Trp Leu Arg Val Asp Val Lys Ala Gly Lys Pro
1               5                   10                  15

Leu Phe Asp Gln Leu Arg Thr Gln Val Ile Asp Gly Val Arg Ala Gly
            20                  25                  30

Ala Leu Pro Pro Gly Thr Arg Leu Pro Thr Val Arg Asp Leu Ala Gly
        35                  40                  45

Gln Leu Gly Val Ala Ala Asn Thr Val Ala Arg Ala Tyr Arg Glu Leu
    50                  55                  60

Glu Ser Ala Ala Ile Val Glu Thr Arg Gly Arg Phe Gly Thr Phe Ile
65                  70                  75                  80

Ser Arg Phe Asp Pro Thr Asp Ala Ala Met Ala Ala Ala Ala Lys Glu
                85                  90                  95

Tyr Val Gly Val Ala Arg Ala Leu Gly Leu Thr Lys Ser Asp Ala Met
            100                 105                 110

Arg Tyr Leu Thr His Val Pro Asp Asp
        115                 120
```

<210> SEQ ID NO 35
<211> LENGTH: 453
<212> TYPE: DNA
<213> ORGANISM: Mycobacterium tuberculosis

<400> SEQUENCE: 35

```
atgaacgagg cgctcgacga tatcgatcgg atcctggtgc gcgaactggc cgccgacgga     60

cgtgcgacgc tgtcagagtt ggccacgcga gccgggctgt cggtctcggc ggtccaatcg    120

cgagtgcgcc ggctggagtc tcgtggtgtg gtccagggat attcggcgcg aatcaatccc    180

gaggcggttg ggcatttgtt gtcggcgttc gtggctatca ctcctcttga tccgtctcaa    240

ccagatgatg cccccgcgcg cctagaacat atcgaggagg tcgagtcctg ttactcggtg    300

gccggcgaag agagctacgt cttgctggtg cgcgtcgcgt ccgcacgggc gctcgaggac    360

ctgttgcaac ggatccggac aacggcgaac gtgcggacgc gaagcacgat cattctgaac    420

actttttaca gcgataggca gcatatacca taa                                 453
```

<210> SEQ ID NO 36
<211> LENGTH: 150
<212> TYPE: PRT
<213> ORGANISM: Mycobacterium tuberculosis

<400> SEQUENCE: 36

```
Met Asn Glu Ala Leu Asp Asp Ile Asp Arg Ile Leu Val Arg Glu Leu
1               5                   10                  15

Ala Ala Asp Gly Arg Ala Thr Leu Ser Glu Leu Ala Thr Arg Ala Gly
            20                  25                  30

Leu Ser Val Ser Ala Val Gln Ser Arg Val Arg Arg Leu Glu Ser Arg
        35                  40                  45

Gly Val Val Gln Gly Tyr Ser Ala Arg Ile Asn Pro Glu Ala Val Gly
    50                  55                  60

His Leu Leu Ser Ala Phe Val Ala Ile Thr Pro Leu Asp Pro Ser Gln
65                  70                  75                  80

Pro Asp Asp Ala Pro Ala Arg Leu Glu His Ile Glu Glu Val Glu Ser
                85                  90                  95

Cys Tyr Ser Val Ala Gly Glu Glu Ser Tyr Val Leu Leu Val Arg Val
            100                 105                 110

Ala Ser Ala Arg Ala Leu Glu Asp Leu Leu Gln Arg Ile Arg Thr Thr
        115                 120                 125

Ala Asn Val Arg Thr Arg Ser Thr Ile Ile Leu Asn Thr Phe Tyr Ser
    130                 135                 140

Asp Arg Gln His Ile Pro
145                 150
```

<210> SEQ ID NO 37
<211> LENGTH: 492
<212> TYPE: DNA
<213> ORGANISM: Mycobacterium tuberculosis

<400> SEQUENCE: 37

```
gtgacggtta ccgacgacta cctggccaac aacgtggact acgcgagcgg tttcaagggc     60

ccgctaccga tgccgccgag caaacacatc gcaatcgtgg cgtgcatgga cgcccggctg    120

gacgtctacc gcatgctggg catcaaggag ggcgaggcac acgtcatccg caacgccgga    180

tgcgtggtca ccgacgatgt gatccgttca ctggccatca gccagcggct gctgggaacc    240

cgcgaaatca tcctgctgca ccacaccgac tgtgggatgc tgactttcac cgacgacgac    300

ttcaagcgcg ccatccagga cgagaccggc atcagaccca cgtggtcgcc cgagtcgtac    360

cccgacgccg tcgaggacgt ccgtcagtcg ctgcgccgca tcgaggtcaa cccgttcgtc    420

accaagcaca cgtcgctgcg cggcttcgtc ttcgatgtcg ccaccggcaa actcaacgag    480

gtcacgccct ag                                                        492
```

<210> SEQ ID NO 38
<211> LENGTH: 163
<212> TYPE: PRT
<213> ORGANISM: Mycobacterium tuberculosis

<400> SEQUENCE: 38

```
Val Thr Val Thr Asp Asp Tyr Leu Ala Asn Asn Val Asp Tyr Ala Ser
1               5                   10                  15

Gly Phe Lys Gly Pro Leu Pro Met Pro Pro Ser Lys His Ile Ala Ile
            20                  25                  30

Val Ala Cys Met Asp Ala Arg Leu Asp Val Tyr Arg Met Leu Gly Ile
        35                  40                  45
```

```
Lys Glu Gly Glu Ala His Val Ile Arg Asn Ala Gly Cys Val Val Thr
    50                  55                  60

Asp Asp Val Ile Arg Ser Leu Ala Ile Ser Gln Arg Leu Leu Gly Thr
65                  70                  75                  80

Arg Glu Ile Ile Leu Leu His His Thr Asp Cys Gly Met Leu Thr Phe
                85                  90                  95

Thr Asp Asp Asp Phe Lys Arg Ala Ile Gln Asp Glu Thr Gly Ile Arg
            100                 105                 110

Pro Thr Trp Ser Pro Glu Ser Tyr Pro Asp Ala Val Glu Asp Val Arg
        115                 120                 125

Gln Ser Leu Arg Arg Ile Glu Val Asn Pro Phe Val Thr Lys His Thr
    130                 135                 140

Ser Leu Arg Gly Phe Val Phe Asp Val Ala Thr Gly Lys Leu Asn Glu
145                 150                 155                 160

Val Thr Pro


<210> SEQ ID NO 39
<211> LENGTH: 522
<212> TYPE: DNA
<213> ORGANISM: Mycobacterium tuberculosis

<400> SEQUENCE: 39

atggcggctg gatcaggggg cggcacagtt ggtcttgtcc tgcctcgagt ggcgtcgttg     60

tccggcttgg acggggctcc gacggtaccg gagggcagcg acaaagcact tatgcacttg    120

ggcgacccgc cgagacggtg cgacacccat cccgacggca caagctcagc cgcggccgct    180

cttgttcttc gtcggatcga cgttcaccca cttctgaccg ggcttgggcg agggaggcag    240

acggtgtccc ttcggaacgg tcacctcgtt gccaccgcca accgggcgat actgtcccga    300

cgtcggagcc ggcttacccg gggacgtagc tttacgagcc atctgatcac ctcctgtccc    360

agactcgatg accaccagca ccggcatccc acccgctgtc gcgcggaaca cgccgggtgt    420

acagtcgcaa cctgcatccc caatgcacac gaccctgccc ctggccatca gaccccgagg    480

tggggtcctt ttcgtctaaa accagcttat accagaatat ag                       522


<210> SEQ ID NO 40
<211> LENGTH: 173
<212> TYPE: PRT
<213> ORGANISM: Mycobacterium tuberculosis

<400> SEQUENCE: 40

Met Ala Ala Gly Ser Gly Gly Gly Thr Val Gly Leu Val Leu Pro Arg
1               5                   10                  15

Val Ala Ser Leu Ser Gly Leu Asp Gly Ala Pro Thr Val Pro Glu Gly
            20                  25                  30

Ser Asp Lys Ala Leu Met His Leu Gly Asp Pro Pro Arg Arg Cys Asp
        35                  40                  45

Thr His Pro Asp Gly Thr Ser Ser Ala Ala Ala Ala Leu Val Leu Arg
    50                  55                  60

Arg Ile Asp Val His Pro Leu Leu Thr Gly Leu Gly Arg Gly Arg Gln
65                  70                  75                  80

Thr Val Ser Leu Arg Asn Gly His Leu Val Ala Thr Ala Asn Arg Ala
                85                  90                  95

Ile Leu Ser Arg Arg Arg Ser Arg Leu Thr Arg Gly Arg Ser Phe Thr
            100                 105                 110

Ser His Leu Ile Thr Ser Cys Pro Arg Leu Asp Asp His Gln His Arg
        115                 120                 125
```

```
His Pro Thr Arg Cys Arg Ala Glu His Ala Gly Cys Thr Val Ala Thr
    130                 135                 140

Cys Ile Pro Asn Ala His Asp Pro Ala Pro Gly His Gln Thr Pro Arg
145                 150                 155                 160

Trp Gly Pro Phe Arg Leu Lys Pro Ala Tyr Thr Arg Ile
                165                 170


<210> SEQ ID NO 41
<211> LENGTH: 855
<212> TYPE: DNA
<213> ORGANISM: Mycobacterium tuberculosis

<400> SEQUENCE: 41

gtgccgaacc gacgccgacg caagctctcg acagccatga gcgcggtcgc cgccctggca     60

gttgcaagtc cttgtgcata ttttcttgtc tacgaatcaa ccgaaacgac cgagcggccc    120

gagcaccatg aattcaagca ggcggcggtg ttgaccgacc tgcccggcga gctgatgtcc    180

gcgctatcgc aggggttgtc ccagttcggg atcaacatac cgccggtgcc cagcctgacc    240

gggagcggcg atgccagcac gggtctaacc ggtcctggcc tgactagtcc gggattgacc    300

agcccgggat tgaccagccc gggcctcacc gaccctgccc ttaccagtcc gggcctgacg    360

ccaaccctgc ccggatcact cgccgcgccc ggcaccaccc tggcgccaac gcccggcgtg    420

ggggccaatc cggcgctcac caaccccgcg ctgaccagcc cgaccggggc gacgccggga    480

ttgaccagcc cgacgggttt ggatcccgcg ctgggcggcg ccaacgaaat cccgattacg    540

acgccggtcg gattggatcc cggggctgac ggcacctatc cgatcctcgg tgatccaaca    600

ctggggacca taccgagcag ccccgccacc acctccaccg gcggcggcgg tctcgtcaac    660

gacgtgatgc aggtggccaa cgagttgggc gccagtcagg ctatcgacct gctaaaaggt    720

gtgctaatgc cgtcgatcat gcaggccgtc cagaatggcg gcgcggccgc gccggcagcc    780

agcccgccgg tcccgcccat ccccgcggcc gcggcggtgc caccgacgga cccaatcacc    840

gtgccggtcg cctaa                                                     855


<210> SEQ ID NO 42
<211> LENGTH: 284
<212> TYPE: PRT
<213> ORGANISM: Mycobacterium tuberculosis

<400> SEQUENCE: 42

Val Pro Asn Arg Arg Arg Arg Lys Leu Ser Thr Ala Met Ser Ala Val
1               5                   10                  15

Ala Ala Leu Ala Val Ala Ser Pro Cys Ala Tyr Phe Leu Val Tyr Glu
            20                  25                  30

Ser Thr Glu Thr Thr Glu Arg Pro Glu His His Glu Phe Lys Gln Ala
        35                  40                  45

Ala Val Leu Thr Asp Leu Pro Gly Glu Leu Met Ser Ala Leu Ser Gln
    50                  55                  60

Gly Leu Ser Gln Phe Gly Ile Asn Ile Pro Pro Val Pro Ser Leu Thr
65                  70                  75                  80

Gly Ser Gly Asp Ala Ser Thr Gly Leu Thr Gly Pro Gly Leu Thr Ser
                85                  90                  95

Pro Gly Leu Thr Ser Pro Gly Leu Thr Ser Pro Gly Leu Thr Asp Pro
            100                 105                 110

Ala Leu Thr Ser Pro Gly Leu Thr Pro Thr Leu Pro Gly Ser Leu Ala
        115                 120                 125
```

```
Ala Pro Gly Thr Thr Leu Ala Pro Thr Pro Gly Val Gly Ala Asn Pro
    130                 135                 140

Ala Leu Thr Asn Pro Ala Leu Thr Ser Pro Thr Gly Ala Thr Pro Gly
145                 150                 155                 160

Leu Thr Ser Pro Thr Gly Leu Asp Pro Ala Leu Gly Gly Ala Asn Glu
                165                 170                 175

Ile Pro Ile Thr Thr Pro Val Gly Leu Asp Pro Gly Ala Asp Gly Thr
            180                 185                 190

Tyr Pro Ile Leu Gly Asp Pro Thr Leu Gly Thr Ile Pro Ser Ser Pro
        195                 200                 205

Ala Thr Thr Ser Thr Gly Gly Gly Gly Leu Val Asn Asp Val Met Gln
    210                 215                 220

Val Ala Asn Glu Leu Gly Ala Ser Gln Ala Ile Asp Leu Leu Lys Gly
225                 230                 235                 240

Val Leu Met Pro Ser Ile Met Gln Ala Val Gln Asn Gly Gly Ala Ala
                245                 250                 255

Ala Pro Ala Ala Ser Pro Pro Val Pro Pro Ile Pro Ala Ala Ala Ala
            260                 265                 270

Val Pro Pro Thr Asp Pro Ile Thr Val Pro Val Ala
        275                 280


<210> SEQ ID NO 43
<211> LENGTH: 252
<212> TYPE: DNA
<213> ORGANISM: Mycobacterium tuberculosis

<400> SEQUENCE: 43

gtgaacagcg caatcatcaa gatcgcgaag tgggcgcaat cgcaacaatg gacggttgag     60

gatgacgcca gcggctacac ccgcttctac aacccccagg gcgtctatat tgctcggttt    120

ccggcaacac ctagcaacga gtaccgccgg atgcgagacc tattgggcgc gttgaagaaa    180

gcgggcctga cgtggccacc gccgagcaag aaggaacggc gggcacagca caggaaggaa    240

ggcgcacagt ga                                                        252


<210> SEQ ID NO 44
<211> LENGTH: 83
<212> TYPE: PRT
<213> ORGANISM: Mycobacterium tuberculosis

<400> SEQUENCE: 44

Ala Gln Val Asn Ser Ala Ile Ile Lys Ile Ala Lys Trp Ala Gln Ser
1               5                   10                  15

Gln Gln Trp Thr Val Glu Asp Asp Ala Ser Gly Tyr Thr Arg Phe Tyr
            20                  25                  30

Asn Pro Gln Gly Val Tyr Ile Ala Arg Phe Pro Ala Thr Pro Ser Asn
        35                  40                  45

Glu Tyr Arg Arg Met Arg Asp Leu Leu Gly Ala Leu Lys Lys Ala Gly
    50                  55                  60

Leu Thr Trp Pro Pro Pro Ser Lys Lys Glu Arg Arg Ala Gln His Arg
65                  70                  75                  80

Lys Glu Gly


<210> SEQ ID NO 45
<211> LENGTH: 414
<212> TYPE: DNA
<213> ORGANISM: Mycobacterium tuberculosis

<400> SEQUENCE: 45
```

```
atgggtcaga tccctccaca acccgttcga cgagttctac cgttgatggt agtgcctggt     60

aatgggcaga aatggcggaa taggacggaa acggaggagg ccatgggcga cacctatcgt    120

gaccccgtcg accacttgcg gacgacgcgg ccgcttgccg gcgagtcgct gatcgacgtg    180

gtgcattggc ctgggtatct gttgattgtg gccggtgtcg tcggcggcgt cggagctctt    240

gcggctttcg gcaccggaca tcacgccgag ggcatgacct ttggtgtggt ggcgattgtc    300

gtcacagtgg ttggtttggc gtggctagcg ttcgagcatc ggcggatacg caagattgcc    360

gatcgctggt ataccgaaca tcccgaagtc cggcggcagc ggctggccgg ctag          414


<210> SEQ ID NO 46
<211> LENGTH: 137
<212> TYPE: PRT
<213> ORGANISM: Mycobacterium tuberculosis

<400> SEQUENCE: 46

Met Gly Gln Ile Pro Pro Gln Pro Val Arg Arg Val Leu Pro Leu Met
1               5                   10                  15

Val Val Pro Gly Asn Gly Gln Lys Trp Arg Asn Arg Thr Glu Thr Glu
            20                  25                  30

Glu Ala Met Gly Asp Thr Tyr Arg Asp Pro Val Asp His Leu Arg Thr
        35                  40                  45

Thr Arg Pro Leu Ala Gly Glu Ser Leu Ile Asp Val Val His Trp Pro
    50                  55                  60

Gly Tyr Leu Leu Ile Val Ala Gly Val Val Gly Gly Val Gly Ala Leu
65                  70                  75                  80

Ala Ala Phe Gly Thr Gly His His Ala Glu Gly Met Thr Phe Gly Val
                85                  90                  95

Val Ala Ile Val Val Thr Val Val Gly Leu Ala Trp Leu Ala Phe Glu
            100                 105                 110

His Arg Arg Ile Arg Lys Ile Ala Asp Arg Trp Tyr Thr Glu His Pro
        115                 120                 125

Glu Val Arg Arg Gln Arg Leu Ala Gly
    130                 135


<210> SEQ ID NO 47
<211> LENGTH: 600
<212> TYPE: DNA
<213> ORGANISM: Mycobacterium tuberculosis

<400> SEQUENCE: 47

gtgtcgcgtc gtgccattca cagtggccgg gctgccccgc gtcgctcagg gaattctcat     60

cttgttcttc gcaaccgggt tcccagctca aaggattcac caaggcgccg gccgcatcat    120

gagttcatga ctgagtcgat aggcgagccg ctgagcacca acctgatcga gcgctacctg    180

cgcgcccgcg gccggcgata cttccgtggc caccacgacg ccgagttctt cttcgtcgcc    240

aacgcccacc tgcggctgca cgtccaccta gaaatctctc ccgcctaccg cgacgtgttc    300

acgatcaggg tcagtcccgc atacttcttc cccgccaccg accacacccg gttggcggag    360

atcgtcaacg cgtggaacct gcagaaccac gaggtcaccg cgatcgtgca cgggtcctct    420

gatccgcacc gcatcggcgt ggccgcagag cggtccttga tcagggaccg catccggttc    480

gacgatttcg ccaccttcgt cgacaacgcc gtctcggccg cgacggagct cttcggtcag    540

ctgacggcag ccggattacc tccaaccgcg acgccgccgt tgctgcgaga cgccgggtga    600


<210> SEQ ID NO 48
```

<211> LENGTH: 199
<212> TYPE: PRT
<213> ORGANISM: Mycobacterium tuberculosis

<400> SEQUENCE: 48

```
Val Ser Arg Arg Ala Ile His Ser Gly Arg Ala Ala Pro Arg Arg Ser
1               5                   10                  15

Gly Asn Ser His Leu Val Leu Arg Asn Arg Val Pro Ser Ser Lys Asp
            20                  25                  30

Ser Pro Arg Arg Arg Pro His His Glu Phe Met Thr Glu Ser Ile Gly
        35                  40                  45

Glu Pro Leu Ser Thr Asn Leu Ile Glu Arg Tyr Leu Arg Ala Arg Gly
    50                  55                  60

Arg Arg Tyr Phe Arg Gly His His Asp Ala Glu Phe Phe Phe Val Ala
65                  70                  75                  80

Asn Ala His Leu Arg Leu His Val His Leu Glu Ile Ser Pro Ala Tyr
                85                  90                  95

Arg Asp Val Phe Thr Ile Arg Val Ser Pro Ala Tyr Phe Phe Pro Ala
            100                 105                 110

Thr Asp His Thr Arg Leu Ala Glu Ile Val Asn Ala Trp Asn Leu Gln
        115                 120                 125

Asn His Glu Val Thr Ala Ile Val His Gly Ser Ser Asp Pro His Arg
    130                 135                 140

Ile Gly Val Ala Ala Glu Arg Ser Leu Ile Arg Asp Arg Ile Arg Phe
145                 150                 155                 160

Asp Asp Phe Ala Thr Phe Val Asp Asn Ala Val Ser Ala Ala Thr Glu
                165                 170                 175

Leu Phe Gly Gln Leu Thr Ala Ala Gly Leu Pro Pro Thr Ala Thr Pro
            180                 185                 190

Pro Leu Leu Arg Asp Ala Gly
        195
```

<210> SEQ ID NO 49
<211> LENGTH: 513
<212> TYPE: DNA
<213> ORGANISM: Mycobacterium tuberculosis

<400> SEQUENCE: 49

```
gtgccgtcgg gatgggtgtc gcaccgtctc ggcgggtcgc ccaagtgcat aagtgctttg      60

tcgctgccct ccggtaccgt cggagccccg tccaagccgg acaacgacgc cactcgaggc     120

aggacaagac caactgtgcc gccccctgat ccagccgcca tgggtacctg gaagttcttc     180

cgggcatctg tggatggccg gccggtattc aagaaggagt tcgacaagct tcctgatcag     240

gcccgggccg cgctgatcgt gctaatgcag cggtatctcg tcggcgacct cgccgcaggg     300

agcatcaaac cgattcgtgg cgacattctg gagttgcgat ggcatgaggc gaacaaccac     360

ttccgggtac tgttcttccg ctggggccag catcccgtag cgctgacagc gttctacaag     420

aaccagcaga agactcccaa gacgaagatc gagacggccc tggaccggca gaaaatctgg     480

aaaagagcct tcggcgacac cccaccgatc tga                                  513
```

<210> SEQ ID NO 50
<211> LENGTH: 170
<212> TYPE: PRT
<213> ORGANISM: Mycobacterium tuberculosis

<400> SEQUENCE: 50

```
Val Pro Ser Gly Trp Val Ser His Arg Leu Gly Gly Ser Pro Lys Cys
```

-continued

```
1               5                   10                  15

Ile Ser Ala Leu Ser Leu Pro Ser Gly Thr Val Gly Ala Pro Ser Lys
            20                  25                  30

Pro Asp Asn Asp Ala Thr Arg Gly Arg Thr Arg Pro Thr Val Pro Pro
        35                  40                  45

Pro Asp Pro Ala Ala Met Gly Thr Trp Lys Phe Phe Arg Ala Ser Val
    50                  55                  60

Asp Gly Arg Pro Val Phe Lys Lys Glu Phe Asp Lys Leu Pro Asp Gln
65                  70                  75                  80

Ala Arg Ala Ala Leu Ile Val Leu Met Gln Arg Tyr Leu Val Gly Asp
                85                  90                  95

Leu Ala Ala Gly Ser Ile Lys Pro Ile Arg Gly Asp Ile Leu Glu Leu
            100                 105                 110

Arg Trp His Glu Ala Asn Asn His Phe Arg Val Leu Phe Phe Arg Trp
        115                 120                 125

Gly Gln His Pro Val Ala Leu Thr Ala Phe Tyr Lys Asn Gln Gln Lys
    130                 135                 140

Thr Pro Lys Thr Lys Ile Glu Thr Ala Leu Asp Arg Gln Lys Ile Trp
145                 150                 155                 160

Lys Arg Ala Phe Gly Asp Thr Pro Pro Ile
                165                 170
```

<210> SEQ ID NO 51
<211> LENGTH: 489
<212> TYPE: DNA
<213> ORGANISM: Mycobacterium tuberculosis

<400> SEQUENCE: 51

```
atgtcgttgg cctgggatgt ggtgtcggtc gacaagccgg acgatgtcaa cgtcgtgatc     60

ggccaggcgc acttcatcaa agcggtcgaa gacctgcacg aggccatggt cggcgtgagc    120

ccatcgctac ggttcgggct cgccttttgc gaggcttccg ggccccggtt ggttcgacat    180

accggcaacg atggcgattt ggtcgaactc gcgacccgca ctgcgctggc catcgcggcc    240

gggcatagct tcgtgatctt cttacgtgag ggtttcccca tcaacatcct caacccggtg    300

caggcggtgc ccgaggtctg cacgatctac tgcgccacag ccaatccggt cgacgttgtc    360

gtcgcggtga ccccgcatgg tcgcggcatc gtgggtgttg tcgacgggca gacccctctg    420

ggagtggaga ccgatcgcga cattgcgcag cggcgtgacc tgttgcgcgc catcggttac    480

aagctctga                                                            489
```

<210> SEQ ID NO 52
<211> LENGTH: 162
<212> TYPE: PRT
<213> ORGANISM: Mycobacterium tuberculosis

<400> SEQUENCE: 52

```
Met Ser Leu Ala Trp Asp Val Val Ser Val Asp Lys Pro Asp Asp Val
1               5                   10                  15

Asn Val Val Ile Gly Gln Ala His Phe Ile Lys Ala Val Glu Asp Leu
            20                  25                  30

His Glu Ala Met Val Gly Val Ser Pro Ser Leu Arg Phe Gly Leu Ala
        35                  40                  45

Phe Cys Glu Ala Ser Gly Pro Arg Leu Val Arg His Thr Gly Asn Asp
    50                  55                  60

Gly Asp Leu Val Glu Leu Ala Thr Arg Thr Ala Leu Ala Ile Ala Ala
65                  70                  75                  80
```

```
Gly His Ser Phe Val Ile Phe Leu Arg Glu Gly Phe Pro Ile Asn Ile
                85                  90                  95

Leu Asn Pro Val Gln Ala Val Pro Glu Val Cys Thr Ile Tyr Cys Ala
            100                 105                 110

Thr Ala Asn Pro Val Asp Val Val Val Ala Val Thr Pro His Gly Arg
        115                 120                 125

Gly Ile Val Gly Val Val Asp Gly Gln Thr Pro Leu Gly Val Glu Thr
    130                 135                 140

Asp Arg Asp Ile Ala Gln Arg Arg Asp Leu Leu Arg Ala Ile Gly Tyr
145                 150                 155                 160

Lys Leu


<210> SEQ ID NO 53
<211> LENGTH: 378
<212> TYPE: DNA
<213> ORGANISM: Mycobacterium tuberculosis

<400> SEQUENCE: 53

atgtttactc tccttgtgtc atggttgctc gtggcctgcg ttcctgggtt gttgatgctg      60

gcgaccctcg ggttgggacg gctggaaagg tttctggccc gagacacggt cacggcgacc     120

gacgtcgcgg agtttctcga gcaggccgag gccgtggatg tgcatacgct cgctcggaat     180

ggaatgccgg aggcgctgga ttacctgcat cgacgtcaag cccggcgaat caccgattca     240

ccgccgcttg ggtctggcgc tgggccacgg tatgccgggc cgctgtttgt caccgatctc     300

gatagccccg tcgagccacc ccggcatggc cagcccaatc cgcagtttag aacggctcga     360

cacgcaaatc acgtgtag                                                    378


<210> SEQ ID NO 54
<211> LENGTH: 125
<212> TYPE: PRT
<213> ORGANISM: Mycobacterium tuberculosis

<400> SEQUENCE: 54

Met Phe Thr Leu Leu Val Ser Trp Leu Leu Val Ala Cys Val Pro Gly
1               5                   10                  15

Leu Leu Met Leu Ala Thr Leu Gly Leu Gly Arg Leu Glu Arg Phe Leu
            20                  25                  30

Ala Arg Asp Thr Val Thr Ala Thr Asp Val Ala Glu Phe Leu Glu Gln
        35                  40                  45

Ala Glu Ala Val Asp Val His Thr Leu Ala Arg Asn Gly Met Pro Glu
    50                  55                  60

Ala Leu Asp Tyr Leu His Arg Arg Gln Ala Arg Arg Ile Thr Asp Ser
65                  70                  75                  80

Pro Pro Leu Gly Ser Gly Ala Gly Pro Arg Tyr Ala Gly Pro Leu Phe
                85                  90                  95

Val Thr Asp Leu Asp Ser Pro Val Glu Pro Pro Arg His Gly Gln Pro
            100                 105                 110

Asn Pro Gln Phe Arg Thr Ala Arg His Ala Asn His Val
        115                 120                 125


<210> SEQ ID NO 55
<211> LENGTH: 528
<212> TYPE: DNA
<213> ORGANISM: Mycobacterium tuberculosis

<400> SEQUENCE: 55
```

```
atgcggcttc caggccgtca tgtgttatac gccctgtcgg cggtcaccat gctggcggcc     60

tgctccagca acggtgctcg tggcggcatt gcgtcgacga acatgaatcc gacaaaccca    120

cccgcaactg cggagaccgc taccgtctca ccgacaccgg ctccgcagag cgcgcgaacc    180

gagacctgga ttaaccttca agtcggcgac tgcctggccg acctgccgcc ggcggatctg    240

agccggataa ccgtcacgat tgtcgattgc gcgacagcgc attcggccga ggtatacctg    300

cgtgctccgg tggccgtcga tgccgccgtc gtttccatgg ccaatcgtga ttgtgctgcc    360

ggatttgcgc cctacacagg ccaatccgtc gacaccagcc catactcggt ggcgtatctc    420

atcgactcgc atcaggatag aaccggggcc gatcccaccc cgagcaccgt catctgtttg    480

ctgcagcccg ccaacggtca gttgctcacc gggtcggccc gtcgctga                 528
```

```
<210> SEQ ID NO 56
<211> LENGTH: 175
<212> TYPE: PRT
<213> ORGANISM: Mycobacterium tuberculosis

<400> SEQUENCE: 56

Met Arg Leu Pro Gly Arg His Val Leu Tyr Ala Leu Ser Ala Val Thr
1               5                   10                  15

Met Leu Ala Ala Cys Ser Ser Asn Gly Ala Arg Gly Gly Ile Ala Ser
            20                  25                  30

Thr Asn Met Asn Pro Thr Asn Pro Pro Ala Thr Ala Glu Thr Ala Thr
        35                  40                  45

Val Ser Pro Thr Pro Ala Pro Gln Ser Ala Arg Thr Glu Thr Trp Ile
    50                  55                  60

Asn Leu Gln Val Gly Asp Cys Leu Ala Asp Leu Pro Pro Ala Asp Leu
65                  70                  75                  80

Ser Arg Ile Thr Val Thr Ile Val Asp Cys Ala Thr Ala His Ser Ala
                85                  90                  95

Glu Val Tyr Leu Arg Ala Pro Val Ala Val Asp Ala Ala Val Val Ser
            100                 105                 110

Met Ala Asn Arg Asp Cys Ala Ala Gly Phe Ala Pro Tyr Thr Gly Gln
        115                 120                 125

Ser Val Asp Thr Ser Pro Tyr Ser Val Ala Tyr Leu Ile Asp Ser His
    130                 135                 140

Gln Asp Arg Thr Gly Ala Asp Pro Thr Pro Ser Thr Val Ile Cys Leu
145                 150                 155                 160

Leu Gln Pro Ala Asn Gly Gln Leu Leu Thr Gly Ser Ala Arg Arg
                165                 170                 175
```

```
<210> SEQ ID NO 57
<211> LENGTH: 336
<212> TYPE: DNA
<213> ORGANISM: Mycobacterium tuberculosis

<400> SEQUENCE: 57

atggctgatc gtgtcctgag ggcagtcgc ctcggagccg tgagctatga gaccgaccgc      60

aaccacgacc tggcgccgcg ccagatcgcg cggtaccgca ccgacaacgg cgaggagttc    120

gaagtcccgt tcgccgatga cgccgagatc cccggcacct ggttgtgccg caacggcatg    180

gaaggcaccc tgatcgaggg cgacctgccc gagccgaaga aggttaagcc gccccggacg    240

cactgggaca tgctgctgga gcgccgttcc atcgaagaac tcgaagagtt acttaaggag    300

cgcctcgagc tcattcggtc acgtcggcgc ggctga                              336
```

<210> SEQ ID NO 58
<211> LENGTH: 111
<212> TYPE: PRT
<213> ORGANISM: Mycobacterium tuberculosis

<400> SEQUENCE: 58

```
Met Ala Asp Arg Val Leu Arg Gly Ser Arg Leu Gly Ala Val Ser Tyr
1               5                   10                  15

Glu Thr Asp Arg Asn His Asp Leu Ala Pro Arg Gln Ile Ala Arg Tyr
            20                  25                  30

Arg Thr Asp Asn Gly Glu Glu Phe Glu Val Pro Phe Ala Asp Asp Ala
        35                  40                  45

Glu Ile Pro Gly Thr Trp Leu Cys Arg Asn Gly Met Glu Gly Thr Leu
    50                  55                  60

Ile Glu Gly Asp Leu Pro Glu Pro Lys Lys Val Lys Pro Pro Arg Thr
65                  70                  75                  80

His Trp Asp Met Leu Leu Glu Arg Arg Ser Ile Glu Glu Leu Glu Glu
                85                  90                  95

Leu Leu Lys Glu Arg Leu Glu Leu Ile Arg Ser Arg Arg Arg Gly
            100                 105                 110
```

<210> SEQ ID NO 59
<211> LENGTH: 438
<212> TYPE: DNA
<213> ORGANISM: Mycobacterium tuberculosis

<400> SEQUENCE: 59

```
atggccgact cggatttacc caccaagggg cgccaacgcg gtgtccgcgc cgtcgagctg      60

aacgttgctg cccgcctgga gaacctggcg ctgctgcgca ccctggtcgg cgccatcggc     120

accttcgagg acctggattt cgacgccgtg gccgacctga ggttggcggt ggacgaggtg     180

tgcacccggt tgattcgctc ggccttgccg gatgccaccc tgcgcctggt ggtcgatccg     240

cgaaaagacg aagttgtggt ggaggcttct gctgcctgcg acacccacga cgtggtggca     300

ccgggcagct ttagctggca tgtcctgacc gcgctggccg acgacgtcca gaccttccac     360

gacggtcgcc agcccgatgt agccggcagt gtcttcggca tcacgttgac cgcccgacgg     420

gcggcatcca gcaggtga                                                   438
```

<210> SEQ ID NO 60
<211> LENGTH: 145
<212> TYPE: PRT
<213> ORGANISM: Mycobacterium tuberculosis

<400> SEQUENCE: 60

```
Met Ala Asp Ser Asp Leu Pro Thr Lys Gly Arg Gln Arg Gly Val Arg
1               5                   10                  15

Ala Val Glu Leu Asn Val Ala Ala Arg Leu Glu Asn Leu Ala Leu Leu
            20                  25                  30

Arg Thr Leu Val Gly Ala Ile Gly Thr Phe Glu Asp Leu Asp Phe Asp
        35                  40                  45

Ala Val Ala Asp Leu Arg Leu Ala Val Asp Glu Val Cys Thr Arg Leu
    50                  55                  60

Ile Arg Ser Ala Leu Pro Asp Ala Thr Leu Arg Leu Val Val Asp Pro
65                  70                  75                  80

Arg Lys Asp Glu Val Val Val Glu Ala Ser Ala Ala Cys Asp Thr His
                85                  90                  95

Asp Val Val Ala Pro Gly Ser Phe Ser Trp His Val Leu Thr Ala Leu
            100                 105                 110
```

```
Ala Asp Asp Val Gln Thr Phe His Asp Gly Arg Gln Pro Asp Val Ala
        115                 120                 125

Gly Ser Val Phe Gly Ile Thr Leu Thr Ala Arg Arg Ala Ala Ser Ser
    130                 135                 140

Arg
145


<210> SEQ ID NO 61
<211> LENGTH: 675
<212> TYPE: DNA
<213> ORGANISM: Mycobacterium tuberculosis

<400> SEQUENCE: 61

ttgaccggtg gcgccaccgg ggcgctgccc cgaacaatga aagaggggtg gatcgtgtac      60

gcgcgctcta ccactattca ggcgcaatcc gagtgcatcg acaccggaat tgcgcacgtt     120

cgcgatgtgg ttatgcccgc actgcagggg atggatgggt gcatcggcgt atccctttg     180

gtcgaccggc aatccggcag gtgcatcgcc accagtgcct gggagaccgc ggaagccatg     240

catgcaagcc gggaacaggt aacgccgatc cgcgatcggt gcgcggagat gttcggcggc     300

acgccggccg tcgaggagtg ggagatcgcg gcgatgcatc gcgaccaccg ctcggccgag     360

ggggcgtgtg tgcgggcgac ctgggtcaag gtgccggcgg accaagtaga tcaaggcatc     420

gagtactaca agtcgtccgt cctgccccaa atcgaaggcc tcgacggatt ctgcagcgcc     480

agcctgttgg tcgaccgcac ctccgggcgc gcggtgtctt ccgcgacctt cgacagcttt     540

gacgccatgg agcgcaaccg ggaccagtcg aatgcgctca aggccacatc gctgcgtgag     600

gcgggcggcg aggaactcga tgaatgcgag ttcgagctgg cgctagcgca cctacgggta     660

cccgagctgg tctga                                                       675


<210> SEQ ID NO 62
<211> LENGTH: 224
<212> TYPE: PRT
<213> ORGANISM: Mycobacterium tuberculosis

<400> SEQUENCE: 62

Leu Thr Gly Gly Ala Thr Gly Ala Leu Pro Arg Thr Met Lys Glu Gly
1               5                   10                  15

Trp Ile Val Tyr Ala Arg Ser Thr Thr Ile Gln Ala Gln Ser Glu Cys
            20                  25                  30

Ile Asp Thr Gly Ile Ala His Val Arg Asp Val Val Met Pro Ala Leu
        35                  40                  45

Gln Gly Met Asp Gly Cys Ile Gly Val Ser Leu Leu Val Asp Arg Gln
    50                  55                  60

Ser Gly Arg Cys Ile Ala Thr Ser Ala Trp Glu Thr Ala Glu Ala Met
65                  70                  75                  80

His Ala Ser Arg Glu Gln Val Thr Pro Ile Arg Asp Arg Cys Ala Glu
                85                  90                  95

Met Phe Gly Gly Thr Pro Ala Val Glu Glu Trp Glu Ile Ala Ala Met
            100                 105                 110

His Arg Asp His Arg Ser Ala Glu Gly Ala Cys Val Arg Ala Thr Trp
        115                 120                 125

Val Lys Val Pro Ala Asp Gln Val Asp Gln Gly Ile Glu Tyr Tyr Lys
    130                 135                 140

Ser Ser Val Leu Pro Gln Ile Glu Gly Leu Asp Gly Phe Cys Ser Ala
145                 150                 155                 160
```

```
Ser Leu Leu Val Asp Arg Thr Ser Gly Arg Ala Val Ser Ser Ala Thr
                165                 170                 175

Phe Asp Ser Phe Asp Ala Met Glu Arg Asn Arg Asp Gln Ser Asn Ala
            180                 185                 190

Leu Lys Ala Thr Ser Leu Arg Glu Ala Gly Gly Glu Glu Leu Asp Glu
        195                 200                 205

Cys Glu Phe Glu Leu Ala Leu Ala His Leu Arg Val Pro Glu Leu Val
    210                 215                 220


<210> SEQ ID NO 63
<211> LENGTH: 369
<212> TYPE: DNA
<213> ORGANISM: Mycobacterium tuberculosis

<400> SEQUENCE: 63

ttggccgggt cggtctcggc cgccgcagga atcggttggg tcggtttgaa cgtgacagag     60

acgaacagag accagtgcta tcgcgtcgaa cggacgaccg ttgacgcttt gacacatccc    120

gagtatcgag tacatactcg aggcgtgcag cgggtcaggg tcacgaggaa cgcccggaag    180

caccgcgtgt ccaagcaccg catcgtcgcc gctatgcgcc actgcggtgt tccggtcatt    240

caggaagatg gctcgctgta ctaccagggc cgcgatacgt cgggccgtct taccgaggtc    300

gtcgccgtcg aagccgacga cggtgacctg atcatcactc acgcaatgcc gaaggagtgg    360

aagcgatga                                                            369


<210> SEQ ID NO 64
<211> LENGTH: 122
<212> TYPE: PRT
<213> ORGANISM: Mycobacterium tuberculosis

<400> SEQUENCE: 64

Leu Ala Gly Ser Val Ser Ala Ala Ala Gly Ile Gly Trp Val Gly Leu
1               5                   10                  15

Asn Val Thr Glu Thr Asn Arg Asp Gln Cys Tyr Arg Val Glu Arg Thr
            20                  25                  30

Thr Val Asp Ala Leu Thr His Pro Glu Tyr Arg Val His Thr Arg Gly
        35                  40                  45

Val Gln Arg Val Arg Val Thr Arg Asn Ala Arg Lys His Arg Val Ser
    50                  55                  60

Lys His Arg Ile Val Ala Ala Met Arg His Cys Gly Val Pro Val Ile
65                  70                  75                  80

Gln Glu Asp Gly Ser Leu Tyr Tyr Gln Gly Arg Asp Thr Ser Gly Arg
                85                  90                  95

Leu Thr Glu Val Val Ala Val Glu Ala Asp Asp Gly Asp Leu Ile Ile
            100                 105                 110

Thr His Ala Met Pro Lys Glu Trp Lys Arg
        115                 120


<210> SEQ ID NO 65
<211> LENGTH: 1104
<212> TYPE: DNA
<213> ORGANISM: Mycobacterium tuberculosis

<400> SEQUENCE: 65

atgggggagg gttctcggag gccatctggg atgttgatgt ctgtcgatct tgagccggtg     60

caactcgtcg gcccggacgg tacgccgacg gccgaacgcc gctaccaccg tgaccttcct    120

gaggaaacgc tgcgttggct ctacgagatg atggtggtca cccgcgagct ggataccgaa    180
```

```
ttcgtcaatc tgcagcgcca gggggagctg gcgttgtaca cgccctgtcg cgggcaggaa    240

gccgcgcagg tgggtgcggc ggcttgccta cgcaaaaccg actggttgtt cccccaatac    300

cgagaattgg gcgtctacct agtgcgtggc atcccgcctg gacatgttgg ggtcgcgtgg    360

cgtggaacct ggcacggcgg gctgcaattc accacgaagt gctgtgcacc gatgtcggtt    420

cccatcggca cccagacctt gcacgcggtg ggcgcggcga tggccgcgca acgcctggac    480

gaggactccg tgacggtggc ctttctgggc gacggcgcca ccagcgaggg cgacgtacat    540

gaggcgctca atttcgcggc ggtgttcacc acaccgtgcg tgttctacgt gcagaacaac    600

cagtgggcaa tctcgatgcc ggtatccagg cagaccgccg caccatctat cgcgcacaag    660

gcgattggct acgggatgcc aggcatccgg gtggacggca acgacgtgct ggcatgctat    720

gcggtgatgg ccgaagctgc cgctcgggct cgggccggcg acggtccaac gctgatcgag    780

gcggtcactt accgtcttgg tccgcacacc accgccgatg atccaacccg gtaccgcagc    840

caggaggagg tggaccgctg ggcgacgctg gacccgattc cgcgctatcg cacttactta    900

caagatcagg gcctgtggtc gcaacgcctc gaggaacagg tgacggctcg ggcaaaacac    960

gtgcggtccg agctacgcga cgcggtcttt gatgcgcctg acttcgacgt cgatgaggtg   1020

ttcaccacgg tgtacgccga aatcacaccc gggttgcagg cgcagcgcga acagctgcgt   1080

gccgaactgg cgcggactga ctga                                          1104


<210> SEQ ID NO 66
<211> LENGTH: 367
<212> TYPE: PRT
<213> ORGANISM: Mycobacterium tuberculosis

<400> SEQUENCE: 66

Met Gly Glu Gly Ser Arg Arg Pro Ser Gly Met Leu Met Ser Val Asp
1               5                   10                  15

Leu Glu Pro Val Gln Leu Val Gly Pro Asp Gly Thr Pro Thr Ala Glu
            20                  25                  30

Arg Arg Tyr His Arg Asp Leu Pro Glu Glu Thr Leu Arg Trp Leu Tyr
        35                  40                  45

Glu Met Met Val Val Thr Arg Glu Leu Asp Thr Glu Phe Val Asn Leu
    50                  55                  60

Gln Arg Gln Gly Glu Leu Ala Leu Tyr Thr Pro Cys Arg Gly Gln Glu
65                  70                  75                  80

Ala Ala Gln Val Gly Ala Ala Ala Cys Leu Arg Lys Thr Asp Trp Leu
                85                  90                  95

Phe Pro Gln Tyr Arg Glu Leu Gly Val Tyr Leu Val Arg Gly Ile Pro
            100                 105                 110

Pro Gly His Val Gly Val Ala Trp Arg Gly Thr Trp His Gly Gly Leu
        115                 120                 125

Gln Phe Thr Thr Lys Cys Cys Ala Pro Met Ser Val Pro Ile Gly Thr
    130                 135                 140

Gln Thr Leu His Ala Val Gly Ala Ala Met Ala Ala Gln Arg Leu Asp
145                 150                 155                 160

Glu Asp Ser Val Thr Val Ala Phe Leu Gly Asp Gly Ala Thr Ser Glu
                165                 170                 175

Gly Asp Val His Glu Ala Leu Asn Phe Ala Ala Val Phe Thr Thr Pro
            180                 185                 190

Cys Val Phe Tyr Val Gln Asn Asn Gln Trp Ala Ile Ser Met Pro Val
        195                 200                 205

Ser Arg Gln Thr Ala Ala Pro Ser Ile Ala His Lys Ala Ile Gly Tyr
```

```
    210                 215                 220

Gly Met Pro Gly Ile Arg Val Asp Gly Asn Asp Val Leu Ala Cys Tyr
225                 230                 235                 240

Ala Val Met Ala Glu Ala Ala Ala Arg Ala Arg Ala Gly Asp Gly Pro
                245                 250                 255

Thr Leu Ile Glu Ala Val Thr Tyr Arg Leu Gly Pro His Thr Thr Ala
            260                 265                 270

Asp Asp Pro Thr Arg Tyr Arg Ser Gln Glu Glu Val Asp Arg Trp Ala
        275                 280                 285

Thr Leu Asp Pro Ile Pro Arg Tyr Arg Thr Tyr Leu Gln Asp Gln Gly
    290                 295                 300

Leu Trp Ser Gln Arg Leu Glu Glu Gln Val Thr Ala Arg Ala Lys His
305                 310                 315                 320

Val Arg Ser Glu Leu Arg Asp Ala Val Phe Asp Ala Pro Asp Phe Asp
                325                 330                 335

Val Asp Glu Val Phe Thr Thr Val Tyr Ala Glu Ile Thr Pro Gly Leu
            340                 345                 350

Gln Ala Gln Arg Glu Gln Leu Arg Ala Glu Leu Ala Arg Thr Asp
        355                 360                 365


<210> SEQ ID NO 67
<211> LENGTH: 1740
<212> TYPE: DNA
<213> ORGANISM: Mycobacterium tuberculosis

<400> SEQUENCE: 67

atgactacgg cgatacgccg ggcggccggg agcagctact tccgaaaccc ctggcctgcg     60

ctgtgggcga tgatggttgg cttcttcatg atcatgctcg actccaccgt cgtagccatc    120

gcgaatccga ccatcatggc ccagctacgc atcggttacg ccaccgtggt ttgggtgacc    180

agcgcctatc tgctggccta cgcggtgcca atgctggtgg ccggccggct tggcgaccgg    240

ttcggcccga agaatctcta cctgattggc ctgggggtat tcaccgttgc gtcgctgggg    300

tgcggtctgt cgagcggtgc cggcatgctg attgccgctc gagtggtgca aggcgtcggc    360

gccggattgc ttaccccgca gacgctgtcg acgataacgc ggatcttccc ggctcatcgc    420

cgcggtgtcg cgctgggcgc atggggcacc gtcgccagtg tcgccagcct ggtgggaccg    480

ttggccggcg gcgcgctggt cgacagcatg ggtgggagt ggattttctt cgtcaacgtt    540

cccgtcggcg tcatcggcct gatcctggcg gcctatctga ttccggcact accccaccac    600

ccgcatcggt tcgattggtt cggcgtcgga ttgtctggtg cgggaatgtt tctgattgtc    660

ttcggactac agcagggcca gtccgccaat tggcagcctt ggatttgggc ggtgatcgtc    720

ggcggtatcg ggtttatgtc gctgttcgtt tactggcagg cgcggaacgc ccgcgagccg    780

ctgatcccac tggaggtctt caacgaccgg aacttcagct tgtccaacct caggatagcg    840

atcatcgcct tcgcggggac ggggatgatg ctgccggtga cgttttatgc gcaggcggtg    900

tgtgggttgt cgccgaccca cacggccgtg ctgttcgcgc cgacggcgat cgtcggtggc    960

gtgctggccc cgttcgtcgg catgatcatt gacaggtccc atccgttgtg cgtactgggt   1020

ttcggcttct cggtgctggc gatcgcaatg acatggctct tatgcgagat ggctccgggc   1080

acgcccatct ggcggctggt gttgccgttc atcgcgttag gcgttgctgg ggcgttcgtg   1140

tggtcgccgc tgaccgtcac cgcgacccgc aatctacggc cgcacctggc cggtgcgagc   1200

tcaggtgtgt tcaacgccgt ccggcagctg gggctgtgc tggggagcgc gagcatggcc   1260

gcgttcatga cgtcgcgcat cgccgccgag atgcccggtg gtgtggacgc ccttaccggt   1320
```

```
cccgccgggc aggacgctac cgtgttgcag ctgcccgagt tcgtgcgcga acccttcgcg   1380

gccgcgatgt cgcaatcgat gctgttgccc gccttcgtcg ccctattcgg gatcgttgcc   1440

gcgttgttcc tggttgactt caccggtgct gcggttgcca aagagccgtt gcccgaatcc   1500

gatggcgacg ctgacgacga cgactatgtc gagtacatcc ttcgtcggga accggaagag   1560

gattgcgaca cccagccgct gcgggcgtcg cgcccggcag cggccgcagc gtcacgcagc   1620

ggtgctgggg gtccgctggc ggtcagctgg tcgacgtcag cccaaggaat gccccaggt   1680

ccaccaggcc gtcgggcgtg gcaggcagat actgagtcaa cagctccgag cgcactataa   1740


<210> SEQ ID NO 68
<211> LENGTH: 579
<212> TYPE: PRT
<213> ORGANISM: Mycobacterium tuberculosis

<400> SEQUENCE: 68

Met Thr Thr Ala Ile Arg Arg Ala Ala Gly Ser Ser Tyr Phe Arg Asn
1               5                   10                  15

Pro Trp Pro Ala Leu Trp Ala Met Met Val Gly Phe Phe Met Ile Met
            20                  25                  30

Leu Asp Ser Thr Val Val Ala Ile Ala Asn Pro Thr Ile Met Ala Gln
        35                  40                  45

Leu Arg Ile Gly Tyr Ala Thr Val Val Trp Val Thr Ser Ala Tyr Leu
    50                  55                  60

Leu Ala Tyr Ala Val Pro Met Leu Val Ala Gly Arg Leu Gly Asp Arg
65                  70                  75                  80

Phe Gly Pro Lys Asn Leu Tyr Leu Ile Gly Leu Gly Val Phe Thr Val
                85                  90                  95

Ala Ser Leu Gly Cys Gly Leu Ser Ser Gly Ala Gly Met Leu Ile Ala
            100                 105                 110

Ala Arg Val Val Gln Gly Val Gly Ala Gly Leu Leu Thr Pro Gln Thr
        115                 120                 125

Leu Ser Thr Ile Thr Arg Ile Phe Pro Ala His Arg Arg Gly Val Ala
    130                 135                 140

Leu Gly Ala Trp Gly Thr Val Ala Ser Val Ala Ser Leu Val Gly Pro
145                 150                 155                 160

Leu Ala Gly Gly Ala Leu Val Asp Ser Met Gly Trp Glu Trp Ile Phe
                165                 170                 175

Phe Val Asn Val Pro Val Gly Val Ile Gly Leu Ile Leu Ala Ala Tyr
            180                 185                 190

Leu Ile Pro Ala Leu Pro His His Pro His Arg Phe Asp Trp Phe Gly
        195                 200                 205

Val Gly Leu Ser Gly Ala Gly Met Phe Leu Ile Val Phe Gly Leu Gln
    210                 215                 220

Gln Gly Gln Ser Ala Asn Trp Gln Pro Trp Ile Trp Ala Val Ile Val
225                 230                 235                 240

Gly Gly Ile Gly Phe Met Ser Leu Phe Val Tyr Trp Gln Ala Arg Asn
                245                 250                 255

Ala Arg Glu Pro Leu Ile Pro Leu Glu Val Phe Asn Asp Arg Asn Phe
            260                 265                 270

Ser Leu Ser Asn Leu Arg Ile Ala Ile Ile Ala Phe Ala Gly Thr Gly
        275                 280                 285

Met Met Leu Pro Val Thr Phe Tyr Ala Gln Ala Val Cys Gly Leu Ser
    290                 295                 300
```

```
Pro Thr His Thr Ala Val Leu Phe Ala Pro Thr Ala Ile Val Gly Gly
305                 310                 315                 320

Val Leu Ala Pro Phe Val Gly Met Ile Ile Asp Arg Ser His Pro Leu
                325                 330                 335

Cys Val Leu Gly Phe Gly Phe Ser Val Leu Ala Ile Ala Met Thr Trp
            340                 345                 350

Leu Leu Cys Glu Met Ala Pro Gly Thr Pro Ile Trp Arg Leu Val Leu
        355                 360                 365

Pro Phe Ile Ala Leu Gly Val Ala Gly Ala Phe Val Trp Ser Pro Leu
    370                 375                 380

Thr Val Thr Ala Thr Arg Asn Leu Arg Pro His Leu Ala Gly Ala Ser
385                 390                 395                 400

Ser Gly Val Phe Asn Ala Val Arg Gln Leu Gly Ala Val Leu Gly Ser
                405                 410                 415

Ala Ser Met Ala Ala Phe Met Thr Ser Arg Ile Ala Ala Glu Met Pro
            420                 425                 430

Gly Gly Val Asp Ala Leu Thr Gly Pro Ala Gly Gln Asp Ala Thr Val
        435                 440                 445

Leu Gln Leu Pro Glu Phe Val Arg Glu Pro Phe Ala Ala Ala Met Ser
    450                 455                 460

Gln Ser Met Leu Leu Pro Ala Phe Val Ala Leu Phe Gly Ile Val Ala
465                 470                 475                 480

Ala Leu Phe Leu Val Asp Phe Thr Gly Ala Ala Val Ala Lys Glu Pro
                485                 490                 495

Leu Pro Glu Ser Asp Gly Asp Ala Asp Asp Asp Asp Tyr Val Glu Tyr
            500                 505                 510

Ile Leu Arg Arg Glu Pro Glu Glu Asp Cys Asp Thr Gln Pro Leu Arg
        515                 520                 525

Ala Ser Arg Pro Ala Ala Ala Ala Ala Ser Arg Ser Gly Ala Gly Gly
    530                 535                 540

Pro Leu Ala Val Ser Trp Ser Thr Ser Ala Gln Gly Met Pro Pro Gly
545                 550                 555                 560

Pro Pro Gly Arg Arg Ala Trp Gln Ala Asp Thr Glu Ser Thr Ala Pro
                565                 570                 575

Ser Ala Leu
```

<210> SEQ ID NO 69
<211> LENGTH: 1752
<212> TYPE: DNA
<213> ORGANISM: Mycobacterium tuberculosis

<400> SEQUENCE: 69

```
atgaccgccc aacacaacat cgtggttatc ggcggcggtg gtgcgggtct gcgcgccgcg      60

attgcgatag ccgaaaccaa tccgcacctg gatgtggcga tcgtttccaa ggtgtacccg     120

atgcgcagcc acaccgtctc ggctgagggc ggcgccgcgg cggtgaccgg tgacgacgac     180

agcctcgatg aacacgcgca cgacacggta tccggtggcg actggctgtg tgaccaagat     240

gcggtcgagg ctttcgtggc cgaggcgccc aaagagttgg tgcagctcga gcattggggc     300

tgtccgtgga gccgtaaacc agacgggcgc gttgccgttc gcccgttcgg cgggatgaag     360

aagctgcgca cctggtttgc cgccgacaag acgggatttc acctcctgca cacgttgttt     420

caacggctgc tcacctattc cgacgtcatg cgctatgacg agtggttcgc tacgacgctg     480

ctggtcgacg acggcagggt atgtggtctg gtcgctatcg agttggcgac cgggcgcatc     540

gagacgatcc ttgccgacgc ggtgattctg tgcaccggcg gatgcgggcg ggtatttcca     600
```

```
ttcaccacca acgcgaacat caagaccggc gacggcatgg cgctcgcatt ccgcgcgggc    660

gcgcccctaa aagacatgga attcgtccaa taccacccca ccggactgcc gttcaccggg    720

atcttgatca ccgaggccgc acgagctgaa ggcggctggc tgctcaacaa agacggctac    780

cgctacctcc aggattacga cctcggcaag cccacgcccg agcccaggct gcgcagtatg    840

gagctcgggc ccagggaccg actgtcgcag gccttcgtac acgagcacaa caaaggaagg    900

acggtcgaca ccccgtacgg ccccgtcgtc tatctagacc tgcggcacct gggggcggac    960

ctgatcgatg caaagttgcc gttcgtacgt gagctgtgcc gcgactacca gcacatcgac   1020

cccgtggtcg aattggtccc ggtacgaccg gtagtgcact acatgatggg tggcgttcac   1080

accgatatca acggcgccac aacgcttccc gggctatatg ccgcaggtga aacagcctgc   1140

gtgagcatta atggcgccaa ccgcctgggg tcgaactcgc tgcccgagct gctggtgttc   1200

ggggctcgag cgggccgtgc cgccgcggat tacgcagcgc gccaccaaaa gtcggaccgt   1260

ggcccgtcgt cggcagtgcg ggctcaggcc cgcaccgagg ctctacggct agagcgtgag   1320

ctcagccgcc atggccaggg aggcgaacga atcgcggata ttcgggcgga catgcaggcc   1380

accttggaaa gcgccgcggg tatttatcgt gacggaccca ccctcaccaa agcggtcgag   1440

gagattcggg tgctgcagga acgattcgcc acggcgggca tcgacgatca cagccgcaca   1500

ttcaacaccg agctgactgc gctgctcgag ttgtcgggga tgctcgacgt tgcactggcg   1560

atcgtcgaat cgggtttgcg ccgagaagaa tcccgtggcg cacaccagcg aaccgacttt   1620

ccgaaccggg acgacgagca tttcttggcg cacaccttgg ttcatagaga aagcgacgga   1680

acgctgcggg tcggctacct tccggtcact atcactcgct ggccaccggg cgaacgcgtg   1740

tatgggaggt aa                                                       1752
```

```
<210> SEQ ID NO 70
<211> LENGTH: 583
<212> TYPE: PRT
<213> ORGANISM: Mycobacterium tuberculosis

<400> SEQUENCE: 70

Met Thr Ala Gln His Asn Ile Val Val Ile Gly Gly Gly Gly Ala Gly
1               5                   10                  15

Leu Arg Ala Ala Ile Ala Ile Ala Glu Thr Asn Pro His Leu Asp Val
            20                  25                  30

Ala Ile Val Ser Lys Val Tyr Pro Met Arg Ser His Thr Val Ser Ala
        35                  40                  45

Glu Gly Gly Ala Ala Ala Val Thr Gly Asp Asp Asp Ser Leu Asp Glu
    50                  55                  60

His Ala His Asp Thr Val Ser Gly Gly Asp Trp Leu Cys Asp Gln Asp
65                  70                  75                  80

Ala Val Glu Ala Phe Val Ala Glu Ala Pro Lys Glu Leu Val Gln Leu
                85                  90                  95

Glu His Trp Gly Cys Pro Trp Ser Arg Lys Pro Asp Gly Arg Val Ala
            100                 105                 110

Val Arg Pro Phe Gly Gly Met Lys Lys Leu Arg Thr Trp Phe Ala Ala
        115                 120                 125

Asp Lys Thr Gly Phe His Leu Leu His Thr Leu Phe Gln Arg Leu Leu
    130                 135                 140

Thr Tyr Ser Asp Val Met Arg Tyr Asp Glu Trp Phe Ala Thr Thr Leu
145                 150                 155                 160

Leu Val Asp Asp Gly Arg Val Cys Gly Leu Val Ala Ile Glu Leu Ala
```

```
                165                 170                 175

Thr Gly Arg Ile Glu Thr Ile Leu Ala Asp Ala Val Ile Leu Cys Thr
            180                 185                 190

Gly Gly Cys Gly Arg Val Phe Pro Phe Thr Thr Asn Ala Asn Ile Lys
        195                 200                 205

Thr Gly Asp Gly Met Ala Leu Ala Phe Arg Ala Gly Ala Pro Leu Lys
    210                 215                 220

Asp Met Glu Phe Val Gln Tyr His Pro Thr Gly Leu Pro Phe Thr Gly
225                 230                 235                 240

Ile Leu Ile Thr Glu Ala Ala Arg Ala Glu Gly Gly Trp Leu Leu Asn
                245                 250                 255

Lys Asp Gly Tyr Arg Tyr Leu Gln Asp Tyr Asp Leu Gly Lys Pro Thr
            260                 265                 270

Pro Glu Pro Arg Leu Arg Ser Met Glu Leu Gly Pro Arg Asp Arg Leu
        275                 280                 285

Ser Gln Ala Phe Val His Glu His Asn Lys Gly Arg Thr Val Asp Thr
    290                 295                 300

Pro Tyr Gly Pro Val Val Tyr Leu Asp Leu Arg His Leu Gly Ala Asp
305                 310                 315                 320

Leu Ile Asp Ala Lys Leu Pro Phe Val Arg Glu Leu Cys Arg Asp Tyr
                325                 330                 335

Gln His Ile Asp Pro Val Val Glu Leu Val Pro Val Arg Pro Val Val
            340                 345                 350

His Tyr Met Met Gly Gly Val His Thr Asp Ile Asn Gly Ala Thr Thr
        355                 360                 365

Leu Pro Gly Leu Tyr Ala Ala Gly Glu Thr Ala Cys Val Ser Ile Asn
    370                 375                 380

Gly Ala Asn Arg Leu Gly Ser Asn Ser Leu Pro Glu Leu Leu Val Phe
385                 390                 395                 400

Gly Ala Arg Ala Gly Arg Ala Ala Ala Asp Tyr Ala Ala Arg His Gln
                405                 410                 415

Lys Ser Asp Arg Gly Pro Ser Ser Ala Val Arg Ala Gln Ala Arg Thr
            420                 425                 430

Glu Ala Leu Arg Leu Glu Arg Glu Leu Ser Arg His Gly Gln Gly Gly
        435                 440                 445

Glu Arg Ile Ala Asp Ile Arg Ala Asp Met Gln Ala Thr Leu Glu Ser
    450                 455                 460

Ala Ala Gly Ile Tyr Arg Asp Gly Pro Thr Leu Thr Lys Ala Val Glu
465                 470                 475                 480

Glu Ile Arg Val Leu Gln Glu Arg Phe Ala Thr Ala Gly Ile Asp Asp
                485                 490                 495

His Ser Arg Thr Phe Asn Thr Glu Leu Thr Ala Leu Leu Glu Leu Ser
            500                 505                 510

Gly Met Leu Asp Val Ala Leu Ala Ile Val Glu Ser Gly Leu Arg Arg
        515                 520                 525

Glu Glu Ser Arg Gly Ala His Gln Arg Thr Asp Phe Pro Asn Arg Asp
    530                 535                 540

Asp Glu His Phe Leu Ala His Thr Leu Val His Arg Glu Ser Asp Gly
545                 550                 555                 560

Thr Leu Arg Val Gly Tyr Leu Pro Val Thr Ile Thr Arg Trp Pro Pro
                565                 570                 575

Gly Glu Arg Val Tyr Gly Arg
            580
```

<210> SEQ ID NO 71
<211> LENGTH: 228
<212> TYPE: DNA
<213> ORGANISM: Mycobacterium tuberculosis

<400> SEQUENCE: 71

```
atgaccgtaa agaggaccac gattgagctg gacgaagatc ttgtgcgggc agcccaggcc     60

gtcaccgggg aaacattgcg agcgacggtc gagcgcgcgc tgcagcagct ggtggccgcg    120

gctgccgagc aggccgccgc gcgccggcgg cggatcgtcg accatctcgc gcacgccggc    180

actcacgtgg acgcagacgt gctgctctcc gagcaggcgt ggcgatga                 228
```

<210> SEQ ID NO 72
<211> LENGTH: 75
<212> TYPE: PRT
<213> ORGANISM: Mycobacterium tuberculosis

<400> SEQUENCE: 72

```
Met Thr Val Lys Arg Thr Thr Ile Glu Leu Asp Glu Asp Leu Val Arg
1               5                   10                  15

Ala Ala Gln Ala Val Thr Gly Glu Thr Leu Arg Ala Thr Val Glu Arg
            20                  25                  30

Ala Leu Gln Gln Leu Val Ala Ala Ala Ala Glu Gln Ala Ala Ala Arg
        35                  40                  45

Arg Arg Arg Ile Val Asp His Leu Ala His Ala Gly Thr His Val Asp
    50                  55                  60

Ala Asp Val Leu Leu Ser Glu Gln Ala Trp Arg
65                  70                  75
```

<210> SEQ ID NO 73
<211> LENGTH: 1407
<212> TYPE: DNA
<213> ORGANISM: Mycobacterium tuberculosis

<400> SEQUENCE: 73

```
atggatttcg gattgcagcc accggagatc acctccgggg agatgtacct aggtccgggc     60

gccggtccga tgttggctgc ggcagtggcc tgggatgggt tggcggccga attgcagtcc    120

atggcggcct cctacgcctc gatcgtcgag ggcatggcga gtgagtcatg gttgggtccg    180

tcgtcggccg gtatggccgc tgcggccgca ccatatgtga cctggatgtc gggtacctcg    240

gcacaggcca aggcggccgc tgaccaggcc agagccgcgg tggtcgccta cgaaaccgcg    300

ttcgcggcgg tggtgccacc gccgcagatt gcggccaacc gcagccagct catatcgctg    360

gtggcgacca acattttcgg acaaaacacc gccgcgatcg cagccaccga agccgaatac    420

ggcgaaatgt gggcccagga caccatggcg atgttcggct atgctagctc ctcggcgacc    480

gcctcgcggc tgaccccgtt cactgcaccg ccgcagacca ccaacccgtc cggacttgcc    540

ggccaggcgg ccgcaacggg gcaagcgacc gccctagcga gcggcaccaa tgcggtgaca    600

accgcgcttt cgagtgcagc ggcgcagttt ccgttcgaca tcatcccgac cctgctgcag    660

ggcctggcca cactcagcac ccaatacacc caactcatgg gccaactcat taacgccatc    720

ttcgggccga cgggcgcaac gacctatcag aacgtgtttg tcaccgcagc caacgtcacc    780

aagttcagca cgtgggccaa cgacgccatg agcgcgccca acctgggaat gacggagttc    840

aaggtgttct ggcaaccccc gccggcgccc gagatcccca aatcgtcgtt gggtgccgga    900

cttggcctgc ggtcagggct tagcgcgggc ctggcccacg ccgcatcggc gggtctgggt    960

caggcgaacc tggtgggaga cctgtcggta ccgcccagtt gggcctcagc taccccggcg   1020
```

```
gtcaggctag ttgccaacac attgccggcc accagcctgg ctgcggcccc cgcgacacag   1080

atcccagcaa acctgctcgg tcagatggct ctggggagca tgaccggagg tgccctcggt   1140

gccgccgccc ccgccatcta cacgggcagt ggcgcccggg cccgcgccaa tgggggaacg   1200

cccagcgctg agccggtcaa gctggaggct gtcatcgcgc agctacaaaa gcaaccggac   1260

gcagtgcgac actggaatgt cgataaggcc gatcttgatg gcctgctgga tcgattgtcg   1320

aaacagcccg gcatccacgc ggtacacgtg tcgaacggcg acaaacccaa ggttgccttg   1380

cccgatactc agttgggttc acactga                                       1407


<210> SEQ ID NO 74
<211> LENGTH: 468
<212> TYPE: PRT
<213> ORGANISM: Mycobacterium tuberculosis

<400> SEQUENCE: 74

Met Asp Phe Gly Leu Gln Pro Pro Glu Ile Thr Ser Gly Glu Met Tyr
1               5                   10                  15

Leu Gly Pro Gly Ala Gly Pro Met Leu Ala Ala Ala Val Ala Trp Asp
            20                  25                  30

Gly Leu Ala Ala Glu Leu Gln Ser Met Ala Ala Ser Tyr Ala Ser Ile
        35                  40                  45

Val Glu Gly Met Ala Ser Glu Ser Trp Leu Gly Pro Ser Ser Ala Gly
    50                  55                  60

Met Ala Ala Ala Ala Ala Pro Tyr Val Thr Trp Met Ser Gly Thr Ser
65                  70                  75                  80

Ala Gln Ala Lys Ala Ala Ala Asp Gln Ala Arg Ala Ala Val Val Ala
                85                  90                  95

Tyr Glu Thr Ala Phe Ala Ala Val Val Pro Pro Pro Gln Ile Ala Ala
            100                 105                 110

Asn Arg Ser Gln Leu Ile Ser Leu Val Ala Thr Asn Ile Phe Gly Gln
        115                 120                 125

Asn Thr Ala Ala Ile Ala Ala Thr Glu Ala Glu Tyr Gly Glu Met Trp
    130                 135                 140

Ala Gln Asp Thr Met Ala Met Phe Gly Tyr Ala Ser Ser Ser Ala Thr
145                 150                 155                 160

Ala Ser Arg Leu Thr Pro Phe Thr Ala Pro Pro Gln Thr Thr Asn Pro
                165                 170                 175

Ser Gly Leu Ala Gly Gln Ala Ala Ala Thr Gly Gln Ala Thr Ala Leu
            180                 185                 190

Ala Ser Gly Thr Asn Ala Val Thr Thr Ala Leu Ser Ser Ala Ala Ala
        195                 200                 205

Gln Phe Pro Phe Asp Ile Ile Pro Thr Leu Leu Gln Gly Leu Ala Thr
    210                 215                 220

Leu Ser Thr Gln Tyr Thr Gln Leu Met Gly Gln Leu Ile Asn Ala Ile
225                 230                 235                 240

Phe Gly Pro Thr Gly Ala Thr Thr Tyr Gln Asn Val Phe Val Thr Ala
                245                 250                 255

Ala Asn Val Thr Lys Phe Ser Thr Trp Ala Asn Asp Ala Met Ser Ala
            260                 265                 270

Pro Asn Leu Gly Met Thr Glu Phe Lys Val Phe Trp Gln Pro Pro Pro
        275                 280                 285

Ala Pro Glu Ile Pro Lys Ser Ser Leu Gly Ala Gly Leu Gly Leu Arg
    290                 295                 300
```

```
Ser Gly Leu Ser Ala Gly Leu Ala His Ala Ala Ser Ala Gly Leu Gly
305                 310                 315                 320

Gln Ala Asn Leu Val Gly Asp Leu Ser Val Pro Pro Ser Trp Ala Ser
                325                 330                 335

Ala Thr Pro Ala Val Arg Leu Val Ala Asn Thr Leu Pro Ala Thr Ser
            340                 345                 350

Leu Ala Ala Ala Pro Ala Thr Gln Ile Pro Ala Asn Leu Leu Gly Gln
        355                 360                 365

Met Ala Leu Gly Ser Met Thr Gly Gly Ala Leu Gly Ala Ala Ala Pro
    370                 375                 380

Ala Ile Tyr Thr Gly Ser Gly Ala Arg Ala Arg Ala Asn Gly Gly Thr
385                 390                 395                 400

Pro Ser Ala Glu Pro Val Lys Leu Glu Ala Val Ile Ala Gln Leu Gln
                405                 410                 415

Lys Gln Pro Asp Ala Val Arg His Trp Asn Val Asp Lys Ala Asp Leu
            420                 425                 430

Asp Gly Leu Leu Asp Arg Leu Ser Lys Gln Pro Gly Ile His Ala Val
        435                 440                 445

His Val Ser Asn Gly Asp Lys Pro Lys Val Ala Leu Pro Asp Thr Gln
    450                 455                 460

Leu Gly Ser His
465
```

<210> SEQ ID NO 75
<211> LENGTH: 477
<212> TYPE: DNA
<213> ORGANISM: Mycobacterium tuberculosis

<400> SEQUENCE: 75

```
ttgcaccgag cgggagcggc ggtgacggcc aacgtgtggt gtcgtgcggg cggcattcgg      60

atggcgccac ggccggtcat cccggtggct acgcagcagc gcctgcggcg gcaggcggat     120

cgccagagcc tgggtagtag cggcttgcca gcgttgaatt gtacgcctat caggcacaca     180

attgatgtca tggctaccaa gcctgagcgg aagaccgagc gtcttgcagc gcgcctgacc     240

cctgagcagg acgcgctgat tcgtcgtgct gccgaggccg aggggactga cctcaccaat     300

ttcacggtta cagcggcgtt ggcgcacgcg cgcgacgtgc tggccgaccg ccggctcttc     360

gtactcaccg atgccgcgtg gactgagttc ctcgccgcgc tggaccggcc cgtctcacac     420

aagcctcggt tggagaagct gttcgccgcg cggtccattt tcgacaccga ggggtga        477
```

<210> SEQ ID NO 76
<211> LENGTH: 158
<212> TYPE: PRT
<213> ORGANISM: Mycobacterium tuberculosis

<400> SEQUENCE: 76

```
Leu His Arg Ala Gly Ala Ala Val Thr Ala Asn Val Trp Cys Arg Ala
1               5                   10                  15

Gly Gly Ile Arg Met Ala Pro Arg Pro Val Ile Pro Val Ala Thr Gln
            20                  25                  30

Gln Arg Leu Arg Arg Gln Ala Asp Arg Gln Ser Leu Gly Ser Ser Gly
        35                  40                  45

Leu Pro Ala Leu Asn Cys Thr Pro Ile Arg His Thr Ile Asp Val Met
    50                  55                  60

Ala Thr Lys Pro Glu Arg Lys Thr Glu Arg Leu Ala Ala Arg Leu Thr
65                  70                  75                  80
```

```
Pro Glu Gln Asp Ala Leu Ile Arg Arg Ala Ala Glu Ala Glu Gly Thr
                85                  90                  95

Asp Leu Thr Asn Phe Thr Val Thr Ala Ala Leu Ala His Ala Arg Asp
            100                 105                 110

Val Leu Ala Asp Arg Arg Leu Phe Val Leu Thr Asp Ala Ala Trp Thr
        115                 120                 125

Glu Phe Leu Ala Ala Leu Asp Arg Pro Val Ser His Lys Pro Arg Leu
    130                 135                 140

Glu Lys Leu Phe Ala Ala Arg Ser Ile Phe Asp Thr Glu Gly
145                 150                 155


<210> SEQ ID NO 77
<211> LENGTH: 477
<212> TYPE: DNA
<213> ORGANISM: Mycobacterium tuberculosis

<400> SEQUENCE: 77

atgactacca cgatcccgac gtcaaaatcg gcttgcagcg tcacgacgcg gcccggaaat      60

gccgccgttg actacggtgg cgctcagatt cgggcctacc tgcatcacct ggcgacagtg     120

gtgaccatcc gaggcgagat cgacgccgcc aatgtcgagc agatcagcga gcacgtccgg     180

cgtttcagcc tcggaacaaa tccgatggtg ctcgacctga gcgagttgag tcacttcagt     240

ggggccggca tctcgctctt gtgcatcctc gatgaggact gccgagccgc cggcgtccag     300

tgggcattag tcgcgagccc cgcagtagtc gaacagctag gtggccgctg tgaccagggc     360

gagcatgaat ccatgttccc gatggcgcgc tcggtgcata aagcgctcca cgacctggct     420

gacgccatcg accgccgccg tcagctggtg ctaccgctaa tcagcaggtc agcctaa        477


<210> SEQ ID NO 78
<211> LENGTH: 158
<212> TYPE: PRT
<213> ORGANISM: Mycobacterium tuberculosis

<400> SEQUENCE: 78

Met Thr Thr Thr Ile Pro Thr Ser Lys Ser Ala Cys Ser Val Thr Thr
1               5                   10                  15

Arg Pro Gly Asn Ala Ala Val Asp Tyr Gly Gly Ala Gln Ile Arg Ala
            20                  25                  30

Tyr Leu His His Leu Ala Thr Val Val Thr Ile Arg Gly Glu Ile Asp
        35                  40                  45

Ala Ala Asn Val Glu Gln Ile Ser Glu His Val Arg Arg Phe Ser Leu
    50                  55                  60

Gly Thr Asn Pro Met Val Leu Asp Leu Ser Glu Leu Ser His Phe Ser
65                  70                  75                  80

Gly Ala Gly Ile Ser Leu Leu Cys Ile Leu Asp Glu Asp Cys Arg Ala
                85                  90                  95

Ala Gly Val Gln Trp Ala Leu Val Ala Ser Pro Ala Val Val Glu Gln
            100                 105                 110

Leu Gly Gly Arg Cys Asp Gln Gly Glu His Glu Ser Met Phe Pro Met
        115                 120                 125

Ala Arg Ser Val His Lys Ala Leu His Asp Leu Ala Asp Ala Ile Asp
    130                 135                 140

Arg Arg Arg Gln Leu Val Leu Pro Leu Ile Ser Arg Ser Ala
145                 150                 155


<210> SEQ ID NO 79
<211> LENGTH: 339
```

<212> TYPE: DNA
<213> ORGANISM: Mycobacterium tuberculosis

<400> SEQUENCE: 79

```
atggcggctt tggtgcgtga ggtcgttggt gacgtgctgc gcggagcgcg gatgtcgcag      60

ggtcggacgc tgcgcgaggt gtccgattcg gcgcgggtga gcctcgggta tctgtcggag     120

atcgagcgcg gtcgcaagga gccttccagc gagctgctca gtgcgatttg tacggctctg     180

cagctcccgt tgtcggtggt gctcatcgat gcgggcgagc ggatggcgcg tcaagagcgc     240

cttgcccgcg ccaccccggc tggcagagca accggcgcca ccattgacgc cagcaccaag     300

gtcgtcattg cgccggtggt gtcgctggcg gtggcctaa                            339
```

<210> SEQ ID NO 80
<211> LENGTH: 112
<212> TYPE: PRT
<213> ORGANISM: Mycobacterium tuberculosis

<400> SEQUENCE: 80

```
Met Ala Ala Leu Val Arg Glu Val Val Gly Asp Val Leu Arg Gly Ala
1               5                   10                  15

Arg Met Ser Gln Gly Arg Thr Leu Arg Glu Val Ser Asp Ser Ala Arg
            20                  25                  30

Val Ser Leu Gly Tyr Leu Ser Glu Ile Glu Arg Gly Arg Lys Glu Pro
        35                  40                  45

Ser Ser Glu Leu Leu Ser Ala Ile Cys Thr Ala Leu Gln Leu Pro Leu
    50                  55                  60

Ser Val Val Leu Ile Asp Ala Gly Glu Arg Met Ala Arg Gln Glu Arg
65                  70                  75                  80

Leu Ala Arg Ala Thr Pro Ala Gly Arg Ala Thr Gly Ala Thr Ile Asp
                85                  90                  95

Ala Ser Thr Lys Val Val Ile Ala Pro Val Val Ser Leu Ala Val Ala
            100                 105                 110
```

<210> SEQ ID NO 81
<211> LENGTH: 858
<212> TYPE: DNA
<213> ORGANISM: Mycobacterium tuberculosis

<400> SEQUENCE: 81

```
gtgccccacc gctgcgcggc gcaagtcgtc gccgggtacc gttcaacggt gagtttggtc      60

ctcgtcgaac acccgcggcc cgagatcgcg cagattaccc tcaaccggcc ggagcggatg     120

aactccatgg cattcgatgt catggtgccg ctcaaagagg ccttagcgca ggtcagctac     180

gacaactcgg tgcgggtggt ggtgctgacc ggcgcgggtc gagggttttc tccgggtgcg     240

gatcacaagt cggcgggggt ggtgccgcac gtcgagaact tgactcggcc cacctacgcg     300

ctgcgttcga tggagctcct cgatgacgtc atcttaatgc tgcgacggct gcaccagccg     360

gtgatcgccg cggtcaacgg ccccgccatc ggtggtgggc tgtgcctggc actggctgca     420

gacattcggg tggcctcgag tagcgcctac ttccgggccg ccggtatcaa caacgggctg     480

accgccagcg aattggggct gagctacctg ttgcccaggg ccattggatc ctcacgtgcg     540

ttcgagatca tgttgaccgg tcgcgacgtc agcgccgagg aagccgagag gatcgggctg     600

gtatcccgtc aggtacccga tgaacagctg ctagatgcct gctacgcgat cgccgcacgg     660

atggcgggat tctcgcggcc gggaattgag ttgaccaaac gtacgctgtg gagtggactg     720

gacgccgcca gtctggaggc gcacatgcag gccgagggct tggggcagct cttcgtccgg     780
```

```
ctgctcaccg ccaacttcga agaagcggtt gccgcacggg ccgagcagcg ggcgccggtg    840

ttcaccgatg acacgtaa                                                   858


<210> SEQ ID NO 82
<211> LENGTH: 285
<212> TYPE: PRT
<213> ORGANISM: Mycobacterium tuberculosis

<400> SEQUENCE: 82

Val Pro His Arg Cys Ala Ala Gln Val Val Ala Gly Tyr Arg Ser Thr
1               5                   10                  15

Val Ser Leu Val Leu Val Glu His Pro Arg Pro Glu Ile Ala Gln Ile
            20                  25                  30

Thr Leu Asn Arg Pro Glu Arg Met Asn Ser Met Ala Phe Asp Val Met
        35                  40                  45

Val Pro Leu Lys Glu Ala Leu Ala Gln Val Ser Tyr Asp Asn Ser Val
    50                  55                  60

Arg Val Val Val Leu Thr Gly Ala Gly Arg Gly Phe Ser Pro Gly Ala
65                  70                  75                  80

Asp His Lys Ser Ala Gly Val Val Pro His Val Glu Asn Leu Thr Arg
                85                  90                  95

Pro Thr Tyr Ala Leu Arg Ser Met Glu Leu Leu Asp Asp Val Ile Leu
            100                 105                 110

Met Leu Arg Arg Leu His Gln Pro Val Ile Ala Ala Val Asn Gly Pro
        115                 120                 125

Ala Ile Gly Gly Gly Leu Cys Leu Ala Leu Ala Ala Asp Ile Arg Val
    130                 135                 140

Ala Ser Ser Ser Ala Tyr Phe Arg Ala Ala Gly Ile Asn Asn Gly Leu
145                 150                 155                 160

Thr Ala Ser Glu Leu Gly Leu Ser Tyr Leu Leu Pro Arg Ala Ile Gly
                165                 170                 175

Ser Ser Arg Ala Phe Glu Ile Met Leu Thr Gly Arg Asp Val Ser Ala
            180                 185                 190

Glu Glu Ala Glu Arg Ile Gly Leu Val Ser Arg Gln Val Pro Asp Glu
        195                 200                 205

Gln Leu Leu Asp Ala Cys Tyr Ala Ile Ala Ala Arg Met Ala Gly Phe
    210                 215                 220

Ser Arg Pro Gly Ile Glu Leu Thr Lys Arg Thr Leu Trp Ser Gly Leu
225                 230                 235                 240

Asp Ala Ala Ser Leu Glu Ala His Met Gln Ala Glu Gly Leu Gly Gln
                245                 250                 255

Leu Phe Val Arg Leu Leu Thr Ala Asn Phe Glu Glu Ala Val Ala Ala
            260                 265                 270

Arg Ala Glu Gln Arg Ala Pro Val Phe Thr Asp Asp Thr
        275                 280                 285


<210> SEQ ID NO 83
<211> LENGTH: 1062
<212> TYPE: DNA
<213> ORGANISM: Mycobacterium tuberculosis

<400> SEQUENCE: 83

gtgagcgtca tcgcaggtgt gttcggcgcg ttgccgccgt atcgctattc acaacgcgag     60

ctcaccgact cgtttgtcag catcccggat ttcgagggct acgaagacat cgttcgccag    120

ctgcacgcca gcgccaaagt caacagccgc cacctggtct tgccgctgga gaaatacccg    180
```

```
aagctgaccg acttcggcga ggcgaacaag attttcatcg aaaaagccgt ggacttgggc    240

gtgcaagccc tggcgggggc actcgacgag tccggtctgc gacccgagga tctcgacgtg    300

ttgatcaccg ccacggtcac cggactggcg gtgccgtcgc tggatgcccg gatcgccggg    360

cggctggggc tgcgcgccga tgtccggagg gtgccgctgt tcgggctggg ctgcgtggcc    420

ggggcggccg gggtcgcccg gctgcacgac tacctgcgcg gggccccgga cggcgttgcc    480

gcgttggtct cggtcgagct gtgttcactc acgtatccgg gatacaagcc gacgctgccg    540

ggccttgtcg gcagtgcgtt gtttgctgac ggcgccgcgg cggtggtggc cgcaggtgtg    600

aagcgcgccc aggacatcgg cgccgacggg ccggacatcc tggattcgcg cagccatctg    660

taccccgact cgctgcgcac catgggatac gacgtcggct cggccgggtt cgagctcgtc    720

ctatcacggg acttggcggc cgtggtcgag cagtatctgg gcaatgacgt caccaccttc    780

ctggcttcgc acggcctgag caccaccgac gtcggcgcct gggtcaccca tcccggggga    840

cccaagatca tcaacgccat caccgagacc ctcgacctgt cgccgcaggc tctcgagctg    900

acgtggcgct cgttgggcga aatcgggaat ctgtcgtcag cgtcggtgct gcatgtgctg    960

cgtgacacca tcgccaaacc gccccccagc ggaagtcccg ggttgatgat cgccatgggc   1020

ccaggcttct gttccgaact cgtgttgctg cgctggcact ga                      1062
```

<210> SEQ ID NO 84
<211> LENGTH: 353
<212> TYPE: PRT
<213> ORGANISM: Mycobacterium tuberculosis

<400> SEQUENCE: 84

```
Val Ser Val Ile Ala Gly Val Phe Gly Ala Leu Pro Pro Tyr Arg Tyr
1               5                   10                  15

Ser Gln Arg Glu Leu Thr Asp Ser Phe Val Ser Ile Pro Asp Phe Glu
            20                  25                  30

Gly Tyr Glu Asp Ile Val Arg Gln Leu His Ala Ser Ala Lys Val Asn
        35                  40                  45

Ser Arg His Leu Val Leu Pro Leu Glu Lys Tyr Pro Lys Leu Thr Asp
    50                  55                  60

Phe Gly Glu Ala Asn Lys Ile Phe Ile Glu Lys Ala Val Asp Leu Gly
65                  70                  75                  80

Val Gln Ala Leu Ala Gly Ala Leu Asp Glu Ser Gly Leu Arg Pro Glu
                85                  90                  95

Asp Leu Asp Val Leu Ile Thr Ala Thr Val Thr Gly Leu Ala Val Pro
            100                 105                 110

Ser Leu Asp Ala Arg Ile Ala Gly Arg Leu Gly Leu Arg Ala Asp Val
        115                 120                 125

Arg Arg Val Pro Leu Phe Gly Leu Gly Cys Val Ala Gly Ala Ala Gly
    130                 135                 140

Val Ala Arg Leu His Asp Tyr Leu Arg Gly Ala Pro Asp Gly Val Ala
145                 150                 155                 160

Ala Leu Val Ser Val Glu Leu Cys Ser Leu Thr Tyr Pro Gly Tyr Lys
                165                 170                 175

Pro Thr Leu Pro Gly Leu Val Gly Ser Ala Leu Phe Ala Asp Gly Ala
            180                 185                 190

Ala Ala Val Val Ala Ala Gly Val Lys Arg Ala Gln Asp Ile Gly Ala
        195                 200                 205

Asp Gly Pro Asp Ile Leu Asp Ser Arg Ser His Leu Tyr Pro Asp Ser
    210                 215                 220
```

```
Leu Arg Thr Met Gly Tyr Asp Val Gly Ser Ala Gly Phe Glu Leu Val
225                 230                 235                 240

Leu Ser Arg Asp Leu Ala Ala Val Val Glu Gln Tyr Leu Gly Asn Asp
                245                 250                 255

Val Thr Thr Phe Leu Ala Ser His Gly Leu Ser Thr Thr Asp Val Gly
            260                 265                 270

Ala Trp Val Thr His Pro Gly Gly Pro Lys Ile Ile Asn Ala Ile Thr
        275                 280                 285

Glu Thr Leu Asp Leu Ser Pro Gln Ala Leu Glu Leu Thr Trp Arg Ser
    290                 295                 300

Leu Gly Glu Ile Gly Asn Leu Ser Ser Ala Ser Val Leu His Val Leu
305                 310                 315                 320

Arg Asp Thr Ile Ala Lys Pro Pro Pro Ser Gly Ser Pro Gly Leu Met
                325                 330                 335

Ile Ala Met Gly Pro Gly Phe Cys Ser Glu Leu Val Leu Leu Arg Trp
            340                 345                 350

His
```

<210> SEQ ID NO 85
<211> LENGTH: 243
<212> TYPE: DNA
<213> ORGANISM: Mycobacterium tuberculosis

<400> SEQUENCE: 85

```
atgcacgcaa aagtcggcga ctacctcgtg gtgaagggca caaccacgga acggcatgat      60

caacatgctg agatcatcga ggtgcgctcc gcagacggct cgccgccata cgtggtgcgt     120

tggctggtaa acgggcacga gacaacggtg taccccgggt cggacgcggt cgtcgtcacc     180

gccaccgagc acgcggaggc cgaaaagcgc gctgccgcgc gggccgggca cgcggcgaca     240

tag                                                                   243
```

<210> SEQ ID NO 86
<211> LENGTH: 80
<212> TYPE: PRT
<213> ORGANISM: Mycobacterium tuberculosis

<400> SEQUENCE: 86

```
Met His Ala Lys Val Gly Asp Tyr Leu Val Val Lys Gly Thr Thr Thr
1               5                   10                  15

Glu Arg His Asp Gln His Ala Glu Ile Ile Glu Val Arg Ser Ala Asp
            20                  25                  30

Gly Ser Pro Pro Tyr Val Val Arg Trp Leu Val Asn Gly His Glu Thr
        35                  40                  45

Thr Val Tyr Pro Gly Ser Asp Ala Val Val Val Thr Ala Thr Glu His
    50                  55                  60

Ala Glu Ala Glu Lys Arg Ala Ala Ala Arg Ala Gly His Ala Ala Thr
65                  70                  75                  80
```

<210> SEQ ID NO 87
<211> LENGTH: 95
<212> TYPE: PRT
<213> ORGANISM: Mycobacterium tuberculosis

<400> SEQUENCE: 87

```
Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30
```

```
Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95


<210> SEQ ID NO 88
<211> LENGTH: 294
<212> TYPE: PRT
<213> ORGANISM: Mycobacterium tuberculosis

<400> SEQUENCE: 88

Ser Arg Gly Pro Leu Pro Val Glu Tyr Leu Gln Val Pro Ser Pro Ser
1               5                   10                  15

Met Gly Arg Asp Ile Lys Val Gln Phe Gln Ser Gly Gly Ala Asn Ser
            20                  25                  30

Pro Ala Leu Tyr Leu Leu Asp Gly Leu Arg Ala Gln Asp Asp Phe Ser
        35                  40                  45

Gly Trp Asp Ile Asn Thr Pro Ala Phe Glu Trp Tyr Asp Gln Ser Gly
    50                  55                  60

Leu Ser Val Val Met Pro Val Gly Gly Gln Ser Ser Phe Tyr Ser Asp
65                  70                  75                  80

Trp Tyr Gln Pro Ala Cys Gly Lys Ala Gly Cys Gln Thr Tyr Lys Trp
                85                  90                  95

Glu Thr Phe Leu Thr Ser Glu Leu Pro Gly Trp Leu Gln Ala Asn Arg
            100                 105                 110

His Val Lys Pro Thr Gly Ser Ala Val Val Gly Leu Ser Met Ala Ala
        115                 120                 125

Ser Ser Ala Leu Thr Leu Ala Ile Tyr His Pro Gln Gln Phe Val Tyr
    130                 135                 140

Ala Gly Ala Met Ser Gly Leu Leu Asp Pro Ser Gln Ala Met Gly Pro
145                 150                 155                 160

Thr Leu Ile Gly Leu Ala Met Gly Asp Ala Gly Gly Tyr Lys Ala Ser
                165                 170                 175

Asp Met Trp Gly Pro Lys Glu Asp Pro Ala Trp Gln Arg Asn Asp Pro
            180                 185                 190

Leu Leu Asn Val Gly Lys Leu Ile Ala Asn Asn Thr Arg Val Trp Val
        195                 200                 205

Tyr Cys Gly Asn Gly Lys Pro Ser Asp Leu Gly Gly Asn Asn Leu Pro
    210                 215                 220

Ala Lys Phe Leu Glu Gly Phe Val Arg Thr Ser Asn Ile Lys Phe Gln
225                 230                 235                 240

Asp Ala Tyr Asn Ala Gly Gly Gly His Asn Gly Val Phe Asp Phe Pro
                245                 250                 255

Asp Ser Gly Thr His Ser Trp Glu Tyr Trp Gly Ala Gln Leu Asn Ala
            260                 265                 270

Met Lys Pro Asp Leu Gln Arg Ala Leu Gly Ala Thr Pro Asn Thr Gly
        275                 280                 285

Pro Ala Pro Gln Gly Ala
    290


<210> SEQ ID NO 89
```

<211> LENGTH: 284
<212> TYPE: PRT
<213> ORGANISM: Mycobacterium tuberculosis

<400> SEQUENCE: 89

```
Ser Arg Pro Gly Leu Pro Val Glu Tyr Leu Gln Val Pro Ser Pro Ser
1               5                   10                  15

Met Gly Arg Asp Ile Lys Val Gln Phe Gln Ser Gly Gly Asn Asn Ser
            20                  25                  30

Pro Ala Val Tyr Leu Leu Asp Gly Leu Arg Ala Gln Asp Asp Tyr Asn
        35                  40                  45

Gly Trp Asp Ile Asn Thr Pro Ala Phe Glu Trp Tyr Tyr Gln Ser Gly
    50                  55                  60

Leu Ser Ile Val Met Pro Val Gly Gly Gln Ser Ser Phe Tyr Ser Asp
65                  70                  75                  80

Trp Tyr Ser Pro Ala Cys Gly Lys Ala Gly Cys Gln Thr Tyr Lys Trp
                85                  90                  95

Glu Thr Phe Leu Thr Ser Glu Leu Pro Gln Trp Leu Ser Ala Asn Arg
            100                 105                 110

Ala Val Lys Pro Thr Gly Ser Ala Ala Ile Gly Leu Ser Met Ala Gly
        115                 120                 125

Ser Ser Ala Met Ile Leu Ala Ala Tyr His Pro Gln Gln Phe Ile Tyr
    130                 135                 140

Ala Gly Ser Leu Ser Ala Leu Leu Asp Pro Ser Gln Gly Met Gly Pro
145                 150                 155                 160

Ser Leu Ile Gly Leu Ala Met Gly Asp Ala Gly Gly Tyr Lys Ala Ala
                165                 170                 175

Asp Met Trp Gly Pro Ser Ser Asp Pro Ala Trp Glu Arg Asn Asp Pro
            180                 185                 190

Thr Gln Gln Ile Pro Lys Leu Val Ala Asn Asn Thr Arg Leu Trp Val
        195                 200                 205

Tyr Cys Gly Asn Gly Thr Pro Asn Glu Leu Gly Gly Ala Asn Ile Pro
    210                 215                 220

Ala Glu Phe Leu Glu Asn Phe Val Arg Ser Ser Asn Leu Lys Phe Gln
225                 230                 235                 240

Asp Ala Tyr Asn Ala Ala Gly Gly His Asn Ala Val Phe Asn Phe Pro
                245                 250                 255

Pro Asn Gly Thr His Ser Trp Glu Tyr Trp Gly Ala Gln Leu Asn Ala
            260                 265                 270

Met Lys Gly Asp Leu Gln Ser Ser Leu Gly Ala Gly
        275                 280
```

<210> SEQ ID NO 90
<211> LENGTH: 96
<212> TYPE: PRT
<213> ORGANISM: Mycobacterium tuberculosis

<400> SEQUENCE: 90

```
Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60
```

```
Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95


<210> SEQ ID NO 91
<211> LENGTH: 111
<212> TYPE: PRT
<213> ORGANISM: Mycobacterium tuberculosis

<400> SEQUENCE: 91

Met Ile Val Gly Ala Ala Gly Gly Met Pro Pro Met Ala Pro Leu Ala
1               5                   10                  15

Pro Leu Leu Pro Ala Ala Ala Asp Ile Gly Leu His Ile Ile Val Thr
            20                  25                  30

Cys Gln Met Ser Gln Ala Tyr Lys Ala Thr Met Asp Lys Phe Val Gly
        35                  40                  45

Ala Ala Phe Gly Ser Gly Ala Pro Thr Met Phe Leu Ser Gly Glu Lys
    50                  55                  60

Gln Glu Phe Pro Ser Ser Glu Phe Lys Val Lys Arg Arg Pro Pro Gly
65                  70                  75                  80

Gln Ala Phe Leu Val Ser Pro Asp Gly Lys Val Ile Gln Ala Pro Tyr
                85                  90                  95

Ile Glu Pro Pro Glu Glu Val Phe Ala Ala Pro Pro Ser Ala Gly
            100                 105                 110


<210> SEQ ID NO 92
<211> LENGTH: 112
<212> TYPE: PRT
<213> ORGANISM: Mycobacterium tuberculosis

<400> SEQUENCE: 92

Leu Ile Pro Gly Arg Met Val Leu Asn Trp Glu Asp Gly Leu Asn Ala
1               5                   10                  15

Leu Val Ala Glu Gly Ile Glu Ala Ile Val Phe Arg Thr Leu Gly Asp
            20                  25                  30

Gln Cys Trp Leu Trp Glu Ser Leu Leu Pro Asp Glu Val Arg Arg Leu
        35                  40                  45

Pro Glu Glu Leu Ala Arg Val Asp Ala Leu Leu Asp Asp Pro Ala Phe
    50                  55                  60

Phe Ala Pro Phe Val Pro Phe Phe Asp Pro Arg Arg Gly Arg Pro Ser
65                  70                  75                  80

Thr Pro Met Glu Val Tyr Leu Gln Leu Met Phe Val Lys Phe Arg Tyr
                85                  90                  95

Arg Leu Gly Tyr Glu Ser Leu Cys Arg Glu Val Ala Asp Ser Ile Thr
            100                 105                 110


<210> SEQ ID NO 93
<211> LENGTH: 102
<212> TYPE: PRT
<213> ORGANISM: Mycobacterium tuberculosis

<400> SEQUENCE: 93

Met Thr Leu Arg Val Val Pro Glu Gly Leu Ala Ala Ala Ser Ala Ala
1               5                   10                  15

Val Glu Ala Leu Thr Ala Arg Leu Ala Ala Ala His Ala Ser Ala Ala
            20                  25                  30

Pro Val Ile Thr Ala Val Val Pro Pro Ala Ala Asp Pro Val Ser Leu
        35                  40                  45
```

```
Gln Thr Ala Ala Gly Phe Ser Ala Gln Gly Val Glu His Ala Val Val
    50                  55                  60

Thr Ala Glu Gly Val Glu Glu Leu Gly Arg Ala Gly Val Gly Val Gly
65                  70                  75                  80

Glu Ser Gly Ala Ser Tyr Leu Ala Gly Asp Ala Ala Ala Ala Ala Thr
                85                  90                  95

Tyr Gly Val Val Gly Gly
            100


<210> SEQ ID NO 94
<211> LENGTH: 97
<212> TYPE: PRT
<213> ORGANISM: Mycobacterium tuberculosis

<400> SEQUENCE: 94

Met Ser Leu Leu Asp Ala His Ile Pro Gln Leu Val Ala Ser Gln Ser
1               5                   10                  15

Ala Phe Ala Ala Lys Ala Gly Leu Met Arg His Thr Ile Gly Gln Ala
            20                  25                  30

Glu Gln Ala Ala Met Ser Ala Gln Ala Phe His Gln Gly Glu Ser Ser
        35                  40                  45

Ala Ala Phe Gln Ala Ala His Ala Arg Phe Val Ala Ala Ala Ala Lys
    50                  55                  60

Val Asn Thr Leu Leu Asp Val Ala Gln Ala Asn Leu Gly Glu Ala Ala
65                  70                  75                  80

Gly Thr Tyr Val Ala Ala Asp Ala Ala Ala Ala Ser Thr Tyr Thr Gly
                85                  90                  95

Phe


<210> SEQ ID NO 95
<211> LENGTH: 8
<212> TYPE: DNA
<213> ORGANISM: Artificial Sequence
<220> FEATURE:
<223> OTHER INFORMATION: Chemically synthesized

<400> SEQUENCE: 95

agtcagtc                                                                8


<210> SEQ ID NO 96
<211> LENGTH: 8
<212> TYPE: DNA
<213> ORGANISM: Artificial Sequence
<220> FEATURE:
<223> OTHER INFORMATION: Chemically synthesized

<400> SEQUENCE: 96

aatcaatc                                                                8


<210> SEQ ID NO 97
<211> LENGTH: 6
<212> TYPE: DNA
<213> ORGANISM: Artificial Sequence
<220> FEATURE:
<223> OTHER INFORMATION: Chemically synthesized

<400> SEQUENCE: 97

agtgtc                                                                  6
```

TUBERCULOSIS VACCINES COMPRISING ANTIGENS EXPRESSED DURING THE LATENT INFECTION PHASE

CROSS REFERENCE TO RELATED APPLICATIONS

This application is a divisional of and claims the benefit of priority under 35 U.S.C. §120 to U.S. patent application Ser. No. 13/335,133, filed Dec. 22, 2011 (now U.S. Pat. No. 8,293, 250), which is a continuation of and claims priority to U.S. patent application Ser. No. 13/101,980, filed May 5, 2011, now U.S. Pat. No. 8,101,980, which 13/is a continuation of and claims priority to U.S. patent application Ser. No. 11/993, 199, filed Jul. 25, 2008, now U.S. Pat. No. 7,968,105, which claims priority to and is a U.S. National Phase filing of PCT International Application Number PCT/DK2006/000356, filed on Jun. 20, 2006, designating the United States of America and published in the English language, which claims priority to Denmark Patent Application Number PA 2005 01393 filed on Oct. 5, 2005, and Denmark Patent Application Number PA 2005 00924 filed on Jun. 23, 2005. The disclosures of the above-described applications are hereby expressly incorporated by reference in their entireties.

REFERENCE TO SEQUENCE LISTING

The present application is being filed along with a sequence listing in electronic format. The sequence listing is provided as a file entitled PLOUG8.003D1.txt, created Sep. 19, 2012 which is 21 KB in size. The information in the electronic format of the sequence listing is incorporated herein by reference in its entirety.

FIELD OF INVENTION

The present invention discloses starvation induced antigens or new fusion polypeptides of immunogenic polypeptides based on polypeptides derived from *Mycobacterium tuberculosis* induced during starvation, the use of one or more of the fusion polypeptides or starvation induced antigens of the invention for the preparation of an immunogenic composition, vaccine or pharmaceutical composition to be used for administration to a person/animal and the immunogenic compositions, vaccines or pharmaceutical compositions as such.

GENERAL BACKGROUND

Human tuberculosis caused by *Mycobacterium tuberculosis* (*M. tuberculosis*) is a severe global health problem, responsible for approximately 3 million deaths annually, according to the WHO. The worldwide incidence of new tuberculosis (TB) cases had been falling during the 1960s and 1970s but during recent years this trend has markedly changed in part due to the advent of AIDS and the appearance of multidrug resistant strains of *M. tuberculosis.*

The only vaccine presently available for clinical use is BCG, a vaccine whose efficacy remains a matter of controversy. BCG generally induces a high level of acquired resistance in animal models of TB, and in humans it is protective against disseminated forms of tuberculosis such as meningitis and miliary tuberculosis. When given to young children it is protective against tuberculosis for years but then the efficacy wanes. Comparison of various controlled trials revealed that the protective efficacy of BCG in adults varied dramatically with an efficacy range from ineffective to 80% protection. This makes the development of a new and improved vaccine against *M. tuberculosis* an urgent matter, which has been given a very high priority by the WHO.

Many attempts to define protective mycobacterial substances have been made, and different investigators have reported increased resistance after experimental vaccination. *M. tuberculosis* holds, as well as secretes, several proteins of potential relevance for the generation of a new *M. tuberculosis* vaccine. The search for candidate molecules has primarily focused on proteins released from dividing bacteria. Despite the characterization of a large number of such proteins only a few of these have been demonstrated to induce a protective immune response as subunit vaccines in animal models, most notably ESAT-6 and Ag85B (Brandt et al 2000). However, the demonstration of a specific long-term protective immune response with the potency of BCG or the capability of boosting in a BCG vaccinating person has not yet been achieved. At best, boost of BCG with BCG has no effect [Colditz, 1994]. Boosting of BCG has been done with Ag85A Brooks et al IAI 2001; WO0204018) in an inbred mouse strain leading to some protection, although compared to BCG alone it was not significantly better. Since BCG needs to divide and secrete proteins in order to induce a protective immune response, the lack of booster effect is primarily due to either sensitization with environmental mycobacteria or a residual immune response from the primary BCG vaccination. Both events lead to a rapid immune response against BCG and therefore quick inhibition of growth and elimination of BCG.

The course of a *M. tuberculosis* infection runs essentially through 3 phases. During the acute phase, the bacteria proliferate in the organs, until the immune response increases. Specifically sensitized CD4 T lymphocytes mediate control of the infection, and the most important mediator molecule seems to be interferon gamma (IFN-gamma). The bacterial loads starts to decline and a latent phase is established where the bacterial load is kept stable at a low level. In this phase *M. tuberculosis* goes from active multiplication to dormancy, essentially becoming non-replicating and remaining inside the granuloma. In some cases, the infection goes to the reactivation phase, where the dormant bacteria start replicating again. It has been suggested that the transition of *M. tuberculosis* from primary infection to latency is accompanied by changes in gene expression (Honer zu Bentrup, 2001). It is also likely that changes in the antigen-specificity of the immune response occur, as the bacteria modulates gene expression during its transition from active replication to dormancy. The full nature of the immune response that controls latent infection and the factors that lead to reactivation are largely unknown. However, there is some evidence for a shift in the dominant cell types responsible. While CD4 T cells are essential and sufficient for control of infection during the acute phase, studies suggest that CD8 T cell responses are more important in the latent phase.

In 1998 Cole et al published the complete genome sequence of *M. tuberculosis* and predicted the presence of approximately 4000 open reading frames (Cole et al 1998) disclosing nucleotide sequences and putative protein sequences. However importantly, this sequence information cannot be used to predict if the DNA is translated and expressed as proteins in vivo. It is known that some genes of *M. tuberculosis* are upregulated under conditions that mimic latency. However, these are a limited subset of the total gene expression during latent infection. Moreover, as one skilled in the art will readily appreciate, expression of a gene is not sufficient to make it a good vaccine candidate. The only way to determine if a protein is recognized by the immune system during latent infection with *M. tuberculosis* is to produce the given protein and test it in an appropriate assay as described herein. A number of proteins are of particular importance and have potential for being late antigens (antigens recognized during latent infection) since they are mainly expressed a relatively long time after infection where the immune system has mounted the first adaptive defense and the environment has turned more hostile for the mycobateria. In vitro hypoxic culture conditions, which mimic the conditions of low oxygen tension have previously been suggested as relevant in this regard and have been used to analyze changes in gene expression. A number of antigens have been found that are induced or markedly upregulated under these conditions e.g. the 16 kDa antigen α-crystallin (Sherman 2001), Rv2660c and Rv2659c (Betts, 2002). (our own application) Another environmental stimuli which may be of particular interest is starvation designed to reflect that nutrients are restricted in the granuloma (the location of the latent infection) and that products expressed by genes upregulated under starvation therefore may be of particular interest as antigen targets during the latent stage of infection.

Of the more than 200 hundred antigens known to be expressed during primary infection, and tested as vaccines, less than a half dozen have demonstrated significant potential. So far only one antigen has been shown to have any potential as a therapeutic vaccine (Lowrie, 1999). However this vaccine only worked if given as a DNA vaccine and has proved controversial, with other groups claiming that vaccination using this protocol induces either non-specific protection or even worsens disease (Turner, 2000). In contrast, the fusion polypeptides described in the invention may be incorporated in a vaccine that use well-recognized vaccination technology, as demonstrated in provided examples.

Further, since TB vaccines do not result in sterilizing immunity but rather control the infection at a subclinical level (thereby resulting in the subsequent establishment of latent infection), a multiphase vaccine which combines components with prophylactic and therapeutic activity is described in this invention. After conventional prophylactic vaccination, the evasion of the primary immune response and the subsequent development of latent disease is probably at least in part due to the change in the antigenic profile of the invading bacteria. Thus, vaccinating with antigens associated with latent TB should prevent or reduce the establishment of latent infection and therefore, a vaccine incorporating antigens expressed by the bacteria both in the first logarithmic growth phase and during latent disease should improve long-term immunity when used as a prophylactic vaccine. Such a multiphase vaccine will obviously also be efficient as a therapeutic vaccine thereby addressing the problem that the majority of the population in the third world who would receive a future TB vaccine would be already latently infected.

SUMMARY OF THE INVENTION

The invention is related to an immunogenic composition, vaccine or pharmaceutical composition for preventing (including booster vaccination and multiphase vaccines) or/and treating infection caused by a species of the *M. tuberculosis* complex (*M. tuberculosis, M. Bovis, M. africanum* etc.), the immunogenic composition, the vaccine or pharmaceutical composition comprising starvation induced antigen or a fusion polypeptide which comprises one or more starvation induced *M. tuberculosis* antigens, the units of the fusion polypeptide being *M. tuberculosis* antigens. Also, the invention relates to the fusion polypeptides as such and to a nucleic acid sequence encoding such a fusion polypeptide. Further, the invention relates to the use of short or long overlapping or non-overlapping peptide(s) made synthetically or recombinant. Further, the invention relates to the use of a starvation induced antigen or a fusion polypeptide sequence or nucleic acid sequence of the invention for preparing said immunogenic composition, vaccine, or pharmaceutical composition and the vaccine or pharmaceutical composition produced in this way. Further, the invention relates to the use of a vaccine comprising a starvation induced antigen or a fusion polypeptide sequence or nucleic acid sequence of the invention given at the same time as BCG, either mixed with BCG or administered separately at different sites or routes for preparing said immunogenic composition, vaccine, or pharmaceutical composition. Further the invention relates to the use of a vaccine comprising a starvation induced antigen or a fusion polypeptide sequence or nucleic acid sequence given as a BCG booster. Furthermore, by including antigens that are expressed both early and late during a natural infection the vaccine will lead to a two step immune response allowing the immune system to combat the pathogen with whatever epitopes are most efficient at a certain timepoint including during latency.

DETAILED DISCLOSURE OF THE INVENTION

The present invention discloses immunogenic compositions, a vaccine or a pharmaceutical composition comprising a starvation induced antigen or a fusion polypeptide comprising one or more starvation induced antigens.

The amino acid and nucleic acid sequences of these starvation induced (more than 6.5 fold upregulated during starvation or genetically linked to a starvation induced gene) antigens appear from the sequence listing as follows:

| Starvation induced antigen | DNA SEQ ID NO | aa SEQ ID NO |
|---|---|---|
| Rv2655 | 1 | 2 |
| Rv2656 | 3 | 4 |
| Rv2657 | 5 | 6 |
| Rv2658 | 7 | 8 |
| Rv2659c | 9 | 10 |
| Rv2660c | 11 | 12 |
| Rv2661 | 13 | 14 |
| Rv2662 | 15 | 16 |
| Rv2663 | 17 | 18 |
| Rv0188 | 19 | 20 |
| Rv3290c | 21 | 22 |
| Rv3289c | 23 | 24 |
| Rv2034 | 25 | 26 |
| Rv2169c | 27 | 28 |
| Rv0116c | 29 | 30 |
| Rv2558 | 31 | 32 |
| Rv1152 | 33 | 34 |
| Rv3291c | 35 | 36 |
| Rv1284 | 37 | 38 |
| Rv1954c | 39 | 40 |
| Rv3810 | 41 | 42 |
| Rv2517c | 43 | 44 |
| Rv3288c | 45 | 46 |
| Rv0789c | 47 | 48 |
| Rv1955 | 49 | 50 |
| Rv3735 | 51 | 52 |
| Rv3675 | 53 | 54 |
| Rv2270 | 55 | 56 |
| Rv2050 | 57 | 58 |
| Rv3287c | 59 | 60 |
| Rv2557 | 61 | 62 |
| Rv0122 | 63 | 64 |
| Rv2497c | 65 | 66 |
| Rv1250 | 67 | 68 |
| Rv1552 | 69 | 70 |
| Rv2526 | 71 | 72 |
| Rv1809 | 73 | 74 |
| Rv0918 | 75 | 76 |

-continued

| Starvation induced antigen | DNA SEQ ID NO | aa SEQ ID NO |
|---|---|---|
| Rv0516c | 77 | 78 |
| Rv2745c | 79 | 80 |
| Rv1472 | 81 | 82 |
| Rv1660 | 83 | 84 |
| Rv2302 | 85 | 86 |

In the present context the individual immunogenic polypeptide based on polypeptides derived from *M. tuberculosis* is termed a "unit" of the fusion polypeptide. The fusion may comprise 2, 3, 4, 5, 6, 7, 8, 9 or even 10 different units.

The order of the units of the fusion polypeptide can be any combination. In order terms, fusion polypeptides of all of the above antigens in any combination are within the scope of the present invention. The fusion polypeptides of the invention are useful for the preparation of an immunogenic composition, vaccine or pharmaceutical composition, in particular a BCG booster vaccine, as will be described in detail in the following.

The preferred polypeptides making up units of the fusion polypeptides together with the starvation polypeptides have the following Sanger identity number and amino acid sequences:

| Trivial name | Sanger ID |
|---|---|
| ESAT6 | Rv3875 |
| TB10.4 | Rv0288 |
| Ag85A | Rv3804c |
| Ag85B | Rv1886c |
| ORF2c | Rv3871 (c-terminal) |
| TB13.0 | Rv1036 |
| TB9.56 | Rv0285 |
| TB9.8 | Rv0287 |

| Polypeptide amino acid sequence | | aa SEQ ID NO |
|---|---|---|
| ESAT6 | MTEQQWNFAG IEAAASAIQG NVTSIHSLLD EGKQSLTKLA AAWGGSGSEA YQGVQQKWDA TATELNNALQ NLARTISEAG QAMASTEGNV TGMFA | 87 |
| Ag85A | SRGPLP VEYLQVPSPS MGRDIKVQFQ SGGANSPALY LLDGLRAQDD FSGWDINTPA FEWYDQSGLS VVMPVGGQSS FYSDWYQPAC GKAGCQTYKW ETFLTSELPG WLQANRHVKP TGSAVVGLSM AASSALTLAI YHPQQFVYAG AMSGLLDPSQ AMGPTLIGLA MGDAGGYKAS DMWGPKEDPA WQRNDPLLNV GKLIANNTRV WVYCGNGKPS DLGGNNLPAK FLEGFVRTSN IKFQDAYNAG GGHNGVFDFP DSGTHSWEYW GAQLNAMKPD LQRALGATPN TGPAPQGA | 88 |
| Ag85B | SRPGLPVEY LQVPSPSMGR DIKVQFQSGG NNSPAVYLLD GLRAQDDYNG WDINTPAFEW YYQSGLSIVM PVGGQSSFYS DWYSPACGKA GCQTYKWETF LTSELPQWLS ANRAVKPTGS AAIGLSMAGS SAMILAAYHP QQFIYAGSLS ALLDPSQGMG PSLIGLAMGD AGGYKAADMW GPSSDPAWER NDPTQQIPKL VANNTRLWVY CGNGTPNELG GANIPAEFLE NFVRSSNLKF QDAYNAAGGH NAVFNFPPNG THSWEYWGAQ LNAMKGDLQS SLGAG | 89 |
| TB10.4 | MSQIMYNYPA MLGHAGDMAG YAGTLQSLGA EIAVEQAALQ SAWQGDTGIT YQAWQAQWNQ AMEDLVRAYH AMSSTHEANT MAMMARDTAE AAKWGG | 90 |
| ORF2c | MIVGAAGGMP PMAPLAPLLP AAADIGLHII VTCQMSQAYK ATMDKFVGAA FGSGAPTMFL SGEKQEFPSS EFKVKRRPPG QAFLVSPDGK VIQAPYIEPP EEVFAAPPSA G | 91 |
| Rv1036 | LIPGRMVLNW EDGLNALVAE GIEAIVFRTL GDQCWLWESL LPDEVRRLPE ELARVDALLD DPAFFAPFVP FFDPRRGRPS TPMEVYLQLM FVKFRYRLGY ESLCREVADS IT | 92 |
| Rv0285 | MTLRVVPEGL AAASAAVEAL TARLAAAHAS AAPVITAVVP PAADPVSLQT AAGFSAQGVE HAVVTAEGVE ELGRAGVGVG ESGASYLAGD AAAAATYGVV GG | 93 |
| Rv0287 | MSLLDAHIPQ LVASQSAFAA KAGLMRHTIG QAEQAAMSAQ AFHQGESSAA FQAAHARFVA AAAKVNTLLD VAQANLGEAA GTYVAADAAA ASTYTGF | 94 |

Preferred combinations of fusion polypeptides comprise the following polypeptides in various combinations in order of units with one or more starvation induced antigens (X): ESAT6-Ag85A-X, ESAT6-Ag85B-X, Ag85A-X, Ag85B-X, TB10-Ag85A-X, TB10-Ag85B-X where X is any of the starvation induced antigens and where the order of the units of antigens can be of any combination e.g. where the order is reversed or X is positioned in the middle etc.

But the fusion polypeptide could be constructed from any other combination of one or more starvation induced antigen with one or more *M. tuberculosis* antigen.

Within the scope of the present invention is an analogue of a fusion polypeptide which has an amino acid sequence with a sequence identity of at least 80% to any part of any one of the fusion polypeptides of the invention and which is immunogenic, and a nucleic acid sequence which encodes such polypeptide. Such analogues are comprised within the term “polypeptide of the invention” or “fusion polypeptide of the invention” which terms are used interchangeably throughout the specification and claims. By the term “nucleic acid sequence of the invention” is meant a nucleic acid sequence encoding such a polypeptide. Further within the scope of the present invention are short or long peptide(s) overlapping or non-overlapping which has an amino acid sequence with a sequence identity of at least 80% to any one of the fusion polypeptides of the invention and which is immunogenic A presently preferred embodiment of the invention is a vaccine to boost immunity from prior BCG vaccination, i.e. the vaccine is administered to individuals previously vaccinated with BCG.

This first aspect of the invention comprises a variant of the above mentioned starvation induced antigen or fusion polypeptide which is lipidated so as to allow a self-adjuvating effect of the polypeptide.

The immunogenic composition, vaccine or pharmaceutical composition of the invention can be administered by mucosal delivery, e.g. orally, nasally, buccally, or traditionally intramuscularly, intradermally, by subcutaneous injection or transdermally or any other suitable route, e.g. rectally.

In another embodiment, the invention discloses the use of a starvation induced antigen or a fusion polypeptide as defined above for the preparation of an immunogenic composition, vaccine or pharmaceutical composition which can be used for a prophylactic vaccination together with BCG, a booster vaccine or therapeutic vaccination against an infection caused by a virulent *mycobacterium,* e.g. by *Mycobacterium tuberculosis, Mycobacterium africanum, Mycobacterium bovis, Mycobacterium leprae* or *Mycobacterium ulcerans.*

In a second aspect, the invention discloses an immunogenic composition, vaccine or pharmaceutical composition which comprises a nucleotide sequence which encodes a starvation induced antigen or a fusion polypeptide as defined above, or comprises a nucleic acid sequence complementary thereto which is capable of hybridizing to the nucleic acid sequence of the invention under stringent conditions.

The nucleic acid fragment is preferably a DNA fragment. The fragment can be used as a pharmaceutical as discussed in the following.

In one embodiment, the invention discloses an immunogenic composition, vaccine or pharmaceutical composition comprising a nucleic acid fragment according to the invention, optionally inserted in a vector. The vaccine resulting in vivo expression of antigen by an animal, including a human being, to whom the vaccine has been administered, the amount of expressed antigen being effective to confer substantially increased resistance to tuberculosis caused by virulent mycobacteria, e.g. by *Mycobacterium tuberculosis, Mycobacterium africanum, Mycobacterium bovis, Mycobacterium leprae* or *Mycobacterium ulcerans*, in an animal, including a human being.

In a further embodiment, the invention discloses the use of an immunogenic composition, vaccine or pharmaceutical composition comprising a nucleic acid fragment according to the invention for therapeutic vaccination against tuberculosis caused by a virulent *mycobacterium.*

In a still further embodiment, the invention discloses an immunogenic composition, vaccine or pharmaceutical composition which can be used for prophylactic vaccination together with BCG or as a booster vaccine to a person previously vaccinated with BCG for immunizing an animal, including a human being, against tuberculosis caused by a virulent *mycobacterium*, e.g. by *Mycobacterium tuberculosis, Mycobacterium africanum, Mycobacterium bovis, Mycobacterium leprae* or *Mycobacterium* ulcerans, comprising as the effective component a non-pathogenic microorganism, such as vaccinia, adenovirus or *Mycobacterium bovis* BCG, wherein at least one copy of a DNA fragment comprising a DNA sequence encoding a fusion polypeptide as defined above has been incorporated into the microorganism (e.g. placed on a plasmid or in the genome) in a manner allowing the microorganism to express and optionally secrete the fusion polypeptide.

In another embodiment, the invention discloses an infectious expression vector, such as vaccinia, adenovirus or *Mycobacterium bovis* BCG which comprises a nucleic acid fragment according to the invention, and a transformed cell harboring at least one such vector.

In a third aspect, the invention discloses a method for immunizing and boosting the immunity of an animal, including a human being, against tuberculosis caused by virulent mycobacteria, e.g. by *Mycobacterium tuberculosis, Mycobacterium africanum, Mycobacterium bovis, Mycobacterium leprae* or *Mycobacterium* ulcerans, the method comprising administering to the animal the fusion polypeptide as defined above, the immunogenic composition according to the invention, or the vaccine according to the invention.

In a fourth aspect, the invention discloses a method for treating an animal, including a human being, having tuberculosis, active or latent, caused by virulent mycobacteria, e.g. by *Mycobacterium tuberculosis, Mycobacterium africanum, Mycobacterium bovis, Mycobacterium leprae* or *Mycobacterium* ulcerans, the method comprising administering to the animal the immunogenic composition, vaccine or pharmaceutical composition as defined above.

In a fifth aspect, the invention discloses the use of a starvation induced antigen or a fusion polypeptide or nucleic acid fragment as defined above for the preparation of an immunogenic composition, vaccine or pharmaceutical composition in combination with *M. bovis* BCG, e.g. for a prophylactic (including boosting) or therapeutical vaccination against an infection caused by a virulent *mycobacterium*, e.g. by *Mycobacterium tuberculosis, Mycobacterium africanum, Mycobacterium bovis, Mycobacterium leprae* or *Mycobacterium* ulcerans.

The vaccine, immunogenic composition, vaccine and pharmaceutical composition according to the invention can be used prophylactically in a subject not infected with a virulent *mycobacterium* or in an individual previously vaccinated with *M. tuberculosis* BCG or therapeutically in a subject infected with a virulent *mycobacterium.*

It is to be understood that the embodiments of the first aspect of the invention, such as the immunogenic polypeptides described also apply to all other aspects of the invention; and vice versa.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

DEFINITIONS

Starvation

By the term "starvation" is understood depriving an organism of its carbon, nitrogen or energy source, any combination of the above or even all of them.

Starvation Induced Proteins

By the term "starvation induced proteins" is understood any protein that at the transcriptional or protein level is induced (increased) at least 6.5 fold after stressing the mycobacteria by starvation.

Combination with *M. bovis* BCG

By the term "combination with *M. bovis* BCG" is understood co-administration with any *M. bovis* BCG strain including, Pasteur, Phipps, Frappier, Connaught, Tice, Denmark, Glaxo, Prague, Birkhaug, Sweden, Japan, Moreau and Russia in quantities that lead either to a significant increased specific immune response or to a significant protection in an animal model or a human either together with one or more of the fusion polypeptides defined above or with one or more of the nucleic acid fragments encoding these, or administered at the same time but at separate sites or routes.

Boost of *M. bovis* BCG

By the term "boost of *M. bovis* BCG" is understood administration of one or more fusion polypeptides as defined above or one or more nucleic acid fragments encoding these at any period after vaccination with any *M. bovis* BCG strain including, Pasteur, Phipps, Frappier, Connaught, Tice, Denmark, Glaxo, Prague, Birkhaug, Sweden, Japan, Moreau and Russia in quantities that lead either to a significantly increased specific immune response or a significantly increased protection in an animal model or a human.

Polypeptide

A preferred polypeptide to be used as a unit of the fusion polypeptides of the present invention is an immunogenic polypeptide from *M. tuberculosis*. Such polypeptide can for example be based on a polypeptide derived from the *M. tuberculosis* cell and/or *M. tuberculosis* culture filtrate. The polypeptide will normally be a recombinant or synthetic polypeptide and may consist of the immunogenic polypeptide, an immunogenic portion thereof or may contain additional sequences. The additional sequences may be derived from the native *M. tuberculosis* antigen or be heterologous and such sequences may, but need not, be immunogenic.

By the term "fusion polypeptide" is understood a random order of two or more immunogenic polypeptides from *M. tuberculosis* or analogues thereof fused together with or without an amino acid spacer(s) of arbitrary length and sequence.

The word "polypeptide" in the present invention should have its usual meaning. That is an amino acid chain of any length, including a full-length protein, oligopeptide, short peptide and fragment thereof and fusion polypeptide, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a his-tag or a signal peptide.

Each immunogenic polypeptide will be characterized by specific amino acids and be encoded by specific nucleic acid sequences. Within the scope of the present invention are such sequence and analogues and variants produced by recombinant or synthetic methods wherein such polypeptide sequences have been modified by substitution, insertion, addition or deletion of one or more amino acid residues in the recombinant polypeptide while still being immunogenic in any of the biological assays described herein.

Substitutions are preferably "conservative". These are defined according to the following table. Amino acids in the same block in the second column and preferably in the same line in the third column may be substituted for each other. The amino acids in the third column are indicated in one-letter code.

| | | |
|---|---|---|
| ALIPHATIC | Non-polar | GAP |
| | | ILV |
| | Polar-uncharged | CSTM |
| | | NQ |
| | Polar-charged | DE |
| | | KR |
| AROMATIC | | HFWY |

Each polypeptide is encoded by a specific nucleic acid sequence. Within the scope of the present invention are analogues and such nucleic acid sequences which have been modified by substitution, insertion, addition or deletion of one or more nucleic acids. Substitutions are preferably silent substitutions in the codon usage which will not lead to any change in the amino acid sequence, but may be introduced to enhance the expression of the protein.

Nucleic Acid Fragment

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least one epitope is preferably used, having a length from about 18 to about 1000 nucleotides, the molecule being optionally inserted into a vector. When the nucleic acid molecule is used as a probe, as a primer or in antisense therapy, a molecule having a length of 10-100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, 30 or 20 nucleotides (or nucleotide derivatives).

The term "stringent" when used in conjunction with hybridization conditions is as defined in the art, i.e. the hybridization is performed at a temperature not more than 15-20° C. under the melting point Tm, cf. Sambrook et al, 1989, pages 11.45-11.49. Preferably, the conditions are "highly stringent", i.e. 5-10° C. under the melting point Tm.

Sequence Identity

The term "sequence identity" indicates a quantitative measure of the degree of homology between two amino acid sequences of substantially equal length or between two nucleic acid sequences of substantially equal length. The two sequences to be compared must be aligned to best possible fit possible with the insertion of gaps or alternatively, truncation at the ends of the protein sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC (SEQ ID NO: 95) will have a sequence identity of 75% with the sequence AATCAATC (SEQ ID NO: 96) ($N_{dif}$=2 and $N_{ref}$=8). A gap is counted as non-identity of the specific residue(s), i.e. the DNA sequence AGTGTC (SEQ ID NO: 97) will have a sequence identity of 75% with the DNA sequence AGTCAGTC (SEQ ID NO: 95) ($N_{dif}$=2 and $N_{ref}$=8). Sequence identity can alternatively be calculated by the BLAST program e.g. the BLASTP program (Pearson W. R and D. J. Lipman (1988)). In one embodiment of the invention, alignment is performed with the sequence alignment method ClustalW with default parameters as described by Thompson J., et al 1994.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%. Preferably, the numbers of substitutions, insertions, additions or deletions of one or more amino acid residues in the fusion polypeptide is limited, i.e. no more than 1, 2, 3, 4, 5, 6, 7, 8, 9, 10 substitutions, no more than 1, 2, 3, 4, 5, 6, 7, 8, 9, 10 insertions, no more than 1, 2, 3, 4, 5, 6, 7, 8, 9, 10 additions, and no more than 1, 2, 3, 4, 5, 6, 7, 8, 9, 10 deletions compared to the immunogenic polypeptide units based on polypeptides derived from *M. tuberculosis.*

Immunogenic Portion

The polypeptide of the invention comprises an immunogenic portion, such as an epitope for a B-cell or T-cell.

The immunogenic portion of an immunogenic polypeptide is the part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn et al 1999).

In order to identify relevant T-cell epitopes which are recognized during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-gamma assay described herein. Another method utilizes overlapping oligopeptides for the detection of MHC class II epitopes, preferably synthetic, having a length of e.g. 20 amino acid residues derived from the polypeptide. These peptides can be tested in biological assays (e.g. the IFN-gamma assay as described herein) and some of these will give a positive response (and thereby be immunogenic) as evidence for the presence of a T cell epitope in the peptide. For the detection of MHC class I epitopes it is possible to predict peptides that will bind (Stryhn et al. 1996) and hereafter produce these peptides synthetically and test them in relevant biological assays e.g. the IFN-gamma assay as described herein. The peptides preferably having a length of e.g. 8 to 11 amino acid residues derived from the polypeptide. B-cell epitopes can be determined by analyzing the B cell recognition to overlapping peptides covering the polypeptide of interest as e.g. described in Harboe et al 1998.

Immunogenic portions of polypeptides may be recognized by a broad part (high frequency) or by a minor part (low frequency) of the genetically heterogenic human population. In addition some immunogenic portions induce high immunological responses (dominant), whereas others induce lower, but still significant, responses (subdominant). High frequency or low frequency can be related to the immunogenic portion binding to widely distributed MHC molecules (HLA type) or even by multiple MHC molecules (Kilgus et al. 1991, Sinigaglia et al 1988).

Analogues

A common feature of the fusion polypeptides of the invention is their capability to induce an immunological response as illustrated in the examples. It is understood that within the scope of the present invention are analogues of a fusion polypeptide of the invention produced by substitution, insertion, addition or deletion is also immunogenic determined by any of the assays described herein.

Substantially Pure

In the present context the term "substantially pure polypeptide" means a polypeptide preparation which contains at most 5% by weight of other polypeptide material with which it is associated natively or during recombinant or synthetic production (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide is in "essentially pure form", i.e. that the polypeptide is essentially free of any other antigen with which it is natively associated, i.e. free of any other antigen from bacteria belonging to the tuberculosis complex or a virulent *mycobacterium*. This can be accomplished by preparing the polypeptide by means of recombinant methods in a non-mycobacterial host cell as will be described in detail below, or by synthesizing the polypeptide by the well-known methods of solid or liquid phase peptide synthesis, e.g. by the method described by Merrifield or variations thereof, and by using appropriate purification procedures well known to the person of ordinary skill in the art (Merrifield 1962, Merrifield 1963).

Virulent *Mycobacterium*, Individual Currently Infected and Immune Individual

By the term "virulent *mycobacterium*" is understood a bacterium capable of causing the tuberculosis disease in an animal or in a human being. Examples of virulent mycobacteria are *Mycobacterium tuberculosis, Mycobacterium africanum, Mycobacterium bovis, Mycobacterium leprae* or *Mycobacterium ulcerans*. Examples of relevant animals are cattle, possums, badgers, buffaloes, lions, kurus and kangaroos.

By "an animal or human currently infected with a virulent *mycobacterium*" is understood an individual with culture or microscopically proven infection with virulent mycobacteria, and/or an individual clinically diagnosed with TB and who is responsive to anti-TB chemotherapy. Culture, microscopy and clinical diagnosis of TB are well known by any person skilled in the art.

An immune individual is defined as a person or an animal, which has cleared or controlled an infection with a virulent *mycobacterium* or has received a vaccination with *M. bovis* BCG.

Immunogenic

An immunogenic polypeptide is defined as a polypeptide that induces an immune response. The immune response may be monitored by one of the following methods:

An in vitro cellular response is determined by release of a relevant cytokine such as IFN-gamma, from lymphocytes withdrawn from an animal or human currently or previously infected with virulent mycobacteria, or by detection of proliferation of these T cells. The induction is performed by addition of the polypeptide or the immunogenic portion to a suspension comprising from $1\times10^5$ cells to $3\times10^5$ cells per well. The cells are isolated from either blood, the spleen, the liver or the lung and the addition of the polypeptide or the immunogenic portion of the polypeptide result in a concentration of not more than 20 ug per ml suspension and the stimulation is performed from two to five days. For monitoring cell proliferation the cells are pulsed with radioactive labeled thymidine and after 16-22 hours of incubation the proliferation is detected by liquid scintillation counting. A positive response is a response more than background plus two standard deviations. The release of IFN-gamma can be determined by the ELISA method, which is well known to a person skilled in the art. A positive response is a response more than background plus two standard deviations. Other cytokines than IFN-gamma could be relevant when monitoring an immunological response to the polypeptide, such as IL-12, TNF-α, IL-4, IL-5, IL-10, IL-6, TGF-β. Another and more sensitive method for determining the presence of a cytokine (e.g. IFN-gamma) is the ELISPOT method where the cells isolated from either the blood, the spleen, the liver or the lung are diluted to a concentration of preferable of 1 to $4\times10^6$ cells/ml and incubated for 18-22 hrs in the presence of the polypeptide or the immunogenic portion of the polypeptide resulting in a concentration of not more than 20 ug per ml. The cell suspensions are hereafter diluted to 1 to $2\times10^6$/ml and transferred to Maxisorp plates coated with anti-IFN-gamma and incubated for preferably 4 to 16 hours. The IFN-gamma producing cells are determined by the use of labelled secondary anti-IFN-antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or an *M. tuberculosis* infected person where the T cell lines have been driven with either live mycobacteria, extracts from the bacterial cell or culture filtrate for 10 to 20 days with the addition of IL-2. The induction is performed by addition of not more than 20 ug polypeptide per ml suspension to the T cell lines containing from $1\times10^5$ cells to $3\times10^5$ cells per well and incubation is performed from two to six days. The induction of IFN-gamma or release of another relevant cytokine is detected by ELISA. The stimulation of T cells can also be monitored by detecting cell proliferation using radioactively labeled Thymidine as described above. For both assays a positive response is a response more than background plus two standard deviations.

An in vivo cellular response may be determined as a positive DTH response after intradermal injection or local application patch of at most 100 ug of the polypeptide or the immunogenic portion to an individual who is clinically or subclinically infected with a virulent *Mycobacterium*, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the presence or absence of a specific label e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of a virulent *Mycobacterium*. Readout for induced protection could be decrease of the bacterial load in target organs compared to non-vaccinated animals, prolonged survival times compared to non-vaccinated animals and diminished weight loss or pathology compared to non-vaccinated animals.

Preparation Methods

In general the fusion polypeptides of the invention, and DNA sequences encoding such fusion polypeptides, may be prepared by use of any one of a variety of procedures.

The fusion polypeptide may be produced recombinantly using a DNA sequence encoding the polypeptide, which has been inserted into an expression vector and expressed in an appropriate host. Examples of host cells are *E. coli*. The fusion polypeptides can also be produced synthetically having fewer than about 100 amino acids, and generally fewer than 50 amino acids and may be generated using techniques well known to those ordinarily skilled in the art, such as commercially available solid-phase techniques where amino acids are sequentially added to a growing amino acid chain.

The fusion polypeptides may also be produced with an additional fusion partner, by which methods superior characteristics of the polypeptide of the invention can be achieved. For instance, fusion partners that facilitate export of the polypeptide when produced recombinantly, fusion partners that facilitate purification of the polypeptide, and fusion partners which enhance the immunogenicity of the polypeptide of the invention are all interesting. The invention in particular pertains to a fusion polypeptide comprising fusions of two or more immunogenic polypeptides based on polypeptides derived from *M. tuberculosis*.

Other fusion partners, which could enhance the immunogenicity of the product, are lymphokines such as IFN-gamma, IL-2 and IL-12. In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; gluthatione S-transferase; β-galactosidase; or poly-histidine. Fusion proteins can be produced recombinantly in a host cell, which could be *E. coli*, and it is a possibility to induce a linker region between the different fusion partners. The linker region between e.g. the individual immunogenic polypeptide units may comprise 1, 2, 3, 4, 5, 6, 7, 8, 9 or 10 amino acids.

Interesting fusion polypeptides are polypeptides of the invention, which are lipidated so that the immunogenic polypeptide is presented in a suitable manner to the immune system. This effect is e.g. known from vaccines based on the *Borrelia burgdorferi* OspA polypeptide as described in e.g. WO 96/40718 A or vaccines based on the *Pseudomonas aeruginosa* OprI lipoprotein (Cote-Sierra J 1998). Another possibility is N-terminal fusion of a known signal sequence and an N-terminal cysteine to the immunogenic polypeptide. Such a fusion results in lipidation of the immunogenic fusion polypeptide at the N-terminal cysteine, when produced in a suitable production host.

Vaccine

An important aspect of the invention pertains to a vaccine composition comprising a fusion polypeptide according to the invention. In order to ensure optimum performance of such a vaccine composition it is preferred that it comprises an immunologically and pharmaceutically acceptable carrier, vehicle or adjuvant.

An effective vaccine, wherein a fusion polypeptide of the invention is recognized by the animal, will in an animal model be able to decrease bacterial load in target organs, prolong survival times and/or diminish weight loss or pathology after challenge with a virulent *Mycobacterium*, compared to non-vaccinated animals.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyloctadecylammonium bromide (DDA), dimethyloctadecenylammonium bromide (DODAC), Quil A, poly I:C, aluminium hydroxide, Freund's incomplete adjuvant, IFN-gamma, IL-2, IL-12, monophosphoryl lipid A (MPL), Trehalose Dimycolate (TDM), Trehalose Dibehenate and muramyl dipeptide (MDP) or mycobacterial lipid extract, in particular apolar lipid extracts as disclosed in PCT/DK2004/000488.

Preparation of vaccines which contain polypeptides as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFN-gamma inducers such as poly I:C in combination with the above-mentioned adjuvants.

Another interesting possibility for achieving adjuvant effect is to employ the technique described in Gosselin et al., 1992 (which is hereby incorporated by reference herein). In brief, a relevant antigen such as an antigen of the present invention can be conjugated to an antibody (or antigen binding antibody fragment) against the Fc-receptors on monocytes/macrophages.

To improve the BCG vaccine, one or more relevant antigen(s) such as one or more fusion polypeptides of the present invention can be mixed with a BCG vaccine before administration and injected together with the BCG vaccine thereby obtaining a synergistic effect leading to a better protection. Another interesting possibility for achieving a synergistic effect is to keep the BCG vaccine and the fusion polypeptide(s) of the present invention separate but use them at the same time and administer them at different sites or through different routes.

To boost the currently used BCG vaccines a relevant antigen such as one or more of the fusion polypeptides of the present invention can be administrated at the time where the BCG vaccines typically start waning or even before, such as 2, 5, 10, 15, 20, 25, 30, 35, 40, 50, 55, 60, 65 or 70 years after BCG vaccination. It could thereafter be given at regular intervals, such as 1, 2, 3, 4, 5 or 10 years, for up to 5 times.

The vaccines are administered in a manner compatible with the dosage formulation, and in such amount as will be prophylactic or therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms of the fusion polypeptide of the invention per vaccination with a preferred range from about 0.1 μg to 1000 μg, such as in the range from about 1 μg to 300 μg, and especially in the range from about 10 μg to 100 μg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral, nasal or mucosal application in either a solid form containing the active ingredients (such as a pill, suppository or capsule) or in a physiologically acceptable dispersion, such as a spray, powder or liquid, or parenterally, by injection, for example, subcutaneously, intradermally or intramuscularly or transdermally applied. The dosage of the vaccine will depend on the route of administration and will vary according to the age of the person to be vaccinated and, to a lesser degree, the size of the person to be vaccinated. Currently, most vaccines are administered intramuscularly by needle injection and this is likely to continue as the standard route. However, vaccine formulations which induce mucosal immunity have been developed, typically by oral or nasal delivery. One of the most widely studies delivery systems for induction of mucosal immunity contains cholera toxin (CT) or its B subunit. This protein enhances mucosal immune responses and induces IgA production when administered in vaccine formulations. An advantage is the ease of delivery of oral or nasal vaccines. Modified toxins from other microbial species, which have reduced toxicity but retained immunostimulatory capacity, such as modified heat-labile toxin from Gram-negative bacteria or staphylococcal enterotoxins may also be used to generate a similar effect. These molecules are particularly suited to mucosal administration.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection with virulent mycobacteria and/or to treat established mycobacterial infection or to boost a previous BCG vaccinated person. When administered to prevent an infection, the vaccine is given prophylactically, before definitive clinical signs or symptoms of an infection are present.

Due to genetic variation, different individuals may react with immune responses of varying strength to the same polypeptide. Therefore, the vaccine according to the invention may comprise several different fusion polypeptides and/or polypeptides in order to increase the immune response. The vaccine may comprise two or more fusion polypeptides or starvation induced polypeptides or immunogenic portions hereof, where all of the starvation induced antigens or fusion polypeptides are as defined above, or some but not all of the polypeptides may be derived from virulent mycobacteria. In the latter example, the polypeptides not necessarily fulfilling the criteria set forth above for fusion polypeptides may either act due to their own immunogenicity or merely act as adjuvants.

The vaccine may comprise 1-20, such as 2-20, or even 3-20 different polypeptides or fusion polypeptides, such as 3-10 different polypeptides or fusion polypeptides.

The invention also pertains to a method for immunizing an animal, including a human being, against TB caused by virulent mycobacteria, comprising administering to the animal the fusion polypeptide of the invention, or a vaccine composition of the invention as described above, or a live vaccine described above. In a presently preferred embodiment, the animal or human is an immune individual as defined above.

The invention also pertains to a method for producing an immunogenic composition according to the invention, the method comprising preparing, synthesizing or isolating a fusion polypeptide according to the invention, and solubilizing or dispersing the fusion polypeptide in a medium for a vaccine, and optionally adding other *M. tuberculosis* antigens and/or a carrier, vehicle and/or adjuvant substance.

The nucleic acid fragments of the invention may be used for effecting in vivo expression of immunogenic polypeptides, i.e. the nucleic acid fragments may be used in so-called DNA vaccines as reviewed in Ulmer et al 1993, which is included by reference.

In the construction and preparation of plasmid DNA encoding a fusion polypeptide to be used defined for DNA vaccination a host strain such as *E. coli* can be used. Plasmid DNA can then be prepared from overnight cultures of the host strain carrying the plasmid of interest, and purified using e.g. the Qiagen Giga-Plasmid column kit (Qiagen, Santa Clarita, Calif., USA) including an endotoxin removal step. It is essential that plasmid DNA used for DNA vaccination is endotoxin free.

Hence, the invention also relates to a vaccine comprising a nucleic acid fragment according to the invention, the vaccine effecting in vivo expression of the immunogenic polypeptide by an animal, including a human being, to whom the vaccine has been administered, the amount of expressed polypeptide being effective to confer substantially increased resistance to infections caused by virulent mycobacteria in an animal, including a human being.

The efficacy of such a DNA vaccine can possibly be enhanced by administering the gene encoding the expression product together with a DNA fragment encoding a polypeptide which has the capability of modulating an immune response.

One possibility for effectively activating a cellular immune response can be achieved by expressing the relevant immunogenic polypeptide in a non-pathogenic microorganism or virus. Well-known examples of such microorganisms are *Mycobacterium Bovis* BCG, *Salmonella* and *Pseudomona* and examples of viruses are Vaccinia Virus and Adenovirus.

Therefore, another important aspect of the present invention is an improvement of the live BCG vaccine presently available, wherein one or more copies of a DNA sequence encoding one or more fusion polypeptides as defined above has been incorporated into the genome of the micro-organism in a manner allowing the micro-organism to express and secrete the fusion polypeptide. The incorporation of more than one copy of a nucleic acid sequence of the invention is contemplated to enhance the immune response.

Another possibility is to integrate the DNA encoding the fusion polypeptide according to the invention in an attenuated virus such as the vaccinia virus or Adenovirus (Rolph et al 1997). The recombinant vaccinia virus is able to enter within the cytoplasma or nucleus of the infected host cell and the fusion polypeptide of interest can therefore induce an immune response, which is envisioned to induce protection against TB.

The invention also relates to the use of a fusion polypeptide or nucleic acid of the invention for use as therapeutic vaccines as have been described in the literature exemplified by D. Lowry (Lowry et al 1999). Antigens with therapeutic properties may be identified based on their ability to diminish the severity of *M. tuberculosis* infection in experimental animals or prevent reactivation of previous infection, when administered as a vaccine. The composition used for therapeutic vaccines can be prepared as described above for vaccines.

FIGURE LEGENDS

FIG. 1:

Antibody responses to Rv2660c for HIV-negative (TB+/HIV−) and HIV-positive (TB+/HIV+) TB patients from Uganda and healthy controls from Denmark (Controls). The cut-off was based on ROC-curve analysis with a specificity level of 97%. The observed sensitivity is shown above the graphical presentation of the data.

Figure 2:
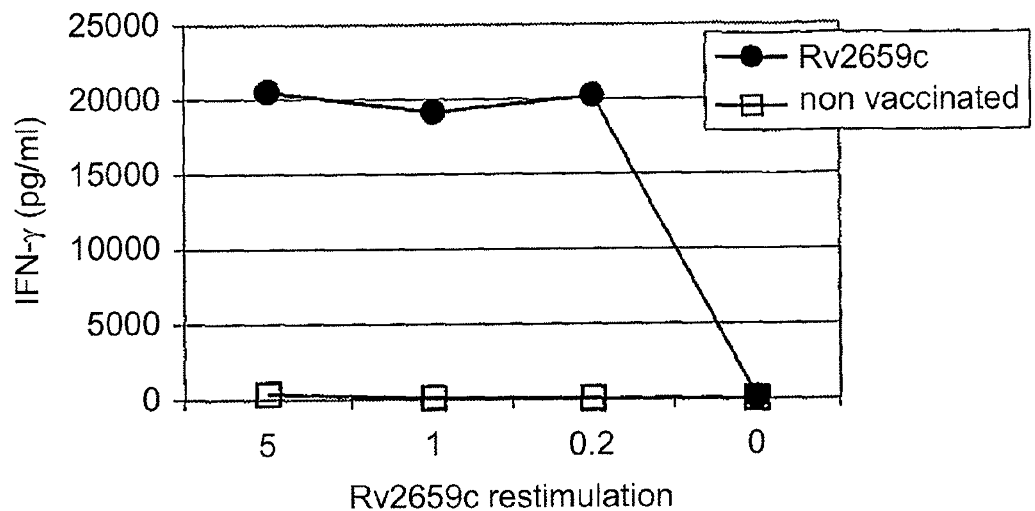

FIG. 2: Immunogenicity of Rv2659c

Groups of F1(Balb/cxC57BL/6) mice were subcutaneously vaccinated three times at two-week intervals with Rv2659c in DDA/MPL. One week after the final vaccination, PBMCs were analyzed by ELISA for IFN-gamma secretion following stimulation with 5 microgram/ml Rv2659c.

Figure 3:
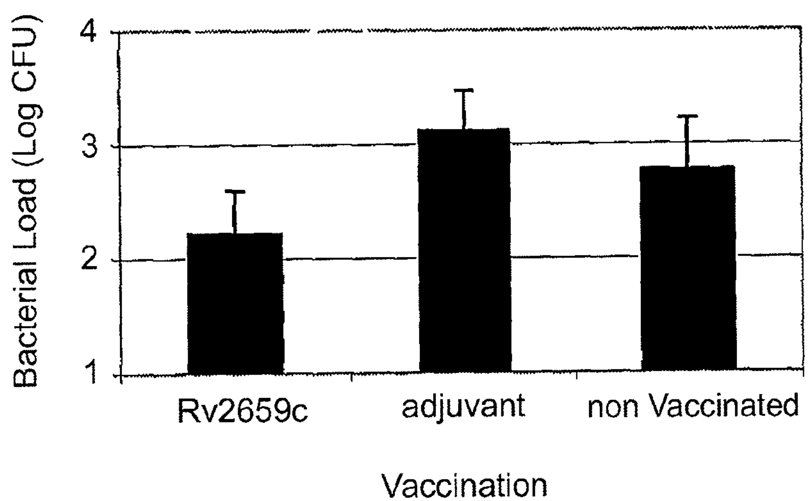

FIG. 3: Rv2659c induce protection against infection with *M. tuberculosis*

Groups of Balb/c-C57BL/6 mice were subcutaneously vaccinated three times at two-week intervals with Rv2659c and protective efficacy was assessed by reduction in CFU counts in lungs and compared to unimmunized and BCG immunized mice 12 weeks after vaccination. Results are expressed as $\log_{10}$ colony forming units (CFU) in the lung and are mean results from 6 mice per experimental group.

Figure 4:
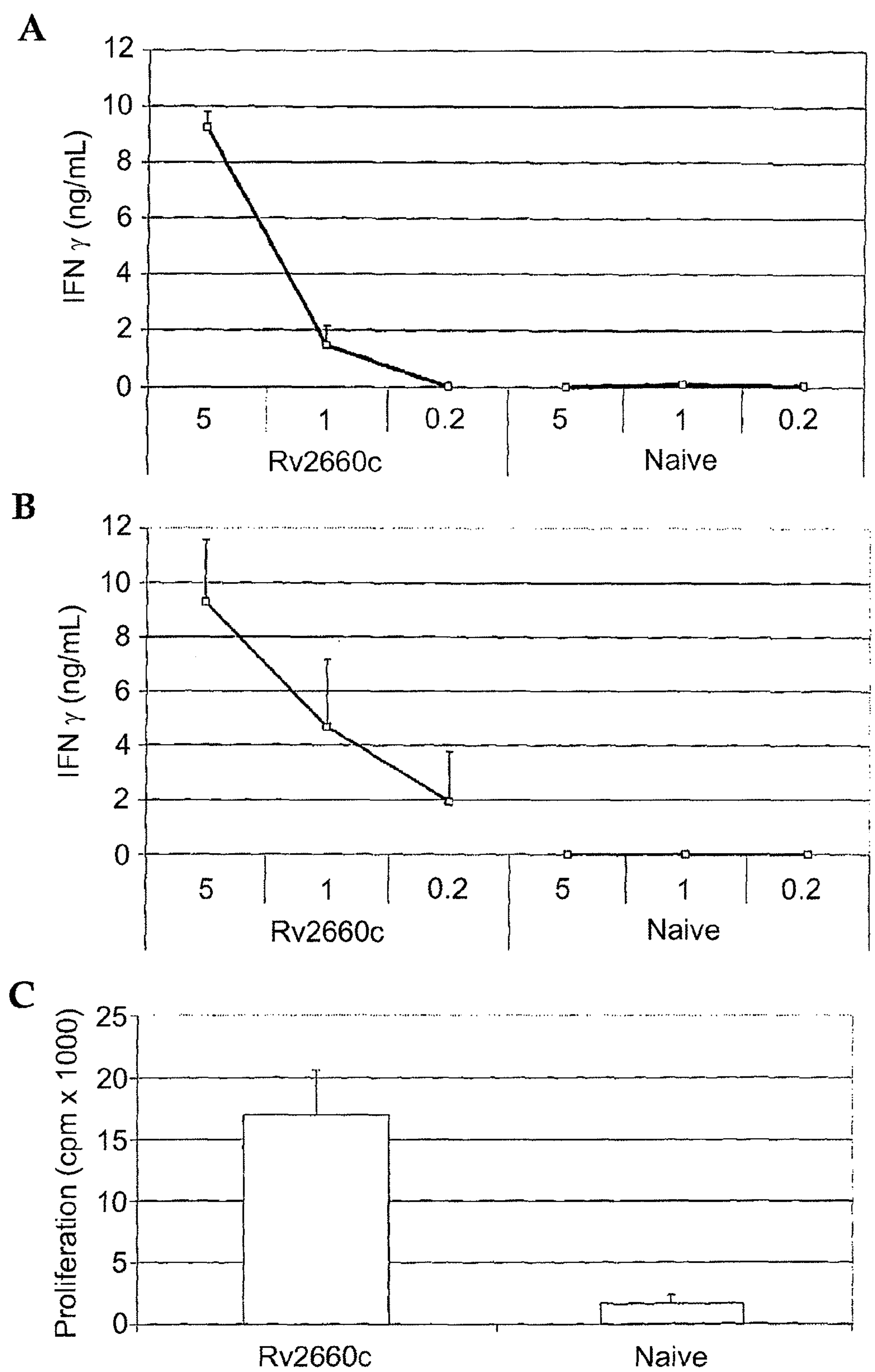

FIG. 4: Immunogenicity of Rv2660c

F1(Balb/cxC57BL/6) mice were subcutaneously vaccinated three times at two-week intervals with recombinant Rv2660c protein in DDA/MPL. (A) One week after the final vaccination, PBMCs were analyzed by ELISA for IFN-gamma release following stimulation with 0.2, 1 or 5 microgram/ml of Rv2660c. Three weeks after the final vaccination, spleen cells (B) were analyzed by ELISA for IFN-gamma secretion following stimulation with 0.2, 1, or 5 microgram/ml recombinant Rv2660c and PBMCs (C) were analyzed for proliferative responses after stimulation with 0.2, 1 or 5 microgram/ml recombinant Rv2660c.

Figure 5:
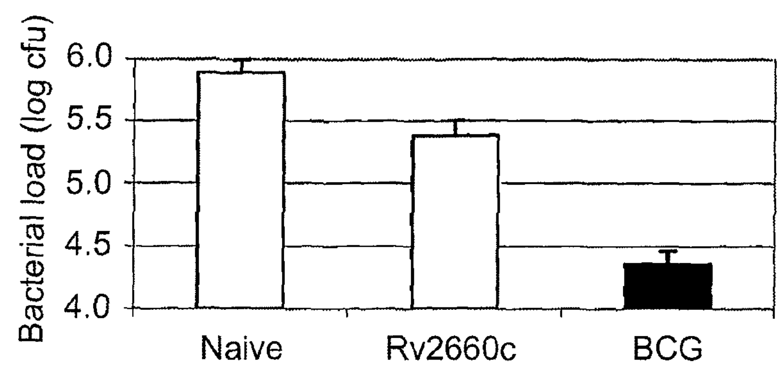

FIG. 5: Protection against infection with *Mycobacterium tuberculosis* induced by Rv2660c Groups of Balb/c-C57BL/6 mice were subcutaneously vaccinated three times at two-week intervals with Rv2660c, and protective efficacy was assessed by CFU counts in lungs and compared to unimmunized and BCG immunized mice 6 weeks after aerosol infection. Results are expressed as $\log_{10}$ colony forming units (CFU) in the lung and are mean results from 6 mice per experimental group. As a positive control, a single dose of BCG Danish 1331 ($5\times10^4$ bacilli/mouse) was injected s.c. at the base of the tail at the same time as the first subunit vaccination; no booster injections were administered.

Figure 6:
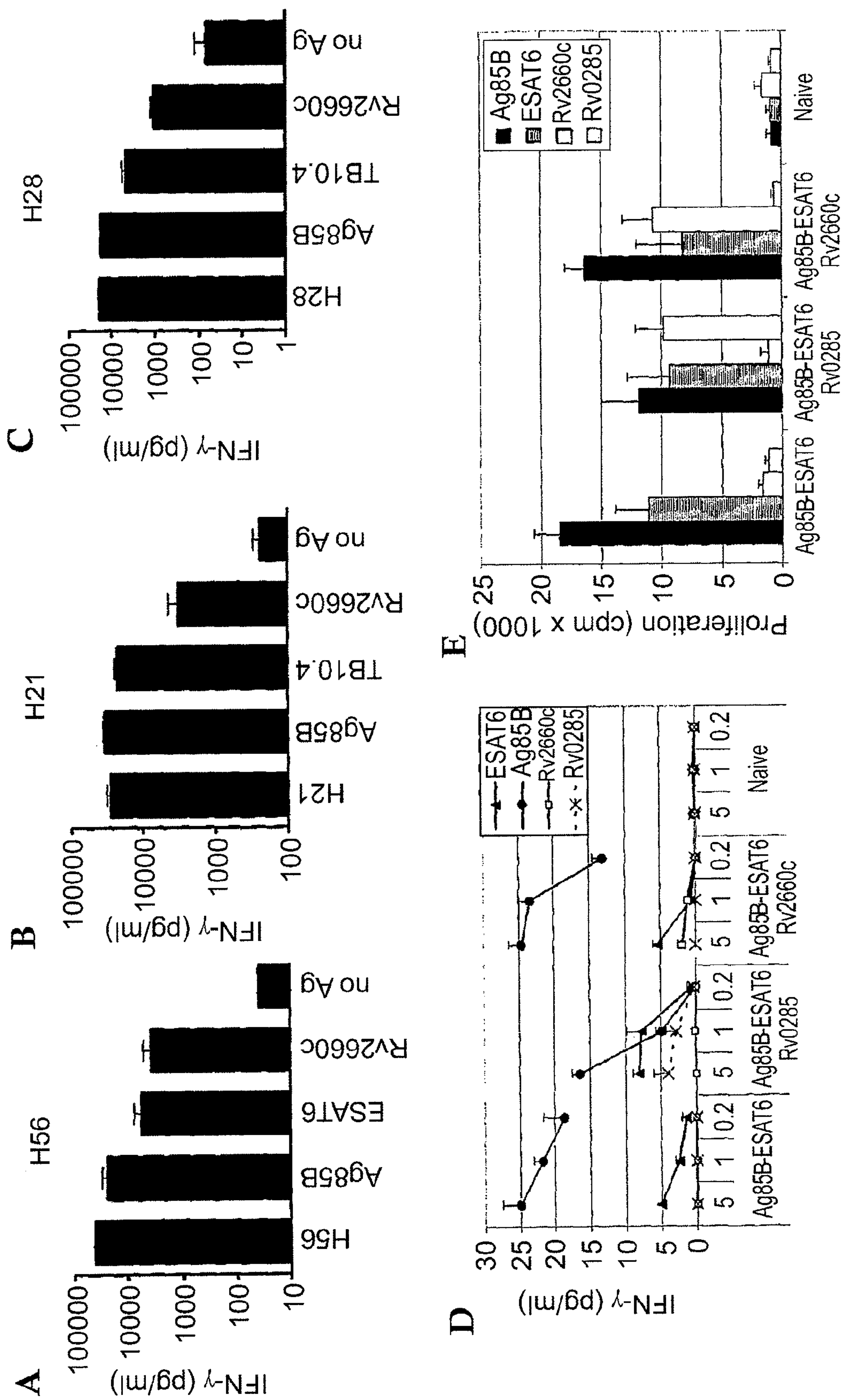

FIG. 6: Immunogenicity of Hybrid56, HyVac21 and HyVac28

Groups of F1(Balb/cxC57BL/6) mice were subcutaneously vaccinated three times at two-week intervals with 5 microgram Ag85B-ESAT6-Rv2660c (H56), Ag85A-TB10.4-Rv2660c (H21) or Ag85B-TB10.4-Rv2660c (H28) in DDA/TDB (LipoVac). One week after the final vaccination, PBMCs were analyzed by ELISA for IFN-gamma release following stimulation with 1 microgram/ml of the fusion protein used for immunization, Ag85B, TB10.4 or Rv2660c (FIG. 6A-C).

Three weeks after the final vaccination with Ag85B-ESAT6-Rv2660c, spleen cells (D) were analyzed by ELISA for IFN-gamma secretion following stimulation with 0.2, 1, or 5 microgram/ml recombinant Ag85B, ESAT6, or Rv2660c and PBMCs (E) were analyzed for proliferative responses against the same antigens at 1 microgram/ml.

Figure 7:
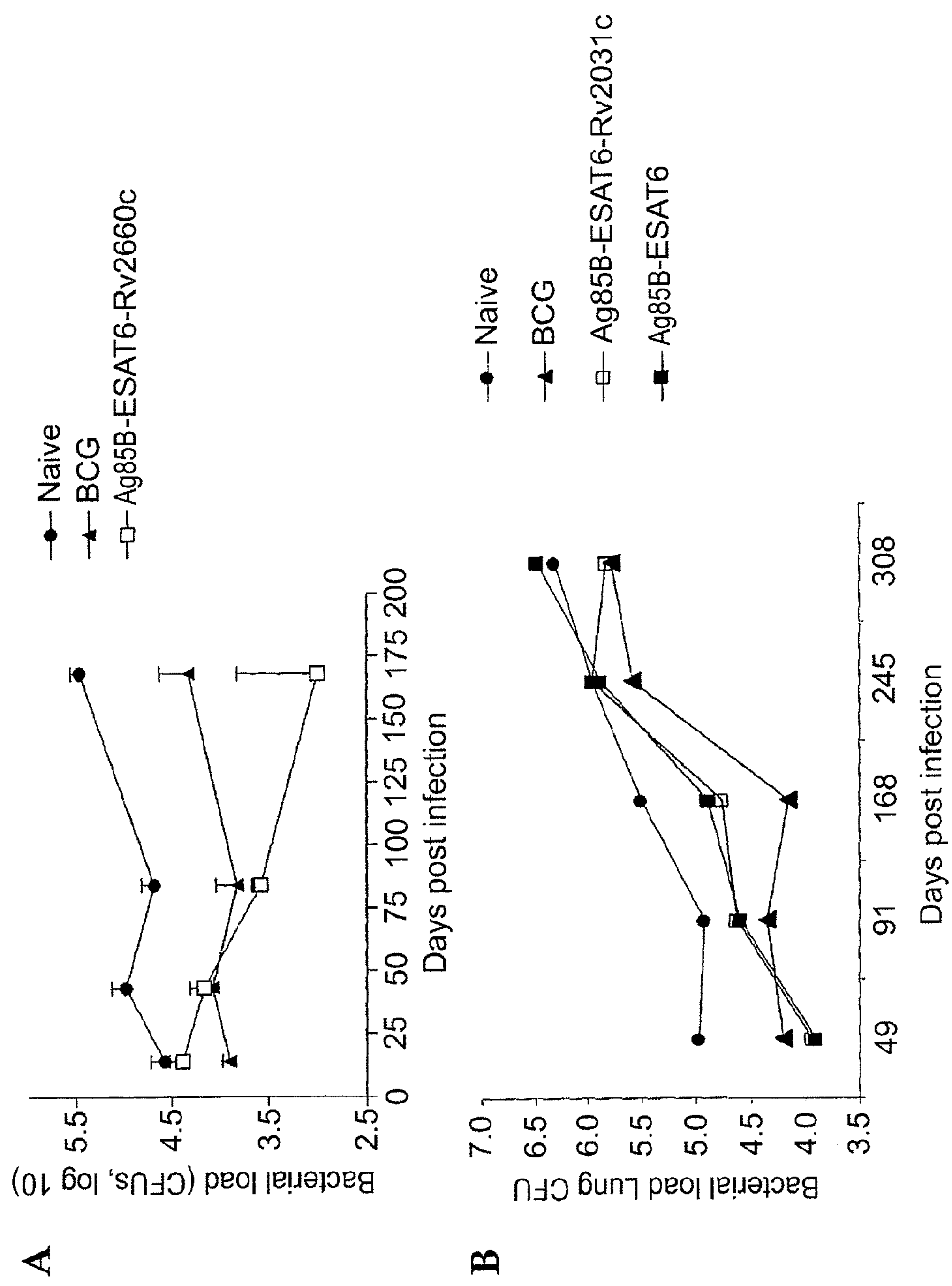

FIG. 7: Strong protection against *M. tuberculosis* infection after immunization with Hybrid56

(A) Groups of Balb/c-C57BL/6 mice were subcutaneously vaccinated three times at two-week intervals with Ag85B-ESAT6-Rv2660c (Hybrid56), and protective efficacy was assessed by CFU counts in lungs and compared to unimmunized and BCG immunized mice 2, 6, 12 and 24 weeks after aerosol infection. (B) Groups of B6 mice were subcutaneously vaccinated three times at two-week intervals with either Ag85B-ESAT6 (Hybrid1) or Ag85B-ESAT6-Rv2031c (Hybrid32) and protective efficacy was assessed by CFU counts in lungs and compared to unimmunized and BCG immunized mice 7, 13, 24, 35 and 44 weeks after aerosol infection Results are expressed as $\log_{10}$ colony forming units (CFU) in the lung and are mean results from 6 mice per experimental group. As a positive control, a single dose of BCG Danish 1331 ($5\times10^4$ bacilli/mouse) was injected s.c. at the base of the tail at the same time as the first subunit vaccination; no booster injections were administered.

Figure 8:
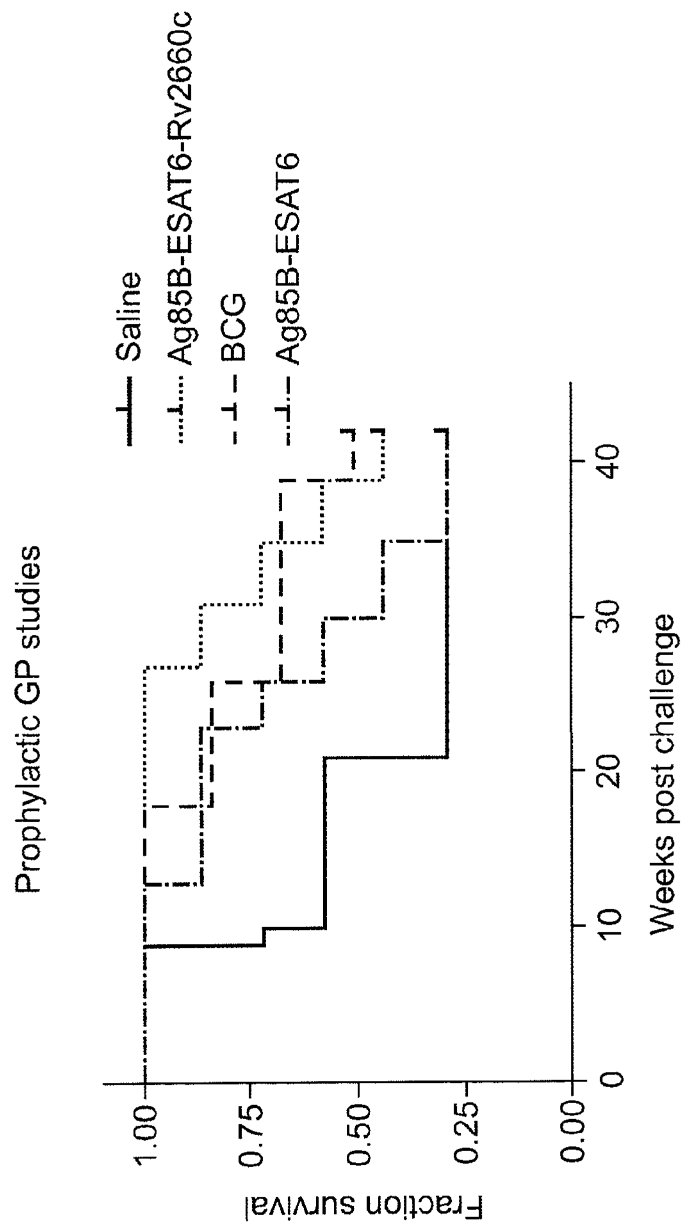

FIG. 8: Kaplan-Meier survival curves (n=7)

Immunization of guinea pigs with Ag85B-ESAT6-Rv2660c fusion protein prolongs survival time to the level of BCG immunized animals after low-dose aerosol *M. tuberculosis* challenge.

Figure 9:
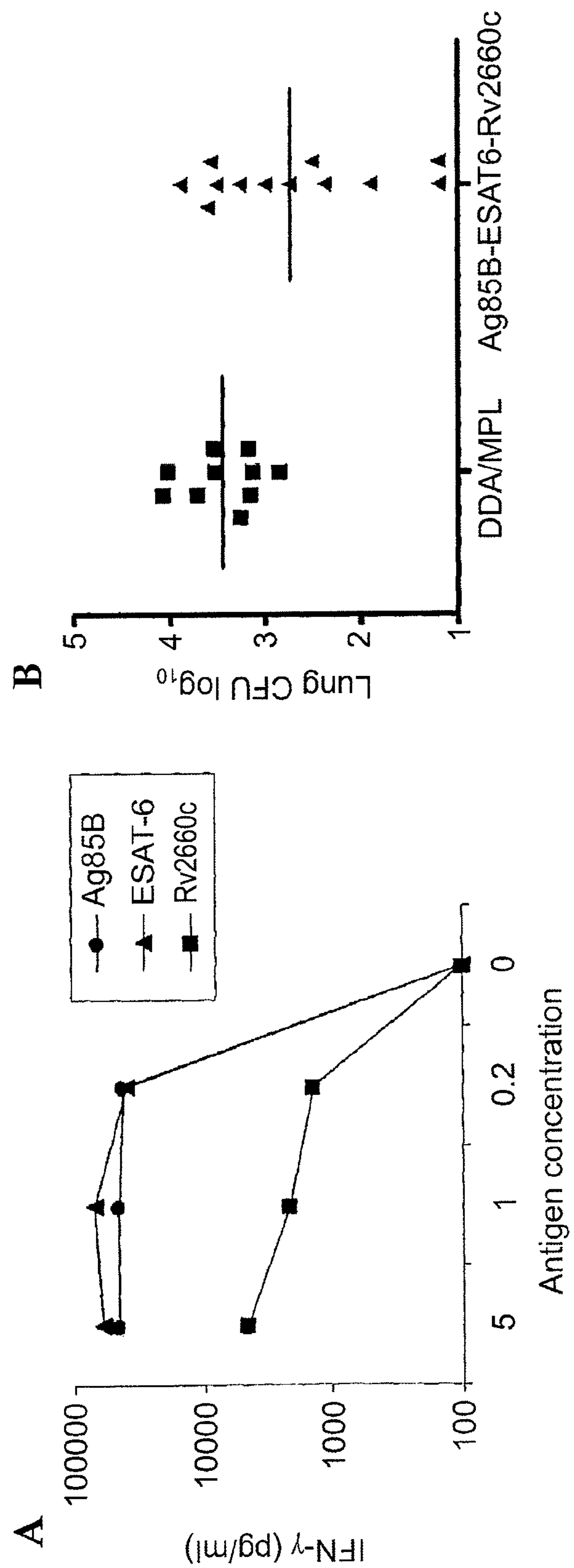

FIG. 9: Hybrid56 (Ag85B-ESAT6-Rv2660c) induced immunogenicity and protection F1(Balb/cxC57BL/6) mice were subcutaneously vaccinated three times at two-week intervals with Ag85B-ESAT6-Rv2660c (Hybrid56) in DDA/MPL. Ten weeks after the final vaccination, spleen cells were analyzed by ELISA for IFN-gamma secretion following stimulation with 0.2, 1, or 5 ug/ml Ag85B, ESAT6, or Rv2660c (as noted in FIG. 9A). Protective efficacy was assessed by reduction in CFU counts in lungs compared to adjuvant control immunized mice ten weeks after vaccination. Results are expressed as $\log_{10}$ colony forming units (CFU) in the lung from 12 mice per experimental group (FIG. 9B).

EXAMPLES

A. Materials and Methods

B. Animals

Female specific-pathogen-free C57BL/6xBalb/C F1 or C57BL/6 mice, 8 to 16 weeks of age, obtained from Bomholtegaard, Denmark were used for analysis of immune responses and studies of protection as assessed by CFU analysis. Infection studies were performed in the BSL3 facilities at Statens Serum Institute. Animals were housed in isolator cages and fed water and sterile food ad libitum. All animals were allowed a 1-week rest period before initiation of experiments.

C. Recombinant Antigen Preparations

Recombinant Ag85B-ESAT6 (Hybrid1) was produced as previously described (Olsen, van Pinxteren et al. 2001). Briefly, the His-tagged protein was expressed in *Escherichia coli* XL-1 Blue and purified on a Talon column followed by protein anion-exchange chromatography using a HiTrap Q column (Pharmacia, Uppsala, Sweden). The sample was dialyzed against 25 mM HEPES buffer (pH 8.0)-0.15 M NaCl-10% glycerol-0.01% Tween 20 before dilution and storage.

Recombinant Rv2660c was produced by the same procedure previously described for other small mycobacterial protein (Skjot, Oettinger et al. 2000). Briefly, the full-length Rv2660c gene was PCR-amplified from *M. tuberculosis* genomic DNA and subcloned into the expression plasmid pDest17. The recombinant protein was produced in *Escherichia coli* Bl21 blue and purified by metal ion affinity chromatography on a Ni+ column essentially as described previously (Theisen, Vuust et al. 1995) but with phosphate buffers containing 8 M urea, which was removed after the purification.

The Hybrid56 (Ag85B-ESAT6-Rv2660c), Hybrid32 (Ag85B-ESAT6-Rv2031c), HyVac21 (Ag85A-TB10.4-Rv2660c) and HyVac28 (Ag85B-TB10.4-Rv2660c) fusion proteins were cloned into expression vector pDest17 (Invitrogen) by site-specific recombination according to the manufacturer.

The fusion proteins were expressed in *E. coli* strain BL21 after induction by IPTG. All four recombinant fusion proteins were collected as inclusion bodies after disruption of the cells by mild detergent (B-PER, Sigma) and sonication. Washed inclusion bodies were dissolved in 20 mM NaOAc+8 M urea at pH 4.9 and passed over an Q sepharose column to capture endotoxin. The collected run-through was diluted in Bis-tris buffer+8 M urea pH 6.5 and the pH was adjusted to pH 6.5. The protein was then passed over a CM sepharose to capture impurities and then captured on a Q sepharose column. The column was washed with bis-tris buffer pH 6.5+3 M urea. Bound proteins were eluted with NaCl. The protein was then buffer exchanged on a Sephadex column to 25 mM tris-HCl pH 8 and 10% glycerol.

Human Recognition—Serology

All sera were depleted of cross-reactive antibodies prior to use in ELISA by addition of 20 μl of *E. coli* extract (S3761, Promega, Madison, Wis.) to 200 μl serum sample followed by incubation for 4 hours at room temperature while mixing. After centrifugation (10.000×g, 10 min), 0.05% sodium azide was added to the supernatant. The ELISA was performed as follows, 96-well Maxisorp (Nunc, Roskilde, Denmark) microtiter plates were coated over night at 4° C. with antigen at 1.0 μg/ml (100 μl per well) in carbonate-bicarbonate buffer (pH 9.6). Plates were then washed 3 times with PBS containing 0.05% Tween 20 (PBS-T). Serum samples were diluted 1:100 in PBS containing 0.2% Tween 20 and 1.0% (wt/vol) bovine serum albumin (dilution buffer), and 0.1 ml of diluted serum was added to the wells in duplicate, and incubated for one hour at room temperature. After washings 3× with PBS-T, plates were incubated for one hour with 100 ul Peroxidase conjugated rabbit-anti-human Ig (P212, DAKO, Glostrup, Denmark) diluted 1:8000 in dilution buffer. Plates were washed 3 times with PBS-T and incubated with Tetramethylbenzidine substrate (TMB plus, Kem-En-Tec, Taastrup, Denmark) for 30 minutes, and the development was stopped by addition of 1 M $H_2SO_4$. Optical density at 405 nm ($OD_{405}$) was then measured.

D. Vaccine Preparation and Immunization Procedure

Mice were immunized with 5 micro g recombinant vaccine (either Rv2659c, Rv2660c, Hybrid56, HyVac21, HyVac28 or Hybrid32) delivered in 25 μg monophosphoryl lipid A (MPL, Corixa, Wash., USA) emulsified in dioctadecylammonium bromide (DDA, 250 μg/dose, Eastman Kodak, Inc., Rochester, N.Y.) in a total volume of 200 μl, as recently described (Olsen, van Pinxteren et al. 2001). The vaccines (0.2 ml/mice) were injected three times subcutaneously (s.c.) on the back with 2-week intervals. A single dose of BCG Danish 1331 ($5\times10^4$ bacilli/mouse) was injected s.c. at the base of the tail at the same time as the first subunit vaccination; no booster injections were administered. The prechallenge immunity was typically evaluated with blood lymphocytes 5 and 7 weeks after the first vaccination and splenocytes 7 weeks after first vaccination.

E. Experimental Infections and Bacterial Enumeration in Organs

To evaluate the level of protection, mice were challenged 10 weeks after the first immunization either by the aerosol route in a Glas-Col inhalation exposure system, calibrated to deliver approximately 100 CFU of *M. tuberculosis* Erdman per lung. Mice were sacrificed 2, 6, 12 or 24 weeks later (Hybrid56), or 7, 13, 24, 35 or 44 weeks later (Hybrid32), and lungs and spleens were removed for bacterial enumeration. The organs were homogenized separately in sterile saline, and serial dilutions were plated onto Middlebrook 7H11 agar supplemented with 2 mg of 2-thiophene-carboxylic acid hydrazide per ml to selectively inhibit the growth of residual BCG in the test organs. Colonies were counted after 2 to 3 weeks of incubation at 37° C.

F. Lymphocyte Cultures

Organs were homogenized by maceration through a fine mesh stainless steel sieve into complete RPMI (GIBCO, Grand Island, N.Y., including 2 mM glutamine, 100 U/ml each of penicillin 6-potassium and streptomycin sulphate, 10% FCS and 50 mM 2-ME).

Blood lymphocytes were purified on a density gradient lympholyte (Cedarlane, Hornby, Ontario, Canada). Cells were pooled from five mice in each group and cultured in triplicate in round-bottomed microtiter wells (96 well; Nunc, Roskilde, Denmark) containing $2\times10^5$ cells in a volume of 200 microl of RPMI 1640 medium supplemented with $5\times10^{-5}$ M 2-mercaptoethanol, 1 mM glutamine, penicillin-streptomycin 5% (vol/vol) fetal calf serum. The mycobacterial antigens were used in concentrations ranging from 5 to 0.2 mg/ml. Cultures were incubated at 37° C. in 10% CO2 for 3 days, before the removal of 1000 of supernatant for gamma interferon (IFN-gamma determination by enzyme-linked immunosorbent assay (ELISA) as described below.

G. Enzyme-Linked Immunosorbent Assay (ELISA) for IFN-Gamma

A double sandwich ELISA method was used to quantify the levels of IFN-gamma in duplicate titrations of culture supernatants, using a commercial kit for IFN-gamma assay, in accordance with the manufacturer's instructions (Mabtech, AB. Sweden). Concentrations of IFN-gamma in the samples were calculated using a standard curve generated from recombinant IFN-gamma (Life Technologies) and results are expressed in pg/ml. The difference between the duplicate wells was consistently less than 10% of the mean.

Experimental infection and vaccine efficacy evaluation in the guinea pig model.

Outbred female Hartley guinea pigs purchased from Charles River Laboratories (North Wilmington, Mass.) was given either BCG intradermally at a dose of $10^3$ CFU once or 20 μg of either Ag85B-ESAT6 or Ag85B-ESAT6-Rv2660c emulsified in DDA/MPL three times with a rest period of 3 weeks between immunizations. Six weeks after third immunization an aerosol MTB challenge was given using a device (Glas-Col, Terre Haute, Ind.) calibrated to deliver approximately 20 bacilli into each guinea pig lung. Survival times for infected guinea pigs were determined by observing animals on a daily basis for changes in food consumption, evidence of labored breathing, and behavioral changes. In addition, animals were weighed on a weekly basis until a sustained drop in weight was observed over several days, indicating illness.

H. Example 1

Human Recognition of a Starvation Induced Antigen

Rv2660c was evaluated for human recognition in a panel of pulmonary TB patients from Uganda provided by the WHO Tuberculosis Specimen Bank. Both patients with negative and positive HIV infection status were included (N=94 and N=73, respectively). The control group consisted of one hundred healthy, Danish resident donors with an estimated BCG coverage >90%.

Microtiter plates were coated with 1.0 μg/ml (100 μl per well) Rv2660c protein incubated with 100× diluted serum samples and developed using peroxidase conjugated rabbit-anti-human Ig and tetramethylbenzidine as substrate (results in FIG. 1).

Conclusion

In this study, the recognition of a starvation-induced protein was tested. Based upon a cutoff determined from the control group using a sensitivity of 97% if was possible to confirm the TB infection in 45% of the HIV− cases and 61% of the HIV+ cases. Clearly indicating that the RV2660c protein is expressed and recognized by the immune system during a MTB infection.

I. Example 2

Immunogenicity and Prevention of Reactivation by Post-Exposure Administration of a Starvation Induced Antigen (Rv2659c)

Mice were infected with *M. tuberculosis* and treated with antibiotics to reduce the bacterial burden and enter a stage of latent infection with a bacterial burden close to detection level. During the latent stage of infection the mice were vaccinated three times at two-week intervals with Rv2659c in adjuvant (e.g. DDA/MPL). One week after the final vaccination, blood cells are analyzed by ELISA for IFN-gamma secretion following stimulation with Rv2659c (FIG. 2).

The Ability of the Starvation Induced Protein Rv2659c to Induce Protection Against Reactivation of *M. tuberculosis*

Groups of mice with latent *M. tuberculosis* were subcutaneously vaccinated three times at two-week intervals with Rv2659c formulated in adjuvant (e.g. DDA/MPL) and protective efficacy were assessed by reduction in colony forming units (CFU) from lungs and spleens when compared to non-vaccinated (latently infected) mice. Protection against reactivation was evaluated three months after vaccination. Rv2659c induced a 3 to 90 fold reduction in pulmonary bacterial levels compared to reactivated unimmunized latently infected mice (FIG. 3). To evaluate the influence of the Rv2659c vaccination on the possible development of pathology in the latently infected mice, lung tissue was taken from latently infected vaccinated mice for histopathological examination. No significant caseous necrosis, fibrosis or mineralization was detected in the lesions and no enhanced infiltration of inflammatory cells was seen.

Conclusion

In this study, the potential of a starvation induced protein, Rv2659c as a therapeutic vaccine was tested. When the Rv2659c protein was administered to mice in the adjuvant combination dimethyldioctadecylammonium bromide-monophosphoryl lipid A, a strong immune response was induced/boosted. The immunization resulted in 0.5-1.0 log reduction in the bacterial burden in the lung. Thus our studies suggest that post-exposure vaccination reduces or delays reactivation of *M. tuberculosis* without triggering pulmonary immunopathology.

J. Example 3

Immunogenicity and Protection Against Aerosol *M. tuberculosis* Infection by the Starvation Induced Antigen Rv2660c Mice were vaccinated three times at two-week intervals with Rv2660c in adjuvant (e.g. DDA/MPL). One week after the final vaccination, blood cells are analyzed by ELISA for IFN-gamma secretion following stimulation with Rv2660c (FIG. 4A). Three weeks after final vaccination spleen cells are analyzed for IFN-gamma secretion following stimulation with Rv2660c (FIG. 4B) and blood cells are analyzed for antigen specific proliferative responses (FIG. 4C).

Groups of mice subcutaneously vaccinated three times at two-week intervals with Rv2660c formulated in adjuvant (e.g. DDA/MPL) were challenged by aerosol infection with *M. tuberculosis* and the protective efficacy was assessed by reduction in colony forming units (CFU) isolated from lungs when compared to non-vaccinated mice. Protection was evaluated 12 weeks after vaccination. Rv2660c induced ½ $\log_{in}$ reduction in pulmonary bacterial levels compared to unimmunized infected mice (FIG. 5).

Conclusion

In this study, the potential of a starvation induced protein, Rv2660c as a vaccine antigen was tested. When the Rv2660c protein was administered to mice in the adjuvant combination dimethyldioctadecylammonium bromide-monophosphoryl lipid A, a strong immune response was induced. The immunization resulted in approximately 0.5 $\log_{10}$ reduction in the bacterial burden in the lung.

K. Example 4

Fusion of Starvation Induced Antigens to Preventive Vaccines (Multiphase Vaccine)

Immunological Responses after Immunization with Triple Fusion Proteins

Groups of mice are subcutaneously vaccinated two times at two-week intervals with the fusion polypeptides Hybrid56, HyVac21 or HyVac28 in adjuvant (e.g. DDA/MPL). One week after the final vaccination, blood cells are analyzed for IFN-gamma secretion following stimulation with 1 microgram/ml immunization fusion protein or the single components in the fusion proteins (FIG. 6A-C). Three weeks after the final vaccination with Hybrid56, Ag85b-ESAT6, or Ag85b-ESAT6-Rv0285, spleen cells are analyzed by ELISA for IFN-gamma secretion following stimulation with 0.2, 1, or 5 microgram/ml of the single components in the fusion protein (FIG. 6D). Blood cells are analyzed for antigen specific proliferative responses three weeks after final vaccination (FIG. 6E).

The Ability of Three Fusion Polypeptides to Induce Protection Against Infection with *M. tuberculosis* in Mice Groups of mice are subcutaneously vaccinated three times at two-week intervals with the fusion polypeptides Hybrid1, Hybrid56 and Hybrid32 in adjuvant (DDA/MPL) and protective efficacy are assessed by reduction in colony forming units (CFU) from lungs and spleens when compared to naive (non-vaccinated) mice after aerosol infection. As a positive control for protection, a single dose of BCG Danish 1331 (5×104 bacilli/mouse) is injected s.c. at the base of the tail at the same time as the first subunit vaccination (FIGS. 7A and B).

Protective Ability of the Polypeptide Hybrid56 (Ag85b-ESAT6-Rv2660c) Against an Aerosol *M. tuberculosis* Infection in Guinea Pigs Groups of guinea pigs are subcutaneously vaccinated three times at three-week intervals with the fusion polypeptide in adjuvant (e.g. DDA/MPL) and protective efficacy are primarily assessed by measuring each animals weigh on a weekly basis. As a positive control for protection, a single dose of BCG Danish 1331 (5×104 bacilli/mouse) is injected i.d. at the same time as the first subunit vaccination. Results are presented as survival curves in FIG. 8.

Conclusion

In this study the immunological potential of three fusion proteins (Hybrid56, HyVac21 and HyVac28) were investigated. When the fusion proteins were administered to mice in the adjuvant combination dimethyl dioctadecylammonium bromide-monophosphoryl lipid A, a strong dose-dependent immune response was induced to all three single protein components indicating its potential as a multi-phase vaccine. Selecting Hybrid56 as an example the immune responses induced were accompanied by high levels of protective immunity that increase with time, reaching a level that was clearly above the protection level reached with *Mycobacterium bovis* BCG, the classical MTB vaccine. Further, a similar triple fusion protein containing the classical MTB latency antigen Rv2031c (Ag85B-ESAT6-Rv2031c) replacing Rv2660c, did not show improved protection over time. Finally, the high level of protection for Hybrid56 was confirmed in the much more susceptible guinea pig model.

L. Example 5

Activity of a Fusion of a Starvation Induced Antigen and a Preventive Vaccine (Multiphase Vaccine) Administered Post Exposure (Therapeutically)

Mice were infected with *M. tuberculosis* and treated with antibiotics to reduce the bacterial burden and enter a stage of latent infection with a low bacterial burden. During the latent stage of infection the mice were vaccinated three times at two-week intervals with the fusion polypeptide in adjuvant (e.g. DDA/MPL). Fifteen weeks after the final vaccination, blood cells are analyzed by ELISA for IFN-gamma secretion following stimulation with 0.2, 1, or 5 ug/ml of single components of the fusion protein. (FIG. 9A).

The Ability of the Fusion Polypeptide to Induce Protection Against Reactivation of *M. tuberculosis*

Groups of mice with latent *M. tuberculosis* were subcutaneously vaccinated three times at two-week intervals with the fusion polypeptide formulated in adjuvant (e.g. DDA/MPL) and protective efficacy were assessed by reduction in colony forming units (CFU) from lungs when compared to non-vaccinated (latently infected) mice. Protection against reactivation was evaluated three months after vaccination. The fusion polypeptide induced a significant reduction of reactivation resulting in reduced pulmonary bacterial levels compared to reactivated unimmunized latently infected mice (FIG. 9B).

Conclusion

In this study, the potential of a tuberculosis subunit vaccine based on a fusion protein of the antigens Rv2660c, ESAT6 (Rv3875) and antigen 85B (Rv1886c) as a therapeutic vaccine was investigated. When fusion protein was administered to mice in the adjuvant combination dimethyldioctadecylammonium bromide-monophosphoryl lipid A, a strong immune response was induced/boosted. The immunization resulted in a reduction in the bacterial burden in the lung during reactivation of latent infection. Thus our studies suggest that post-exposure vaccination with fusion of a starvation induced antigen and a preventive vaccine (Multiphase vaccine) reduces or delays reactivation of *M. tuberculosis*.

REFERENCES

Andersen, P., and Heron, I. 1993 J. Immunol. Methods 161 29-39
Andersen, P. et al 1991. Infect. Immun. 59:1905-1910
Betts J. C. et al 2002. Mol Microbiol. 43:717-731
Brandt, L., et al. 2000 Infect. Immun. 68:2; 791-795.
Brooks, J. V., Frank, A. A., Keen, M. A., Bellisle, J. T. & Orme, I. M. Infect Immun 2001, 69(4), 2714-2717.
Colditz, G. A., Brewer, T. F., Berkey, C. S. et al. JAMA 1994, 271, 698-702
Cole, S. T et al 1998 Nature 393: 537-544
Cote-Siena J, et al 1998, Gene October 9; 221(1):25-34
Gosselin et al., (1992) J. Immunol. 149: 3477-3481
Harboe, M., et al 1998 Infect. Immun. 66:2; 717-723
Honer zu Bentrup, K., Russell, D. G. 2001, Trends Microbiol. 9(12): 597-605
Lowry, D. B. et al 1999, Nature 400: 269-71
Lyashchenko, K. P., et al 2000. J Immunological Methods 242: 91-100
Nagai et al 1991, Infect. Immun 59:1; 372-382
Danish Patent application PA 2000 00666 “Nucleic acid fragments and polypeptide fragments derived from *M. tuberculosis”*
Danish Patent application PA 1999 01020 (WO 01/23388) “Tuberculosis vaccine and diagnostic based on the *Mycobacterium tuberculosis* esat-6 gene family”.
Patent application U.S. Ser. No. 09/0505,739 “Nucleic acid fragments and polypeptide fragments derived from *M. tuberculosis”*
Pollock. J., et al, 2000. The Veterinary record, 146:659-665
Rolph, M. S, and I. A. Ramshaw. 1997. Curr. Opin. Immunol. 9:517-24
Rosenkrands, I., et al 1998, Infect. Immun 66:6; 2728-2735
Sambrook et al Molecular Cloning; A laboratory manual, Cold Spring Harbor Laboratories, NY, 1989
Sherman, D. R. et al. 2001 Proc Natl Acad Sci USA 98: 7534-7539
Skjøt, R. L. V., et al 2000, Infect. Immun 68:1; 214-220
Stryhn, A., et al 1996 Eur. J. Immunol. 26:1911-1918
Thompson J., et al Nucleic Acids Res 1994 22:4673-4680
Ulmer J. B et al 1993, Curr. Opin. Invest. Drugs 2(9): 983-989
Olsen A. W et al, Eur J Immunol. 2000 June; 30(6):1724-32
Olsen, A. W., L. A. van Pinxteren, et al. (2001) Infect Immun 69(5): 2773-8.
Theisen, M., J. Vuust, et al. (1995) Clin Diagn Lab Immunol 2(1): 30-4.
Ravn, P. et al 1999. J. Infect. Dis. 179:637-645
Kilgus J et al, J Immunol. 1991 Jan. 1; 146(1):307-15
Sinigaglia F et al. Nature 1988 Dec. 22-29; 336(6201):778-80
Pearson W. R and D. J. Lipman (1988) PNAS USA 85:2444-2448
Kohler and Milstein, Nature, 256:495 (1975)
McCafferty et al, Nature, 348:552-554 (1990)
Merrifield, R. B. Fed. Proc. Am. Soc. Ex. Biol. 21: 412, 1962 and J. Am. Chem. Soc. 85: 2149, 1963
Mowat et al 1991, Immunology 72(3):317-22
Lustig et al 1976, Cell Immunol 24(1):164-72

What is claimed is:

1. An immunogenic composition comprising a fusion polypeptide that comprises at least 12 consecutive amino acids of SEQ ID NO: 38.

2. The immunogenic composition according to claim 1, wherein said fusion polypeptide further comprises ESAT6, Ag85B, TB10.4 or Ag85A; or any two or more of ESAT6, Ag85B, TB10.4 or Ag85A.

3. The immunogenic composition according to claim 1, wherein said immunogenic composition is formulated for intradermal, transdermal, subcutaneous, intramuscular, or mucosal delivery.

4. The immunogenic composition according to claim 2, wherein the fusion polypeptide comprises 2 different immunogenic polypeptides.

5. The immunogenic composition according to claim 2, wherein the fusion polypeptide comprises 3 different immunogenic polypeptides.

6. The immunogenic composition according to claim 2, wherein the fusion polypeptide comprises 4 different immunogenic polypeptides.

7. The immunogenic composition according to claim 1, wherein the fusion polypeptide comprises an amino acid sequence selected from the group consisting of:

Ag85B-ESAT6-Rv1284;
Ag85B-TB10.4-Rv1284;
Ag85B-Rv1284;
Ag85A-Rv1284;
Ag85A-ESAT6-Rv1284;
Ag85A-TB10.4-Rv1284;
Rv1284-Rv2659c; and
Ag85B-ESAT6-Rv1284-Rv2659c; or
any two or more of:
Ag85B-ESAT6-Rv1284;
Ag85B-TB10.4-Rv1284;
Ag85B-Rv1284;
Ag85A-Rv1284;
Ag85A-ESAT6-Rv1284;
Ag85A-TB10.4-Rv1284;
Rv1284-Rv2659c; or
Ag85B-ESAT6-Rv1284-Rv2659c.

8. The immunogenic composition of claim 1, further comprising an adjuvant.

9. An immunogenic composition comprising a nucleic acid that comprises a nucleic acid sequence encoding at least 12 consecutive amino acids of SEQ ID NO: 38 and an adjuvant.

10. The immunogenic composition according to claim 9, wherein said nucleic acid further encodes ESAT6, Ag85B, TB10.4 or Ag85A; or any two or more of ESAT6, Ag85B, TB10.4 or Ag85A.

11. The immunogenic composition according to claim 9, wherein said immunogenic composition is formulated for intradermal, transdermal, subcutaneous, intramuscular, or mucosal delivery.

12. The immunogenic composition according to claim 10, wherein said nucleic acid encodes at least 2 different immunogenic polypeptides.

13. The immunogenic composition according to claim 10, wherein said nucleic acid encodes at least 3 different immunogenic polypeptides.

14. The immunogenic composition according to claim 10, wherein said nucleic acid encodes at least 4 different immunogenic polypeptides.

15. The immunogenic composition according to claim 9, wherein said nucleic acid encodes at least an amino acid sequence selected from the group consisting of:

Ag85B-TB10.4-Rv1284;
Ag85B-Rv1284;
Ag85A-Rv1284;
Ag85A-ESAT6-Rv1284;
Ag85A-TB10.4-Rv1284;
Rv1284-Rv2659c; and
Ag85B-ESAT6-Rv1284-Rv2659c; or
any two or more of:
Ag85B-ESAT6-Rv1284;
Ag85B-TB10.4-Rv1284;
Ag85B-Rv1284;
Ag85A-Rv1284;
Ag85A-ESAT6-Rv1284;
Ag85A-TB10.4-Rv1284;
Rv1284-Rv2659c; or
Ag85B-ESAT6-Rv1284-Rv2659c.

16. A method of immunizing an animal against tuberculosis comprising administering to said animal the immunogenic composition according to claim 1.

17. A method of immunizing an animal against tuberculosis comprising administering to said animal the immunogenic composition according to claim 9.

* * * * *